United States Patent
Le Hir de Fallois et al.

(10) Patent No.: US 12,083,100 B1
(45) Date of Patent: *Sep. 10, 2024

(54) ANTIPARASITIC ISOXAZOLINE COMPOUNDS, LONG-ACTING INJECTABLE FORMULATIONS COMPRISING THEM, METHODS AND USES THEREOF

(71) Applicant: BOEHRINGER INGELHEIM ANIMAL HEALTH USA INC., Duluth, GA (US)

(72) Inventors: Loic Patrick Le Hir de Fallois, Atlanta, GA (US); Charles Q. Meng, Grayson, GA (US); Susan Mancini Cady, Yardley, PA (US); Peter Cheifetz, East Windsor, NJ (US); Izabela Galeska, Newtown, PA (US)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/938,063

(22) Filed: Oct. 5, 2022

Related U.S. Application Data

(60) Continuation of application No. 16/534,912, filed on Aug. 7, 2019, now Pat. No. 11,497,732, which is a division of application No. 15/441,297, filed on Feb. 24, 2017, now abandoned.

(60) Provisional application No. 62/379,348, filed on Aug. 25, 2016, provisional application No. 62/299,333, filed on Feb. 24, 2016.

(51) Int. Cl.

| | |
|---|---|
| *A61K 31/422* | (2006.01) |
| *A01N 43/80* | (2006.01) |
| *A61K 9/00* | (2006.01) |
| *A61K 31/415* | (2006.01) |
| *A61K 31/42* | (2006.01) |
| *A61K 47/10* | (2017.01) |
| *A61K 47/14* | (2017.01) |
| *C07D 261/04* | (2006.01) |
| *C07D 413/04* | (2006.01) |
| *C07D 471/04* | (2006.01) |
| *C07D 491/107* | (2006.01) |
| *A61K 9/08* | (2006.01) |
| *A61K 9/10* | (2006.01) |
| *A61K 9/107* | (2006.01) |

(52) U.S. Cl.
CPC ............ *A61K 31/415* (2013.01); *A01N 43/80* (2013.01); *A61K 9/0019* (2013.01); *A61K 31/42* (2013.01); *A61K 31/422* (2013.01); *A61K 47/10* (2013.01); *A61K 47/14* (2013.01); *C07D 261/04* (2013.01); *C07D 413/04* (2013.01); *C07D 471/04* (2013.01); *C07D 491/107* (2013.01); *A61K 9/0095* (2013.01); *A61K 9/08* (2013.01); *A61K 9/10* (2013.01); *A61K 9/107* (2013.01)

(58) Field of Classification Search
CPC .... A61K 31/415; A61K 9/0019; A61K 31/42; A61K 31/422; A61K 47/10; A61K 47/14; A61K 9/0095; A61K 9/08; A61K 9/10; A61K 9/107; A01N 43/80; C07D 261/04; C07D 413/04; C07D 471/04; C07D 491/107; A61P 33/14
See application file for complete search history.

(56) References Cited

U.S. PATENT DOCUMENTS

| | | | |
|---|---|---|---|
| 6,645,984 B2 | 11/2003 | Braun et al. | |
| 8,022,089 B2 | 9/2011 | Mita et al. | |
| 8,410,153 B2 | 4/2013 | Lahm et al. | |
| 9,371,293 B2 | 6/2016 | Nishiguchi et al. | |
| 2005/0250822 A1 | 11/2005 | Mita et al. | |
| 2009/0133319 A1 | 5/2009 | Lahm et al. | |
| 2010/0254959 A1* | 10/2010 | Lahm ............... | A61P 33/14 514/357 |
| 2011/0245274 A1 | 10/2011 | Nanchen et al. | |
| 2013/0203692 A1* | 8/2013 | Soll .................. | A61K 31/437 514/378 |
| 2013/0210623 A1 | 8/2013 | Cassayre et al. | |

(Continued)

FOREIGN PATENT DOCUMENTS

| | | |
|---|---|---|
| CN | 101765592 A | 6/2010 |
| CN | 104168900 A | 11/2014 |
| CN | 104602529 A | 5/2015 |

(Continued)

OTHER PUBLICATIONS

Kilp, Susanne, et al. "Pharmacokinetics of Fluralaner in Dogs Following a Single Oral or Intravenous Administration." Parasites & Vectors, vol. 7, No. 1, 2014, pp. 85-85.

(Continued)

*Primary Examiner* — Monica A Shin
(74) *Attorney, Agent, or Firm* — Katrina Bergbauer

(57) ABSTRACT

This invention relates to long-acting injectable compositions for combating parasites in animals, comprising at least one isoxazoline active agent, a liquid PEG and/or a neutral oil, optionally a co-solvent, and optionally a pharmaceutically acceptable additive or excipient. This invention also provides new isoxazoline active agents with long-lasting efficacy against ectoparasites. The invention also provides for improved methods for eradicating, controlling, and preventing parasite infections and infestations in an animal comprising administering the novel isoxazoline compounds and long-acting injectable compositions of the invention to the animal in need thereof.

19 Claims, No Drawings

(56) References Cited

U.S. PATENT DOCUMENTS

| | | |
|---|---|---|
| 2014/0121194 A1 | 5/2014 | Ikari et al. |
| 2018/0169073 A1 | 6/2018 | Flochlay-Sigognault et al. |

FOREIGN PATENT DOCUMENTS

| | | | |
|---|---|---|---|
| CN | 105026395 | A | 11/2015 |
| EP | 1731512 | A1 | 12/2006 |
| EP | 2172448 | A1 | 4/2010 |
| EP | 2193124 | B1 | 12/2012 |
| JP | 2007016017 | A | 1/2007 |
| JP | 2016145160 | A | 8/2016 |
| NO | 2009024541 | A2 | 2/2009 |
| WO | 2005074912 | A2 | 8/2005 |
| WO | 2007079162 | A1 | 7/2007 |
| WO | 2008154528 | A2 | 12/2008 |
| WO | 2009002809 | A2 | 12/2008 |
| WO | 2010070068 | A2 | 6/2010 |
| WO | 2011075591 | A1 | 6/2011 |
| WO | 2011104089 | A1 | 9/2011 |
| WO | 2011149749 | A1 | 12/2011 |
| WO | 2011157733 | A2 | 12/2011 |
| WO | 2011157748 | A1 | 12/2011 |
| WO | 2012017359 | A1 | 2/2012 |
| WO | 2012084670 | A1 | 6/2012 |
| WO | 2012107533 | A1 | 8/2012 |
| WO | 2012120135 | A1 | 9/2012 |
| WO | 2012120399 | A1 | 9/2012 |
| WO | 2013039948 | A1 | 3/2013 |
| WO | 2013078070 | A1 | 5/2013 |
| WO | 2013079407 | A1 | 6/2013 |
| WO | 2013119442 | A1 | 8/2013 |
| WO | 2014039475 | A1 | 3/2014 |
| WO | 2014140075 | A1 | 9/2014 |
| WO | 2014189837 | A1 | 11/2014 |
| WO | 2015048371 | A1 | 4/2015 |
| WO | 2015066277 | A1 | 5/2015 |
| WO | 2016138339 | A1 | 9/2016 |
| WO | 2016164487 | A1 | 10/2016 |
| WO | 2017176948 | A1 | 10/2017 |

OTHER PUBLICATIONS

XP002769912 Database WPI Week 200720 Thomson Scientific, London, GB; AN 2007-294920.

Shi, Yi, et al. "Recent Advances in Intravenous Delivery of Poorly Water-Soluble Compounds." Expert Opinion on Drug Delivery, vol. 6, No. 12, 2009, pp. 1261-1282.

Matschke, Christian, et al. "Sustained-Release Injectables Formed in Situ and Their Potential Use for Veterinary Products." Journal of Controlled Release, vol. 85, No. 1-3, 2002, pp. 1-15.

Alexander, Amit, et al. "Poly(Ethylene Glycol)-Poly(Lactic-Co-Glycolic Acid) Based Thermosensitive Injectable Hydrogels for Biomedical Applications." Journal of Controlled Release, vol. 172, No. 3, 2013, pp. 715-729.

Patani, George, et al. "Bioisosterism: A Rational Approach in Drug Design." Chemical Reviews, vol. 96, No. 8, 1996, pp. 3147-3176, https://doi.org/10.1021/cr950066q.

Hatefi, A., and B. Amsden "Biodegradable Injectable in Situ Forming Drug Delivery Systems." Journal of Controlled Release, vol. 80, No. 1-3, 2002, pp. 9-28.

* cited by examiner

ANTIPARASITIC ISOXAZOLINE COMPOUNDS, LONG-ACTING INJECTABLE FORMULATIONS COMPRISING THEM, METHODS AND USES THEREOF

CROSS REFERENCE TO RELATED APPLICATIONS

This application is a continuation application of U.S. patent application Ser. No. 16/534,912, filed Aug. 7, 2019, which is a divisional application of U.S. patent application Ser. No. 15/441,297, filed Feb. 24, 2016, which claims the benefit of priority to U.S. Provisional Application Nos. 62/299,333, filed Feb. 24, 2016, and 62/379,348, filed Aug. 25, 2016, all of which are incorporated herein by reference in their entireties.

FIELD OF THE INVENTION

The present invention provides pesticidal and antiparasitic isoxazoline compounds, and long-acting injectable compositions comprising at least one isoxazoline active agent, a liquid polyethylene glycol (PEG) and, optionally, a co-solvent. The invention also provides for the use of these compounds and compositions against pests and parasites (including ectoparasites (e.g., fleas or ticks) and/or endoparasites), and methods for controlling pests and preventing or treating parasitic infections and infestations in animals.

CROSS REFERENCE TO RELATED APPLICATIONS

This application claims the benefit of priority to U.S. Provisional Application Nos. 62/299,333, filed Feb. 24, 2016, and 62/379,348, filed Aug. 25, 2016, both of which are incorporated herein by reference.

BACKGROUND OF THE INVENTION

Animals such as mammals and birds are often susceptible to parasite infestations/infections. These parasites may be ectoparasites, such as fleas, ticks and parasitic flies, and endoparasites such as nematodes and other worms. Domesticated animals, such as cats and dogs, are often infested with one or more of the following ectoparasites:
  fleas (e.g. *Ctenocephalides* spp., such as *Ctenocephalides felis* and the like);
  ticks (e.g. *Rhipicephalus* spp., *Ixodes* spp., *Dermacentor* spp., *Amblyomma* spp., and the like);
  mites (e.g. *Demodex* spp., *Sarcoptes* spp., Otodectes spp., and the like);
  lice (e.g. *Trichodectes* spp., *Cheyletiella* spp., *Linognathus* spp. and the like);
  mosquitoes (*Aedes* spp., *Culex* spp., *Anopheles* spp. and the like); and
  flies (*Haematobia* spp., *Musca* spp., *Stomoxys* spp., *Dermatobia* spp., *Cochliomyia* spp. and the like).

Fleas are a particular problem because not only do they adversely affect the health of the animal or human, but they also cause a great deal of psychological stress. Moreover, fleas may also transmit pathogenic agents to animals and humans, such as tapeworm (*Dipylidium caninum*).

Similarly, ticks are also harmful to the physical and psychological health of the animal or human. However, the most serious problem associated with ticks is that they are vectors of pathogenic agents in both humans and animals. Major diseases which may be transmitted by ticks include borreliosis (Lyme disease caused by *Borrelia burgdorferi*), babesiosis (or piroplasmosis caused by *Babesia* spp.) and rickettsioses (e.g. Rocky Mountain spotted fever). Ticks also release toxins which cause inflammation or paralysis in the host. Occasionally, these toxins are fatal to the host.

Likewise, farm animals are also susceptible to parasite infestations. For example, cattle and other bovines are affected by a large number of parasites. A parasite which is prevalent among cattle in some regions are ticks of the genus *Rhipicephalus*, especially those of the species *microplus* (cattle tick), *decoloratus* and *annulatus*. Ticks such as *Rhipicephalus microplus* (formerly *Boophilus microplus*) are difficult to control because they lay eggs in the pasture where farm animals graze. This species of ticks is considered a one-host tick and spends immature and adult stages on one animal before the female engorges and falls off the host to lay eggs in the environment. The life cycle of the tick is approximately three to four weeks. In addition to cattle, *Rhipicephalus microplus* may infest buffalo, horses, donkeys, goats, sheep, deer, pigs, and dogs. A heavy tick burden on animals can decrease production and damage hides as well as transmit diseases such as babesiosis ("cattle fever") and anaplasmosis.

Animals and humans also suffer from endoparasitic infections including, for example, helminthiasis which is caused by of parasitic worms categorized as cestodes (tapeworm), nematodes (roundworm) and trematodes (flatworm or flukes). These parasites adversely affect the nutrition of the animal and cause severe economic losses in pigs, sheep, horses, and cattle as well as affecting companion animals and poultry. Other parasites which occur in the gastrointestinal tract of animals and humans include those from the genus *Ancylostoma*, *Necator*, *Ascaris*, *Strongyloides*, *Trichinella*, *Capillaria*, *Toxocara*, *Toxascaris*, *Trichuris*, *Enterobius* and parasites which are found in the blood or other tissues and organs such as filarial worms and the extra intestinal stages of *Strongyloides*, *Toxocara* and *Trichinella*.

Recently, isoxazole and isoxazoline-containing compounds have been demonstrated to be effective against parasites that harm animals. For example, U.S. Pat. No. 7,964,204 (to DuPont, incorporated by reference herein in its entirety) discloses isoxazoline compounds according to formula (I) below, which are active against ectoparasites and/or endoparasites.

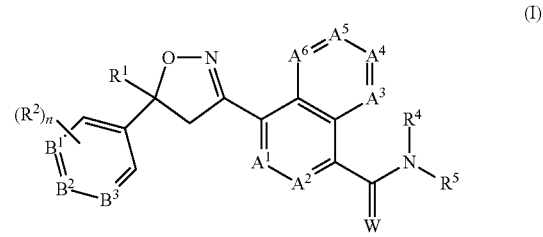

In addition, published patent application nos. US 2010/0254960 A1, WO 2007/070606 A2, WO 2007/123855 A2, WO 2010/003923 A1, U.S. Pat. No. 7,951,828 & U.S. Pat. No. 7,662,972, US 2010/0137372 A1, US 2010/0179194 A2, US 2011/0086886 A2, US 2011/0059988 A1, US 2010/0179195 A1 and WO 2007/075459 A2 and U.S. Pat. Nos. 7,951,828 and 7,662,972 describe various other parasiticidal isoxazoline compounds. Other published patent applications that describe various other parasiticidal isoxazoline compounds and compositions comprising the same include WO 2007/079162 A1, WO 2008/154528 A1, WO 2009/002809 A2, WO 2011/149749 A1, WO 2014/439475 A1, U.S. Pat. No. 8,466,115, WO 2012/120399, WO 2014/039484, WO 2014/189837, (Zoetis) and WO2012 120135A1 (Novartis). WO 2012/089623 describes topical localized isoxazoline compositions comprising glycofurol. WO 2013/039948 A1 provides for topical veterinary compositions comprising at least one isoxazoline active agent and WO 2013/119442 A1 provides for oral veterinary compositions such as a soft chew which comprising at least one isoxazoline active agent.

In additional to topical and oral dosage forms, it is sometimes possible to formulate active agents as long-acting compositions, depending upon, for example, the physio-chemical properties of the individual active agent; these properties include, for example, solubility, bioavailability, etc. For example, U.S. Pat. Nos. 6,733,767 and 8,362,086 provide for long acting injectable compositions comprising a bioactive substance, such as, for example, an avermectin or a milbemycin and a biological acceptable polymer.

Notwithstanding the highly active isoxazoline active agents and compositions comprising isoxazoline active agents alone or in combination with other active agents described in the documents above, there is a need for more effective isoxazoline compounds and veterinary compositions and methods with improved efficacy, bioavailability, and spectrum of coverage to protect animals against endoparasites and/or ectoparasites. More specifically, there is a need to develop a long-acting injectable composition comprising an isoxazoline compound, which has good bioavailability and exhibits a reduced irritation at the injection site while still being effective against parasites (e.g., fleas and ticks) for a long duration (e.g., from three (3) to six (6) months.

INCORPORATION BY REFERENCE

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

SUMMARY OF THE INVENTION

In a first aspect, the present invention provides for novel and inventive long-acting injectable compositions for the treatment or prevention of parasite infections or infestations in an animal comprising an antiparasitic effective amount of at least one isoxazoline compound, a liquid PEG and/or a pharmaceutically acceptable neutral oil, optionally, a co-solvent and optionally a pharmaceutically acceptable additive or excipient.

In accordance with the first aspect of the present invention, it has been discovered that the inventive long-acting compositions generally show desirable bioavailability and duration of efficacy, while causing minimal irritation at the injection site. The compositions also provide desirable safety profiles toward the warm-blooded and bird animal recipients. In addition, it has been discovered that a single administration of such compositions generally provides potent activity against one or more parasites (e.g., ectoparasites), while also tending to provide fast onset of activity, long duration of activity, and/or desirable safety profiles.

The invention encompasses uses or veterinary uses of the isoxazoline compounds and compositions described herein for the treatment or prevention of parasitic infections and infestations in or on animals (either wild or domesticated), including livestock and companion animals such as cats, dogs, horses, chickens, sheep, goats, pigs, turkeys and cattle, with the aim of ridding these hosts of parasites commonly encountered by such animals.

In addition, the compounds of formula (Id) described herein are useful for protecting crops, plants, plant propagation material, or material containing wood or derived from wood, from harmful pests.

The invention also provides methods for the treatment or prevention of parasitic infections and infestations in animals, comprising administering an effective amount of long-acting injectable compositions comprising an antiparasitic effective amount of at least one isoxazoline compound together with at least one liquid PEG and/or a pharmaceutically acceptable neutral oil and optionally a co-solvent, a pharmaceutically acceptable additive and/or excipient, wherein the composition does not contain a pharmaceutically acceptable biodegradable polymer as defined herein. Surprisingly, it has been found that the inventive isoxazoline-containing compositions described herein exhibit superior broad spectrum efficacy against harmful parasites (e.g. ectoparasites such as fleas and ticks) more rapidly, and over a long duration compared to other injectable compositions containing isoxazoline active agents known in the art while exhibiting minimal irritation at the injection site.

This invention also provides for the use of an isoxazoline in the preparation of a long-acting injectable composition for the treatment or prevention of an animal against parasites.

In one embodiment, the invention provides for long-acting injectable compositions comprising antiparasitic effective amounts of at least one isoxazoline of formula (I) below, in combination and a pharmaceutically or veterinary acceptable liquid carrier, where variables $A^1, A^2, A^3, A^4, A^5, A^6, B^1, B^2, B^3, R^1, R^2, R^4, R^5$, W and n are defined herein.

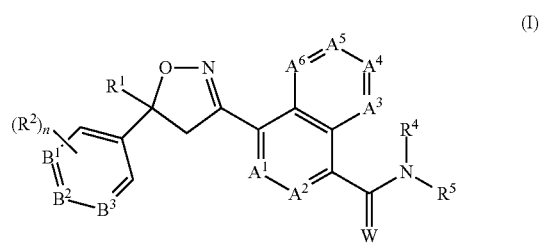

(I)

In another embodiment, the invention provides long-acting injectable compositions comprising an isoxazoline compound of formula (Ic):

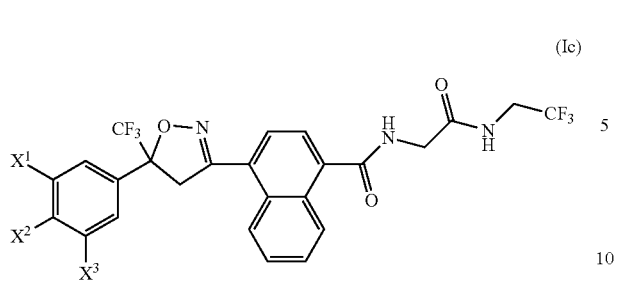

(Ic)

or a pharmaceutically acceptable salt thereof; wherein $X^1$, $X^2$ and $X^3$ are each independently H, halogen, $C_1$-$C_3$alkyl or $C_1$-$C_3$haloalkyl. Long acting compositions comprising a compound of formula (Ic) wherein $X^1$ is chloro, $X^2$ is fluoro and $X^3$ is $CF_3$ have been shown to have surprisingly long-lasting and excellent efficacy against *Rhipicephalus microplus* with a quick onset and a very long duration of time.

In another embodiment, the long-acting injectable compositions and methods comprise 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalenecarboxamide as the active agent.

In other embodiments, the long-acting injectable compositions may further comprise one or more additional active agents that are systemically active. Systemically-acting active agents may include, but are not limited to, isoxazoline active agents of different structure, a systemically-acting neonicotinoid active agent, a systemically-acting 1-N-arylpyrazole active agent, macrocyclic lactones such as avermectin and milbemycin compounds, a cyclic depsipeptide such as emodepside or PF1022A or analogs thereof, benzimidazoles, imidazothiazoles, a tetrahydropyrimidine active agent, an organophosphate active agent, levamisole, a paraherquamide active agent and/or a marcfortine active agent, praziquantel, closantel, clorsulon, morantel, pyrantel, a spinosyn or spinosoid active agent, an amino acetonitrile active agent, an aryloazol-2-yl cyanoethyl active agent, a systemically-acting insect growth regulator. In one embodiment, the long-acting injectable compositions comprise at least one macrocyclic lactone active agent, including, but not limited to, avermectins or milbemycins. In some embodiments, the avermectin or milbemycin active agent is eprinomectin, ivermectin, selamectin, milbemectin, milbemycin D, milbemycin oxime, or moxidectin.

In other embodiments, the compositions and methods comprise at least one of thiabendazole, oxibendazole, mebendazole, fenbendazole, oxfendazole, albendazole, triclabendazole, febantel, levamisole, pyrantel, morantel, praziquantel, closantel, clorsulon, an amino acetonitrile active agent, or an aryloazol-2-yl cyanoethylamino active agent.

In a second aspect, the invention provides novel and inventive pesticidal and parasiticidal isoxazoline compounds of formula (Id) shown:

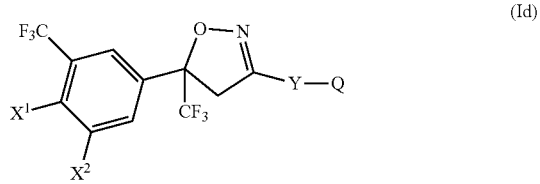

(Id)

wherein $X^1$ is bromo, chloro, iodo or fluoro; and $X^2$ is chloro, fluoro or $CF_3$;

Y is a group Y-1, Y-2, Y-3, Y-4 where Z is N or CH, Y-5 or Y-6

Y-1

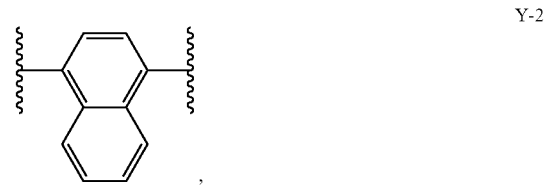

Y-2

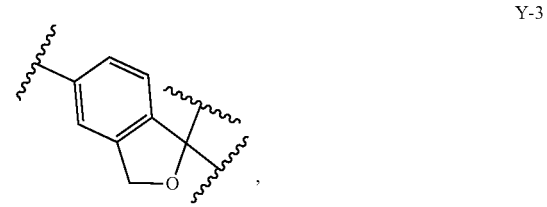

Y-3

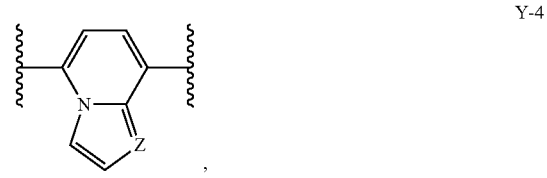

Y-4

Y-5

or

Y-6

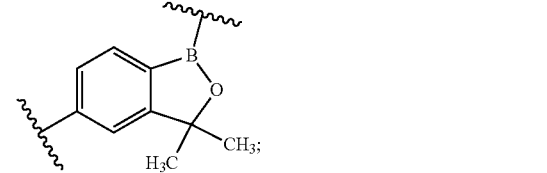

and Q is OH, —C(O)NHCH$_2$C(O)NHCH$_2$CF$_3$, —C(O)CH$_2$S(O)$_2$CH$_3$, —C(O)NHCH$_2$CH$_2$SCH$_3$ or (—CH$_2$—)(—CH$_2$—)N(CO)CH$_2$S(O)$_2$CH$_3$.

The compounds of formula (Id) are highly active against arthropod pests and parasites and useful for protecting animals, including livestock and companion animals such as cats, dogs, horses, chickens, sheep, goats, pigs, turkeys and cattle, from parasites that infest or infect such animals. The invention also provides pesticidal isoxazoline compounds of formula (Id) for protecting crops, plants, plant propagation material, or material containing wood or derived from wood, from harmful pests.

It is an object of the invention to not encompass within the invention any previously known product, process of making the product, or method of using the product such that the Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

These and other embodiments are disclosed or are obvious from and encompassed by, the following Detailed Description.

DETAILED DESCRIPTION

Long-Acting Injectable Compositions

In a first aspect, the present invention provides for novel and inventive long-acting injectable compositions for the treatment or prevention of parasitic infections or infestations in an animal comprising an antiparasitic effective amount of at least one isoxazoline compound, a liquid PEG and/or a pharmaceutically acceptable neutral oil, and optionally a co-solvent, a pharmaceutically acceptable additive and/or excipient, wherein no other pharmaceutically acceptable polymers, as defined herein are present.

Also provided are methods and uses for the treatment and/or prophylaxis of parasitic infections and infestations in or on animals, comprising administering to an animal in need thereof a long-acting composition comprising an antiparasitic effective amount of at least one isoxazoline compound, a liquid PEG and/or a pharmaceutically acceptable neutral oil, and optionally a co-solvent, a pharmaceutically acceptable additive and/or excipient.

In another embodiment, the present invention provides for long-acting injectable compositions for the treatment and/or prophylaxis of parasitic infections and infestations in or on animals comprising an antiparasitic effective amount of at least one isoxazoline compound and an effective amount of at least one additional active agent, a PEG and/or a pharmaceutically acceptable neutral oil and, optionally, a co-solvent, a pharmaceutically acceptable additive and/or excipient.

In another embodiment, the present invention provides for a long-acting injectable composition for the treatment and/or prophylaxis of parasitic infections and infestations in or on animals comprising:
a) an antiparasitic effective amount of at least one isoxazoline active agent, which is:
i) an isoxazoline compound of formula (I):

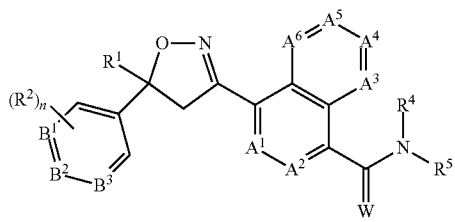

(I)

wherein:
$A^1$, $A^2$, $A^3$, $A^4$, $A^5$ and $A^6$ are independently selected from the group consisting of $CR^3$ and N, provided that at most 3 of $A^1$, $A^2$, $A^3$, $A^4$, $A^5$ and $A^6$ are N;
$B^1$, $B^2$ and $B^3$ are independently selected from the group consisting of $CR^2$ and N; W is O or S;

$R^1$ is $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^6$;

each $R^2$ is independently H, halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, —CN or —NO$_2$;

each $R^3$ is independently H, halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN or —NO$_2$;

$R^4$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^5$ is H, $OR^{10}$, $NR^{11}R^{12}$ or $Q^1$; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one or more substituents independently selected from $R^7$; or $R^4$ and $R^5$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of $C_1$-$C_2$ alkyl, halogen, —CN, —NO$_2$ and $C_1$-$C_2$ alkoxy;

each $R^6$ is independently halogen, $C_1$-$C_6$ alkyl, $C_1$-$C_6$ alkoxy, $C_1$-$C_6$ alkylthio, $C_1$-$C_6$ alkylsulfinyl, $C_1$-$C_6$ alkylsulfonyl, —CN or —NO$_2$;

each $R^7$ is independently halogen; $C_1$-$C_6$ alkyl, $C_3$-$C_6$ cycloalkyl, $C_1$-$C_6$ alkoxy, $C_1$-$C_6$ alkylthio, $C_1$-$C_6$ alkylsulfinyl, $C_1$-$C_6$ alkylsulfonyl, $C_1$-$C_6$ alkylamino, $C_2$-$C_8$ dialkylamino, $C_3$-$C_6$ cycloalkylamino, $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl, hydroxy, NH$_2$, CN or NO$_2$; or $Q^2$;

each $R^8$ is independently halogen, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, $C_2$-$C_4$ alkoxycarbonyl, CN or NO$_2$;

each $R^9$ is independently halogen, $C_1$-$C_6$ alkyl, $C_1$-$C_6$ haloalkyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_1$-$C_6$ alkylamino, $C_2$-$C_6$ dialkylamino, —CN, —NO$_2$, phenyl or pyridinyl;

$R^{10}$ is H; or $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl or $C_4$-$C_7$ cycloalkylalkyl, each optionally substituted with one of more halogen;

$R^{11}$ is H, $C_1$-$C_6$ alkyl, $C_2$-$C_6$ alkenyl, $C_2$-$C_6$ alkynyl, $C_3$-$C_6$ cycloalkyl, $C_4$-$C_7$ alkylcycloalkyl, $C_4$-$C_7$ cycloalkylalkyl, $C_2$-$C_7$ alkylcarbonyl or $C_2$-$C_7$ alkoxycarbonyl;

$R^{12}$ is H; $Q^3$; or $C_1$-$C_6$ alkyl, $C_2$-$C_6$ alkynyl, $C_3$-$C_6$ cycloalkyl, $C_4$-$C_7$ alkylcycloalkyl or C$_4$-C$_7$ cycloalkylalkyl, each optionally substituted with one or more substituents independently selected from R$^7$; or R$^{11}$ and R$^{12}$ are taken together with the nitrogen to which they are attached to form a ring containing 2 to 6 atoms of carbon and optionally one additional atom selected from the group consisting of N, S and O, said ring optionally substituted with 1 to 4 substituents independently selected from the group consisting of C$_1$-C$_2$ alkyl, halogen, —CN, —NO$_2$ and C$_1$-C$_2$ alkoxy; Q$^1$ is a phenyl ring, a 5- or 6-membered heterocyclic ring, or an 8-, 9- or 10-membered fused bicyclic ring system optionally containing one to three heteroatoms selected from up to 1O, up to 1 S and up to 3 N, each ring or ring system optionally substituted with one or more substituents independently selected from R$^8$;

each Q$^2$ is independently a phenyl ring or a 5- or 6-membered heterocyclic ring, each ring optionally substituted with one or more substituents independently selected from R$^9$; Q$^3$ is a phenyl ring or a 5- or 6-membered heterocyclic ring, each ring optionally substituted with one or more substituents independently selected from R$^9$; and n is 0, 1 or 2; or a pharmaceutically acceptable salt thereof; and/or ii) an isoxazoline compound of formula (II):

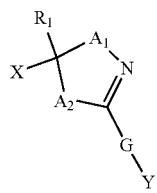

(II)

wherein:

R$_1$ is alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, R$_7$S(O)—, R$_7$S(O)$_2$—, R$_7$C(O)—, R$_7$R$_8$NC(O)—, R$_7$OC(O)—, R$_7$C(O)O—, R$_7$C(O)NR$_8$—, —CN or —NO$_2$;

X is aryl or heteroaryl, which may be unsubstituted or substituted by one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, R$_7$S(O)—, R$_7$S(O)$_2$-R$_7$C(O)—, R$_7$R$_8$NC(O)—, R$_7$OC(O)O—, R$_7$C(O)NR$_8$—, —CN or —NO$_2$;

A$_1$ is oxygen; and

A$_2$ is oxygen, NR$_2$ or CR$_7$R$_8$;

G is G-1 or G-2;

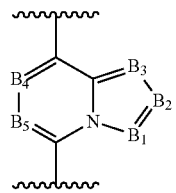

G-1

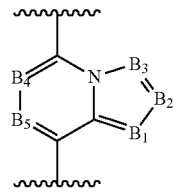

G-2

B$_1$, B$_2$, B$_3$, B$_4$ and B$_5$ are independently N or C—R$_9$;

Y is hydrogen, halogen, —CN; or Y is alkyl, haloalkyl, alkenyl, haloalkenyl, alkynyl, haloalkynyl, cycloalkyl, alkylcycloalkyl, cycloalkylalkyl, aryl, or heterocyclyl or heteroaryl each of which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, R$_7$S(O)—, R$_7$S(O)$_2$—, R$_7$C(O)—, R$_7$R$_8$NC(O)—, R$_7$OC(O)—, R$_7$C(O)O—, R$_7$C(O)NR$_8$—, —CN or —NO$_2$; or Y is Y-1, Y-2, Y-3, Y-4, Y-5, Y-6, Y-7, Y-8, Y-9, Y-10, Y-11, Y-12 or Y-13;

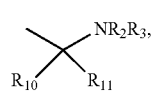

Y-1

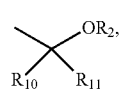

Y-2

Y-3

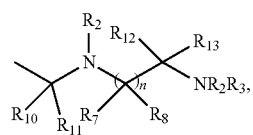

Y-4

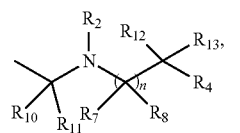

Y-5

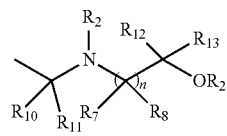

Y-6

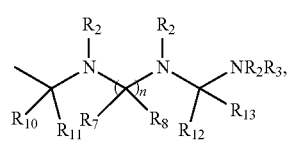

Y-7

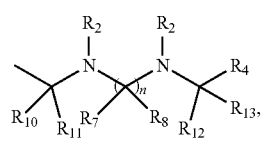

Y-8

-continued

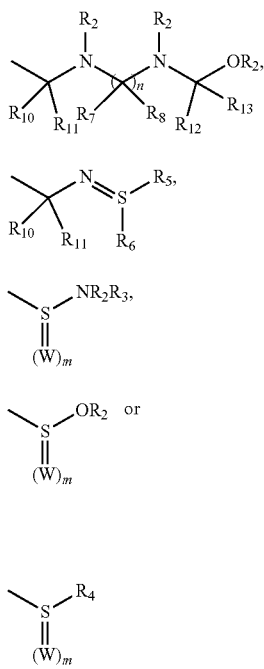

Y-9

Y-10

Y-11

Y-12

Y-13

- $R_2$, $R_3$ are independently hydrogen, alkyl, haloalkyl, thioalkyl, alkylthioalkyl, hydroxyalkyl, alkoxyalkyl, alkenyl, haloalkenyl, alkynyl, haloalkynyl, cycloalkyl, $R_{10}S(O)$—, $R_{10}S(O)_2$—, $R_{10}C(O)$—, $R_{10}C(S)$—, $R_{10}R_{11}NC(O)$—, $R_{10}R_{11}NC(S)$— $R_{10}OC(O)$—; $R_4$, $R_5$ and $R_6$ are independently hydrogen, alkyl, haloalkyl, thioalkyl, alkylthioalkyl, hydroxyalkyl, alkoxyalkyl, alkenyl, haloalkenyl, alkynyl, haloalkynyl, cycloalkyl, aryl or heteroaryl;
- $R_7$ and $R_8$ are independently hydrogen, alkyl, haloalkyl, thioalkyl, alkylthioalkyl, hydroxyalkyl, alkoxyalkyl, alkenyl, haloalkenyl, alkynyl or haloalkynyl;
- $R_9$ is hydrogen, halogen, —CN, or alkyl, haloalkyl, alkenyl, haloalkenyl, alkynyl, haloalkynyl, cycloalkyl, halocycloalkyl, alkylcycloalkyl or cycloalkylalkyl, each which is unsubstituted or substituted with one or more of halogen, hydroxy, amino, alkyl- or di(alkyl)amino, alkyl, cycloalkyl, haloalkyl, alkenyl, haloalkenyl, alkynyl, haloalkynyl, alkoxy, haloalkoxy, alkylthio, haloalkylthio, $R_7S(O)$—, $R_7S(O)_2$—, $R_7C(O)$—, $R_7R_8NC(O)$—, $R_7OC(O)$—, $R_7C(O)O$—, $R_7C(O)NR_8$—, —CN or —NO$_2$;
- $R_{10}$, $R_{11}$, $R_{12}$ and $R_{13}$ are each independently hydrogen, alkyl, haloalkyl, thioalkyl, alkylthioalkyl, hydroxyalkyl, alkoxyalkyl, alkenyl, haloalkenyl, alkynyl or haloalkynyl; or
- $R_{10}$ together with $R_{11}$ form =O, =S or =NR$_2$; or
- $R_{12}$ together with $R_{13}$ form =O, =S or =NR$_2$;
- W is O, S or NR$_2$;
- n is 1-4; and
- m is 0, 1 or 2; or a pharmaceutically acceptable salt thereof; and/or iii) an isoxazoline compound of formula (III)

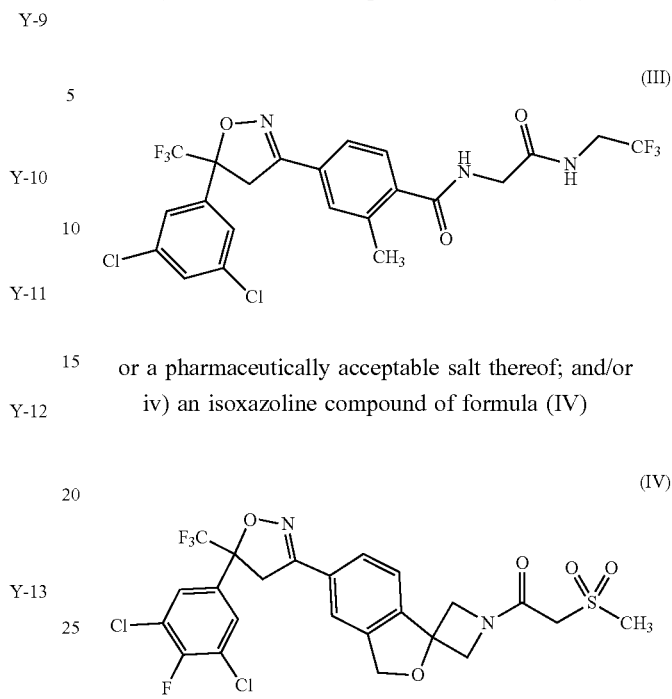

(III)

or a pharmaceutically acceptable salt thereof; and/or iv) an isoxazoline compound of formula (IV)

(IV)

or a pharmaceutically acceptable salt thereof; and/or v) an isoxazoline compound of formula (V):

(V)

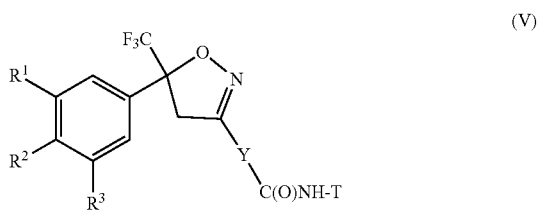

wherein $R^1$, $R^2$ and $R^3$ are independently H, Cl, F or CF$_3$;
Y is the diradical group

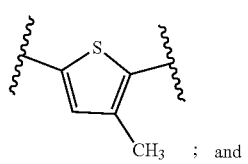

; and

T is a $C_1$-$C_6$-alkyl group which is unsubstituted or substituted by halogen, cyano, nitro, amino, hydroxyl, $C_1$-$C_6$-alkoxy, $C_1$-$C_6$-haloalkoxy, $C_1$-$C_6$-alkylthio, $C_1$-$C_6$-alkylthio, carboxy, carbamoyl or $C_2$-$C_6$-alkanoyl group which may be unsubstituted or substituted in the alkyl portion by halogen or a pharmaceutical acceptable salt thereof; and/or vi) an isoxazoline compound of formula (VI):

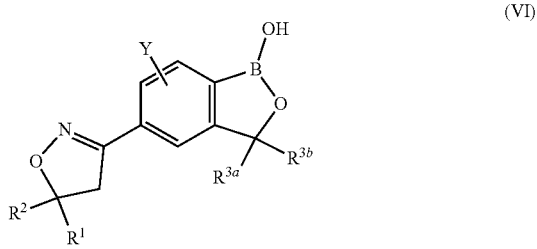

(VI)

wherein Y is hydrogen, fluoro, chloro or bromo;
$R^1$ is phenyl substituted with 2-4 substituents selected from halogen, methyl, difluoromethyl, trifluoromethyl, methoxy, trifluoromethoxy or trifluoroethoxy;
$R^2$ is methyl, fluoromethyl, trifluoromethyl or perfluoroethyl;
$R^{3a}$ and $R^{3b}$ are independently selected from hydrogen, methyl, ethyl or fluoromethyl; or $R^{3a}$ and $R^{3b}$ together combine with the carbon to which they are attached to form a cyclopentyl ring or a cyclohexyl ring; or a pharmaceutically acceptable salt thereof;
b) at least one pharmaceutically acceptable polymer which is a liquid PEG and/or a pharmaceutically acceptable neutral oil;
c) optionally, at least one co-solvent;
d) optionally, an antioxidant; and
e) optionally at least one pharmaceutically acceptable additive, excipient or mixtures thereof;
wherein no other pharmaceutically acceptable polymers are present.

In another embodiment, the present invention provides for a long-acting injectable composition for the treatment and/or prophylaxis of parasitic infections and infestations in or on animals comprising:
a) an antiparasitic effective amount of at least one isoxazoline active agent, which is:
i) an isoxazoline compound of formula (I) as described above, or a pharmaceutically acceptable salt thereof; and/or
ii) an isoxazoline compound of formula (II) as described above, or a pharmaceutically acceptable salt thereof; and/or
iii) an isoxazoline compound of formula (III) as described above, or a pharmaceutically acceptable salt thereof; and/or
iv) an isoxazoline compound of formula (IV) as described above, or a pharmaceutically acceptable salt thereof; and/or
v) an isoxazoline compound of formula (V) as described above, or a pharmaceutically acceptable salt thereof; and/or
vi) an isoxazoline compound of formula (VI) as described above, or a pharmaceutically acceptable salt thereof;
b) at least one pharmaceutically acceptable polymer which is a liquid PEG and/or a pharmaceutically acceptable neutral oil;
c) optionally, at least one co-solvent wherein said co-solvent is a polar solvent miscible with water;
d) optionally, an antioxidant; and
e) optionally at least one pharmaceutically acceptable additive, excipient or mixtures thereof;
wherein no other pharmaceutically acceptable polymers are present.

In another embodiment, the present invention provides for a long-acting injectable composition for the treatment and/or prophylaxis of parasitic infections and infestations in or on animals comprising:
a) an antiparasitic effective amount of at least one isoxazoline active agent, which is:
i) an isoxazoline compound of formula (I) as described above, or a pharmaceutically acceptable salt thereof; and/or
ii) an isoxazoline compound of formula (II) as described above, or a pharmaceutically acceptable salt thereof; and/or
iii) an isoxazoline compound of formula (III) as described above, or a pharmaceutically acceptable salt thereof; and/or
iv) an isoxazoline compound of formula (IV) as described above, or a pharmaceutically acceptable salt thereof; and/or
v) an isoxazoline compound of formula (V) as described above, or a pharmaceutically acceptable salt thereof; and/or
vi) an isoxazoline compound of formula (VI) as described above, or a pharmaceutically acceptable salt thereof;
b) at least one pharmaceutically acceptable polymer which is a liquid PEG and/or a pharmaceutically acceptable neutral oil;
c) optionally, at least one co-solvent wherein said co-solvent is not miscible with water or only partially soluble in water;
d) optionally, an antioxidant; and
e) optionally at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (I) as described above, or a pharmaceutically acceptable salt thereof;
b) at least one pharmaceutically acceptable polymer which is a liquid PEG and/or a pharmaceutically acceptable neutral oil;
c) optionally, at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (I) as described above, or a pharmaceutically acceptable salt thereof;
b) at least one pharmaceutically acceptable polymer which is a liquid PEG and/or a pharmaceutically acceptable neutral oil;
c) optionally, at least one co-solvent, wherein said co-solvent is a polar solvent miscible with water;
d) optionally, an antioxidant; and
e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prophylaxis of parasitic infections and infestations in or on animals comprising:
- a) an antiparasitic effective amount of at least one isoxazoline active agent of formula (I) described above, or a pharmaceutically acceptable salt thereof;
- b) at least one pharmaceutically acceptable polymer which is a liquid PEG and/or a pharmaceutically acceptable neutral oil;
- c) optionally, at least one co-solvent wherein said co-solvent is not miscible with water or only partially soluble in water;
- d) optionally, an antioxidant; and
- e) optionally at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of an isoxazoline compound of formula (Ia):

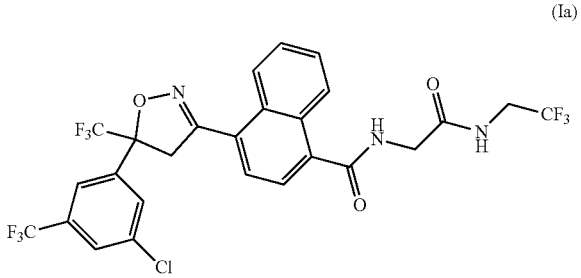 [SMILES: O=C(CNC(=O)c1ccc(C2=NOC(c3cc(Cl)cc(C(F)(F)F)c3)(C(F)(F)F)C2)c2ccccc12)NCC(F)(F)F]

(Ia)

or a pharmaceutically acceptable salt thereof
- b) at least one pharmaceutically acceptable polymer which is a liquid PEG and/or a pharmaceutically acceptable neutral oil;
- c) optionally, at least one co-solvent;
- d) optionally, an antioxidant; and
- e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of at least one isoxazoline compound of formula (Ia) as described above, or a pharmaceutically acceptable salt thereof;
- b) at least one pharmaceutically acceptable polymer which is a liquid PEG and/or a pharmaceutically acceptable neutral oil;
- c) optionally, at least one co-solvent, wherein said co-solvent is a polar solvent miscible with water;
- d) optionally, an antioxidant; and
- e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of at least one isoxazoline compound of formula (Ia) as described above, or a pharmaceutically acceptable salt thereof;
- b) at least one pharmaceutically acceptable polymer which is a liquid PEG and/or a pharmaceutically acceptable neutral oil;
- c) optionally, at least one co-solvent wherein said co-solvent is not miscible with water or only partially soluble in water;
- d) optionally, an antioxidant; and
- e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of at least one isoxazoline compound of formula (Ia) as described above, or a pharmaceutically acceptable salt thereof;
- b) at least one pharmaceutically acceptable polymer which is a liquid PEG;
- c) optionally, a co-solvent, wherein the co-solvent is a $C_1$-$C_6$alcohol, a glycol ether (e.g., including, but limited to, diethyleneglycol monoethyl ether, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), glycerol, propylene glycol, cyclic carbonates (e.g., propylene carbonate), 2-pyrrolidone, N-methylpyrrolidone, dimethyl isosorbide (DMI), dimethylacetamide, dimethylsulfoxide or glycerol formal, or a combination thereof;
- d) optionally, an antioxidant; and
- e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of at least one isoxazoline compound of formula (Ia) as described above, or a pharmaceutically acceptable salt thereof;
- b) at least one pharmaceutically acceptable polymer which is a liquid PEG;
- c) optionally, a co-solvent, wherein the co-solvent is benzyl alcohol, benzyl benzoate, ethyl acetate, triacetin, lipids, $C_8$-$C_{10}$ triglycerides (e.g. MIGLYOL® 810 and MIGLYOL®812), $C_8$-$C_{10}$ triglycerides combined with linoleic acid (e.g. MIGLYOL® 818), $C_8$-$C_{10}$ triglycerides combined with succinic acid (e.g. MIGLYOL® 829), propylene glycol diester of $C_8$-$C_{10}$ fatty acids (e.g. MIGLYOL® 840), castor oil, cottonseed oil, sesame oil, soybean oil and safflower oil, or a combination thereof;
- d) optionally, an antioxidant; and
- e) optionally, a surfactant, and optionally at least one other pharmaceutically acceptable additive, excipient or mixtures thereof;

wherein no other pharmaceutically acceptable polymers are present.

In still another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Ia) as described above, or a pharmaceutically acceptable salt thereof;
b) at least one pharmaceutically acceptable polymer which is a liquid PEG;
c) optionally, a co-solvent, wherein the co-solvent is a $C_1$-$C_6$ alcohol, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Ia) as described above, or a pharmaceutically acceptable salt thereof;
b) at least one pharmaceutically acceptable polymer which is a liquid PEG;
c) optionally, a co-solvent, wherein the co-solvent is ethanol, isopropanol, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Ia) as described above, or a pharmaceutically acceptable salt thereof;
b) at least one pharmaceutically acceptable polymer which is a liquid PEG;
c) optionally, at least one co-solvent wherein said co-solvent is a $C_8$-$C_{10}$ triglyceride, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Ia) as described above, or a pharmaceutically acceptable salt thereof;
b) at least one neutral oil, wherein said neutral oil is a $C_8$-$C_{10}$ triglyceride;
c) optionally, at least one co-solvent wherein said co-solvent is ethanol, isopropanol, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of an isoxazoline compound of formula (Ib):

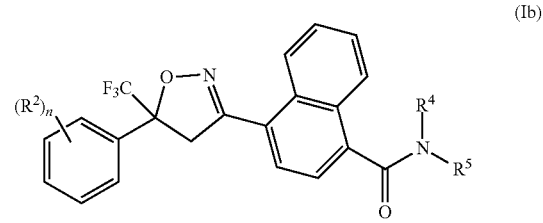

or a pharmaceutically acceptable salt thereof
wherein
$R^2$ independently is halogen, $C_1$-$C_6$ alkyl or $C_1$-$C_6$ haloalkyl
$R^4$ is H or $C_1$-$C_6$ alkyl;
$R^5$ is $C_1$-$C_4$ alkyl optionally substituted with one or more $R^7$; and $R^7$ is $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl (e.g., —$CH_2C(O)NHCH_2CF_3$); and
n is 0, 1 or 2;
b) at least one pharmaceutically acceptable polymer which is a liquid PEG and/or a pharmaceutically acceptable neutral oil;
c) optionally, at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Ib) as described above, or a pharmaceutically acceptable salt thereof;
b) at least one pharmaceutically acceptable polymer which is a liquid PEG and/or a pharmaceutically acceptable neutral oil;
c) optionally, at least one co-solvent, wherein said co-solvent is a polar solvent miscible with water;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:

a) an antiparasitic effective amount of at least one isoxazoline compound of formula (Ib) as described above, or a pharmaceutically acceptable salt thereof;
b) at least one pharmaceutically acceptable polymer which is a liquid PEG and/or a pharmaceutically acceptable neutral oil;
c) optionally, at least one co-solvent, wherein said co-solvent is not miscible with water or only partially soluble in water;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Ib) as described above, or a pharmaceutically acceptable salt thereof;
b) at least one pharmaceutically acceptable polymer which is a liquid PEG and/or a pharmaceutically acceptable neutral oil;
c) optionally, a co-solvent, wherein the co-solvent is a $C_1$-$C_6$alcohol, a glycol ether (e.g., including, but limited to, diethyleneglycol monoethyl ether, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), glycerol, propylene glycol, cyclic carbonates (e.g., propylene carbonate), 2-pyrrolidone, N-methylpyrrolidone, dimethyl isosorbide (DMI), dimethylacetamide, dimethylsulfoxide or glycerol formal, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Ib) as described above, or a pharmaceutically acceptable salt thereof;
b) at least one pharmaceutically acceptable polymer which is a liquid PEG and/or a pharmaceutically acceptable neutral oil;
c) optionally, a co-solvent, wherein the co-solvent is benzyl alcohol, benzyl benzoate, ethyl acetate, triacetin, lipids, $C_8$-$C_{10}$ triglycerides (e.g. MIGLYOL® 810 and MIGLYOL®812), $C_8$-$C_{10}$ triglycerides combined with linoleic acid (e.g. MIGLYOL® 818), $C_8$-$C_{10}$ triglycerides combined with succinic acid (e.g. MIGLYOL® 829), propylene glycol diester of $C_8$-$C_{10}$ fatty acids (e.g. MIGLYOL® 840), castor oil, cottonseed oil, sesame oil, soybean oil and safflower oil, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Ib) as described above, or a pharmaceutically acceptable salt thereof;
b) at least one pharmaceutically acceptable polymer which is a liquid PEG and/or a pharmaceutically acceptable neutral oil;
c) optionally, a co-solvent, wherein the co-solvent is a $C_1$-$C_6$alcohol, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Ib) as described above, or a pharmaceutically acceptable salt thereof;
b) at least one pharmaceutically acceptable polymer which is a liquid PEG and/or a pharmaceutically acceptable neutral oil;
c) optionally, a co-solvent, wherein the co-solvent is ethanol, isopropanol, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Ib) as described above, or a pharmaceutically acceptable salt thereof;
b) at least one pharmaceutically acceptable polymer which is a liquid PEG;
c) optionally, at least one co-solvent wherein said co-solvent is a $C_8$-$C_{10}$ triglyceride, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Ib) as described above, or a pharmaceutically acceptable salt thereof;
b) at least one neutral oil, wherein said neutral oil is a $C_8$-$C_{10}$ triglyceride; c) optionally, at least one co-solvent wherein said co-solvent is ethanol, isopropanol, benzyl alcohol, or a combination thereof;
d) optionally, an antioxidant; and
e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
  a) an antiparasitic effective amount of at least one isoxazoline compound of formula (II) as described above, or a pharmaceutically acceptable salt thereof;
  b) at least one pharmaceutically acceptable polymer which is a liquid PEG and/or a pharmaceutically acceptable neutral oil;
  c) optionally, at least one co-solvent;
  d) optionally, an antioxidant; and
  e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
  a) an antiparasitic effective amount of at least one isoxazoline compound of formula (II) as described above, or a pharmaceutically acceptable salt thereof;
  b) at least one pharmaceutically acceptable polymer which is a liquid PEG and/or a pharmaceutically acceptable neutral oil;
  c) optionally, at least one co-solvent, wherein said co-solvent is a polar solvent miscible with water;
  d) optionally, an antioxidant; and
  e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
  a) an antiparasitic effective amount of at least one isoxazoline compound of formula (II) as described above, or a pharmaceutically acceptable salt thereof;
  b) at least one pharmaceutically acceptable polymer which is a liquid PEG and/or a pharmaceutically acceptable neutral oil;
  c) optionally, at least one co-solvent wherein said co-solvent is not miscible with water or only partially soluble in water;
  d) optionally, an antioxidant; and
  e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
  a) an antiparasitic effective amount of at least one isoxazoline compound of formulae II-1.001 to II-1.025 or II-2.00-II-2.018:

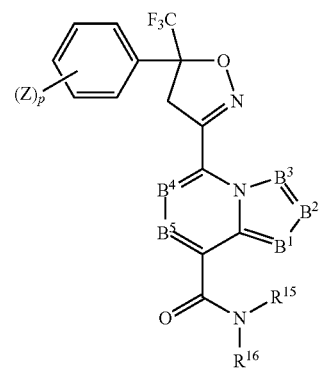

Compounds II-1.001 to II-1.025

| Compound No. | $(Z)_p$ | $B^5$ | $B^4$ | $B^3$ | $B^2$ | $B^1$ | $R^{15}$ | $R^{16}$ |
|---|---|---|---|---|---|---|---|---|
| 1.001 | 3,5-$Cl_2$ | C—H | C—H | C—H | C—H | N | H | $CH_2C(O)NHCH_2CF_3$ |
| 1.002 | 3,5-$Cl_2$ | C—H | C—H | C—H | C—H | N | H | $CH_2CF_3$ |
| 1.003 | 3,5-$(CF_3)_2$ | C—H | C—H | C—H | C—H | N | $CH_3$ | $CH_2CO_2CH_3$ |
| 1.004 | 3,5-$(CF_3)_2$ | C—H | C—H | C—H | C—H | N | $CH_3$ | $CH_2CO_2H$ |
| 1.005 | 3,5-$(CF_3)_2$ | C—H | C—H | C—H | C—H | N | $CH_3$ | $CH_2C(O)NHCH_2CF_3$ |
| 1.006 | 3,5-$(CF_3)_2$ | C—H | C—H | C—H | C—H | N | H | $CH_2C(O)NHCH_2CF_3$ |
| 1.007 | 3,5-$(CF_3)_2$ | C—H | C—H | C—H | C—H | N | H | $CH_2CH_2SCH_3$ |
| 1.008 | 3,5-$(CF_3)_2$ | C—H | C—H | C—H | C—H | C—H | H | $CH_2C(O)NHCH_2CF_3$ |
| 1.009 | 3,5-$(CF_3)_2$ | C—H | C—H | C—H | C—H | C—H | H | $CH_2CH_2SCH_3$ |
| 1.010 | 3,5-$(CF_3)_2$ | C—H | C—H | C—H | C—H | C—H | H | $CH_2CF_3$ |
| 1.011 | 3,5-$Cl_2$ | C—H | C—H | C—H | C—H | C—H | H | $CH_2C(O)NHCH_2CF_3$ |
| 1.012 | 3,5-$Cl_2$ | C—H | C—H | C—H | C—H | C—H | H | $CH_2CF_3$ |
| 1.013 | 3,5-$Cl_2$ | C—H | C—H | C—H | C—H | C—H | H | $CH_2CH_2SCH_3$ |
| 1.014 | 3-Cl,5-$CF_3$ | C—H | C—H | C—H | C—H | C—H | H | $CH_2C(O)NHCH_2CF_3$ |
| 1.015 | 3-Cl,5-$CF_3$ | C—H | C—H | C—H | C—H | C—H | H | $CH_2CF_3$ |
| 1.016 | 3-Cl,5-$CF_3$ | C—H | C—H | C—H | C—H | C—H | H | $CH_2CH_2SCH_3$ |
| 1.017 | 3,5-$Cl_2$ | C—H | C—H | C—Me | C—H | C—Me | H | $CH_2C(O)NHCH_2CF_3$ |
| 1.018 | 3,5-$Cl_2$ | C—H | C—H | C—Me | C—H | C—Me | H | $CH_2CF_3$ |
| 1.019 | 3,5-$Cl_2$ | C—H | C—H | C—Me | C—H | C—Me | H | $CH_2CH_2SCH_3$ |
| 1.020 | 3,5-$(CF_3)_2$ | C—H | C—H | C—Me | C—H | C—Me | H | $CH_2C(O)NHCH_2CF_3$ |
| 1.021 | 3,5-$(CF_3)_2$ | C—H | C—H | C—Me | C—H | C—Me | H | $CH_2CF_3$ |
| 1.022 | 3,5-$(CF_3)_2$ | C—H | C—H | C—Me | C—H | C—Me | H | $CH_2CH_2SCH_3$ |
| 1.023 | 3-Cl,5-$CF_3$ | C—H | C—H | C—Me | C—H | C—Me | H | $CH_2C(O)NHCH_2CF_3$ |

-continued

| Compound No. | (Z)$_p$ | B$^5$ | B$^4$ | B$^3$ | B$^2$ | B$^1$ | R$^{15}$ | R$^{16}$ |
|---|---|---|---|---|---|---|---|---|
| 1.024 | 3-Cl,5-CF$_3$ | C—H | C—H | C—Me | C—H | C—Me | H | CH$_2$CF$_3$ |
| 1.025 | 3-Cl,5-CF$_3$ | C—H | C—H | C—Me | C—H | C—Me | H | CH$_2$CH$_2$SCH$_3$ |

Compounds II-2.001 to II-2.018

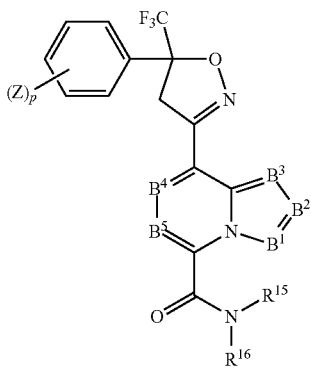

| Compound No. | (Z)$_p$ | B$^5$ | B$^4$ | B$^3$ | B$^2$ | B$^1$ | R$^{15}$ | R$^{16}$ |
|---|---|---|---|---|---|---|---|---|
| 2.001 | 3,5-Cl$_2$ | C—H | C—H | N | C—H | C—H | H | CH$_2$C(O)NHCH$_2$CF$_3$ |
| 2.002 | 3,5-Cl$_2$ | C—H | C—H | N | C—H | C—H | H | CH$_2$CF$_3$ |
| 2.003 | 3,5-Cl$_2$ | C—H | C—H | N | C—H | C—H | H | CH$_2$CH$_2$SCH$_3$ |
| 2.004 | 3,5-(CF$_3$)$_2$ | C—H | C—H | N | C—H | C—H | H | CH$_2$C(O)NHCH$_2$CF$_3$ |
| 2.005 | 3,5-(CF$_3$)$_2$ | C—H | C—H | N | C—H | C—H | H | CH$_2$CF$_3$ |
| 2.006 | 3,5-(CF$_3$)$_2$ | C—H | C—H | N | C—H | C—H | H | CH$_2$CH$_2$SCH$_3$ |
| 2.007 | 3-Cl,5-CF$_3$ | C—H | C—H | N | C—H | C—H | H | CH$_2$C(O)NHCH$_2$CF$_3$ |
| 2.008 | 3-Cl,5-CF$_3$ | C—H | C—H | N | C—H | C—H | H | CH$_2$CF$_3$ |
| 2.009 | 3-Cl,5-CF$_3$ | C—H | C—H | N | C—H | C—H | H | CH$_2$CH$_2$SCH$_3$ |
| 2.010 | 3,5-Cl$_2$ | C—H | C—H | C—H | C—H | C—H | H | CH$_2$C(O)NHCH$_2$CF$_3$ |
| 2.011 | 3,5-Cl$_2$ | C—H | C—H | C—H | C—H | C—H | H | CH$_2$CF$_3$ |
| 2.012 | 3,5-Cl$_2$ | C—H | C—H | C—H | C—H | C—H | H | CH$_2$CH$_2$SCH$_3$ |
| 2.013 | 3,5-(CF$_3$)$_2$ | C—H | C—H | C—H | C—H | C—H | H | CH$_2$C(O)NHCH$_2$CF$_3$ |
| 2.014 | 3,5-(CF$_3$)$_2$ | C—H | C—H | C—H | C—H | C—H | H | CH$_2$CF$_3$ |
| 2.015 | 3,5-(CF$_3$)$_2$ | C—H | C—H | C—H | C—H | C—H | H | CH$_2$CH$_2$SCH$_3$ |
| 2.016 | 3-Cl,5-CF$_3$ | C—H | C—H | C—H | C—H | C—H | H | CH$_2$C(O)NHCH$_2$CF$_3$ |
| 2.017 | 3-Cl,5-CF$_3$ | C—H | C—H | C—H | C—H | C—H | H | CH$_2$CF$_3$ |
| 2.018 | 3-Cl,5-CF$_3$ | C—H | C—H | C—H | C—H | C—H | H | CH$_2$CH$_2$SCH$_3$ | or a pharmaceutically acceptable salt thereof;
b) at least one pharmaceutically acceptable polymer which is a liquid PEG and/or a pharmaceutically acceptable neutral oil;
c) optionally, at least one co-solvent;
d) optionally, an antioxidant; and
e) optionally, at least one pharmaceutically acceptable additive, excipient or mixtures thereof.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formulae II-1.001 to II-1.025 or II-2.00-II-2.018 as described above, or a pharmaceutically acceptable salt thereof;
b) at least one pharmaceutically acceptable polymer which is a liquid PEG and/or a pharmaceutically acceptable neutral oil;

c) optionally, at least one co-solvent, wherein said co-solvent is a polar solvent miscible with water;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formulae II-1.001 to II-1.025 or II-2.00-II-2.018 as described above, or a pharmaceutically acceptable salt thereof;
b) at least one pharmaceutically acceptable polymer which is a liquid PEG and/or a pharmaceutically acceptable neutral oil;
c) optionally, at least one co-solvent wherein said co-solvent is not miscible with water or only partially soluble in water;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of an isoxazoline compound of formula (III)

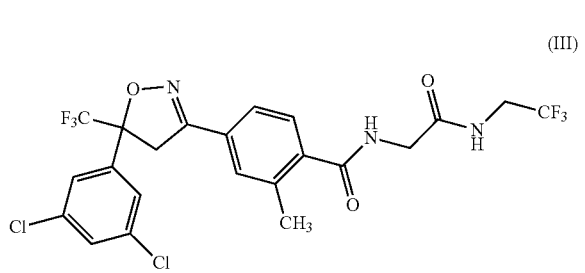 [SMILES: Cc1cc(C2=NOC(c3cc(Cl)cc(Cl)c3)(C(F)(F)F)C2)ccc1C(=O)NCC(=O)NCC(F)(F)F]

or a pharmaceutically acceptable salt thereof;
b) at least one pharmaceutically acceptable polymer which is a liquid PEG and/or a pharmaceutically acceptable neutral oil;
c) optionally at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (III) as described above, or a pharmaceutically acceptable salt thereof;
b) at least one pharmaceutically acceptable polymer which is a liquid PEG and/or a pharmaceutically acceptable neutral oil;
c) optionally, at least one co-solvent, wherein said co-solvent is a polar solvent miscible with water;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (III) as described above, or a pharmaceutically acceptable salt thereof;
b) at least one pharmaceutically acceptable polymer which is a liquid PEG and/or a pharmaceutically acceptable neutral oil;
c) optionally, at least one co-solvent wherein said co-solvent is not miscible with water or only partially soluble in water;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (III) as described above, or a pharmaceutically acceptable salt thereof;
b) at least one pharmaceutically acceptable polymer which is a liquid PEG and/or a pharmaceutically acceptable neutral oil;
c) optionally, a co-solvent, wherein the co-solvent is a $C_1$-$C_6$alcohol, a glycol ether (e.g., including, but limited to, diethyleneglycol monoethyl ether, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), glycerol, propylene glycol, cyclic carbonates (e.g., propylene carbonate), 2-pyrrolidone, N-methylpyrrolidone, dimethyl isosorbide (DMI), dimethylacetamide, dimethylsulfoxide or glycerol formal, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (III) as described above, or a pharmaceutically acceptable salt thereof;
b) at least one pharmaceutically acceptable polymer which is a liquid PEG and/or a pharmaceutically acceptable neutral oil;
c) optionally, a co-solvent, wherein the co-solvent is benzyl alcohol, benzyl benzoate, ethyl acetate, triacetin, lipids, $C_8$-$C_{10}$ triglycerides (e.g. MIGLYOL® 810 and MIGLYOL®812), $C_8$-$C_{10}$ triglycerides combined with linoleic acid (e.g. MIGLYOL® 818), $C_8$-$C_{10}$ triglycerides combined with succinic acid (e.g. MIGLYOL® 829), propylene glycol diester of $C_8$-$C_{10}$ fatty acids (e.g. MIGLYOL® 840), castor oil, cottonseed oil, sesame oil, soybean oil and safflower oil, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (III) as described above, or a pharmaceutically acceptable salt thereof;
b) at least one pharmaceutically acceptable polymer which is a liquid PEG and/or a pharmaceutically acceptable neutral oil;
c) optionally, at least one co-solvent wherein said co-solvent is a $C_1$-$C_6$alcohol, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (III) as described above, or a pharmaceutically acceptable salt thereof;

b) at least one pharmaceutically acceptable polymer which is a liquid PEG and/or a pharmaceutically acceptable neutral oil;
c) optionally, at least one co-solvent wherein said co-solvent is ethanol, isopropanol, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (III) as described above, or a pharmaceutically acceptable salt thereof;
b) at least one pharmaceutically acceptable polymer which is a liquid PEG;
c) optionally, at least one co-solvent wherein said co-solvent is a $C_8$-$C_{10}$ triglyceride, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (III) as described above, or a pharmaceutically acceptable salt thereof;
b) at least one neutral oil, wherein said neutral oil is a $C_8$-$C_{10}$ triglyceride;
c) optionally, at least one co-solvent wherein said co-solvent is ethanol, isopropanol, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
iv) an antiparasitic effective amount of an isoxazoline compound of formula (IV) as described above, or a pharmaceutically acceptable salt thereof;
b) at least one pharmaceutically acceptable polymer which is a liquid PEG and/or a pharmaceutically acceptable neutral oil;
c) optionally at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (IV) as described above, or a pharmaceutically acceptable salt thereof;
b) at least one pharmaceutically acceptable polymer which is a liquid PEG and/or a pharmaceutically acceptable neutral oil;
c) optionally, at least one co-solvent, wherein said co-solvent is a polar solvent miscible with water;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (IV) as described above, or a pharmaceutically acceptable salt thereof;
b) at least one pharmaceutically acceptable polymer which is a liquid PEG and/or a pharmaceutically acceptable neutral oil;
c) optionally, at least one co-solvent wherein said co-solvent is not miscible with water or only partially soluble in water;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (IV) as described above, or a pharmaceutically acceptable salt thereof;
b) at least one pharmaceutically acceptable polymer which is a liquid PEG;
c) optionally, a co-solvent, wherein the co-solvent is a $C_1$-$C_6$ alcohol, a glycol ether (e.g., including, but limited to, diethyleneglycol monoethyl ether, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), glycerol, propylene glycol, cyclic carbonates (e.g., propylene carbonate), 2-pyrrolidone, N-methylpyrrolidone, dimethyl isosorbide (DMI), dimethylacetamide, dimethylsulfoxide or glycerol formal, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (IV) as described above, or a pharmaceutically acceptable salt thereof;
b) at least one pharmaceutically acceptable polymer which is a liquid PEG and/or a pharmaceutically acceptable neutral oil;

c) optionally, a co-solvent, wherein the co-solvent is benzyl alcohol, benzyl benzoate, ethyl acetate, triacetin, lipids, $C_8$-$C_{10}$ triglycerides (e.g. MIGLYOL® 810 and MIGLYOL®812), $C_8$-$C_{10}$ triglycerides combined with linoleic acid (e.g. MIGLYOL® 818), $C_8$-$C_{10}$ triglycerides combined with succinic acid (e.g. MIGLYOL® 829), propylene glycol diester of $C_8$-$C_{10}$ fatty acids (e.g. MIGLYOL® 840), castor oil, cottonseed oil, sesame oil, soybean oil and safflower oil, or a combination thereof;

d) optionally, an antioxidant; and e) optionally, at least one pharmaceutically acceptable additive, excipient or mixtures thereof;

wherein no other pharmaceutically acceptable polymers are present.

In still another embodiment, the present invention provides for a long-acting injectable composition for the treatment and/or prevention (prophylaxis) of parasitic infections and infestations in or on animals comprising:

a) an antiparasitic effective amount of at least one isoxazoline compound of formula (IV) as described above, or a pharmaceutically acceptable salt thereof;

b) at least one pharmaceutically acceptable polymer which is a liquid PEG;

c) optionally, a co-solvent, wherein the co-solvent is a $C_1$-$C_6$alcohol, benzyl alcohol, or a combination thereof;

d) optionally, an antioxidant; and e) optionally, at least one pharmaceutically acceptable additive, excipient or mixtures thereof;

wherein no other pharmaceutically acceptable polymers are present.

In still another embodiment, the present invention provides for a long-acting injectable composition for the treatment and/or prevention (prophylaxis) of parasitic infections and infestations in or on animals comprising:

a) an antiparasitic effective amount of at least one isoxazoline compound of formula (IV) as described above, or a pharmaceutically acceptable salt thereof;

b) at least one pharmaceutically acceptable polymer which is a liquid PEG;

c) optionally, a co-solvent, wherein the co-solvent is ethanol, isopropanol, benzyl alcohol, or a combination thereof;

d) optionally, an antioxidant; and e) optionally, at least one pharmaceutically acceptable additive, excipient or mixtures thereof;

wherein no other pharmaceutically acceptable polymers are present.

In still another embodiment, the present invention provides for a long-acting injectable composition for the treatment and/or prevention (prophylaxis) of parasitic infections and infestations in or on animals comprising:

a) an antiparasitic effective amount of at least one isoxazoline compound of formula (IV) as described above, or a pharmaceutically acceptable salt thereof;

b) at least one pharmaceutically acceptable polymer which is a liquid PEG;

c) optionally, at least one co-solvent wherein said co-solvent is a $C_8$-$C_{10}$ triglyceride, benzyl alcohol, or a combination thereof;

d) optionally, an antioxidant; and e) optionally, at least one pharmaceutically acceptable additive, excipient or mixtures thereof;

wherein no other pharmaceutically acceptable polymers are present.

In still another embodiment, the present invention provides for a long-acting injectable composition for the treatment and/or prevention (prophylaxis) of parasitic infections and infestations in or on animals comprising:

a) an antiparasitic effective amount of at least one isoxazoline compound of formula (IV) as described above, or a pharmaceutically acceptable salt thereof;

b) at least one neutral oil, wherein said neutral oil is a $C_8$-$C_{10}$ triglyceride; c) optionally, at least one co-solvent wherein said co-solvent is ethanol, isopropanol, benzyl alcohol, or a combination thereof;

d) optionally, an antioxidant; and e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:

a) an antiparasitic effective amount of at least one isoxazoline compound of formula (V) as described above, or a pharmaceutically acceptable salt thereof;

b) at least one pharmaceutically acceptable polymer which is a liquid PEG and/or a pharmaceutically acceptable neutral oil;

c) optionally, at least one co-solvent;

d) optionally, an antioxidant; and e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:

a) an antiparasitic effective amount of at least one isoxazoline compound of formula (V) as described above, or a pharmaceutically acceptable salt thereof;

b) at least one pharmaceutically acceptable polymer which is a liquid PEG and/or a pharmaceutically acceptable neutral oil;

c) optionally, at least one co-solvent, wherein said co-solvent is a polar solvent miscible with water;

d) optionally, an antioxidant; and e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:

a) an antiparasitic effective amount of at least one isoxazoline compound of formula (V) as described above, or a pharmaceutically acceptable salt thereof;

b) at least one pharmaceutically acceptable polymer which is a liquid PEG and/or a pharmaceutically acceptable neutral oil;

c) optionally, at least one co-solvent, wherein said co-solvent is not miscible with water or only partially soluble in water;

d) optionally, an antioxidant; and e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising
   a) an antiparasitic effective amount of an isoxazoline compound of formula (Va):

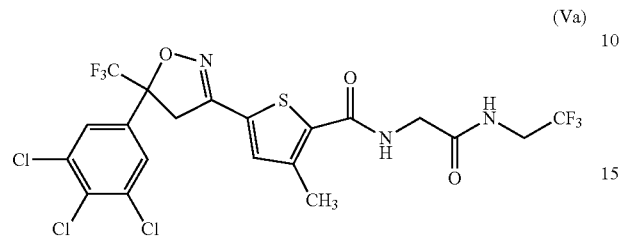

b) at least one pharmaceutically acceptable polymer which is a liquid PEG and/or a pharmaceutically acceptable neutral oil;
   c) optionally, at least one co-solvent;
   d) optionally, an antioxidant; and
   e) optionally, at least one pharmaceutically acceptable additive, excipient or mixtures thereof;
   wherein no other pharmaceutically acceptable polymers are present.

In another embodiment, the present invention provides for a long-acting injectable composition for the treatment and/or prevention (prophylaxis) of parasitic infections and infestations in or on animals comprising:
   a) an antiparasitic effective amount of at least one isoxazoline compound of formula (Va) as described above, or a pharmaceutically acceptable salt thereof;
   b) at least one pharmaceutically acceptable polymer which is a liquid PEG and/or a pharmaceutically acceptable neutral oil;
   c) optionally, at least one co-solvent, wherein said co-solvent is a polar solvent miscible with water;
   d) optionally, an antioxidant; and
   e) optionally, at least one pharmaceutically acceptable additive, excipient or mixtures thereof;
   wherein no other pharmaceutically acceptable polymers are present.

In another embodiment, the present invention provides for a long-acting injectable composition for the treatment and/or prevention (prophylaxis) of parasitic infections and infestations in or on animals comprising:
   a) an antiparasitic effective amount of at least one isoxazoline compound of formula (Va) as described above, or a pharmaceutically acceptable salt thereof;
   b) at least one pharmaceutically acceptable polymer which is a liquid PEG and/or a pharmaceutically acceptable neutral oil;
   c) optionally, at least one co-solvent wherein said co-solvent is not miscible with water or only partially soluble in water;
   d) optionally, an antioxidant; and
   e) optionally, at least one pharmaceutically acceptable additive, excipient or mixtures thereof;
   wherein no other pharmaceutically acceptable polymers are present.

In another embodiment, the present invention provides for a long-acting injectable composition for the treatment and/or prevention (prophylaxis) of parasitic infections and infestations in or on animals comprising:
   a) an antiparasitic effective amount of at least one isoxazoline compound of formula (Va) as described above, or a pharmaceutically acceptable salt thereof;
   b) at least one pharmaceutically acceptable polymer which is a liquid PEG;
   c) optionally, a co-solvent, wherein the co-solvent is a $C_1$-$C_6$alcohol, a glycol ether (e.g., including, but limited to, diethyleneglycol monoethyl ether, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), glycerol, propylene glycol, cyclic carbonates (e.g., propylene carbonate), 2-pyrrolidone, N-methylpyrrolidone, dimethyl isosorbide (DMI), dimethylacetamide, dimethylsulfoxide or glycerol formal, or a combination thereof;
   d) optionally, an antioxidant; and
   e) optionally, at least one pharmaceutically acceptable additive, excipient or mixtures thereof;
   wherein no other pharmaceutically acceptable polymers are present.

In another embodiment, the present invention provides for a long-acting injectable composition for the treatment and/or prevention (prophylaxis) of parasitic infections and infestations in or on animals comprising:
   a) an antiparasitic effective amount of at least one isoxazoline compound of formula (Va) as described above, or a pharmaceutically acceptable salt thereof;
   b) at least one pharmaceutically acceptable polymer which is a liquid PEG and/or a pharmaceutically acceptable neutral oil;
   c) optionally, a co-solvent, wherein the co-solvent is benzyl alcohol, benzyl benzoate, ethyl acetate, triacetin, lipids, $C_8$-$C_{10}$ triglycerides (e.g. MIGLYOL® 810 and MIGLYOL®812), $C_8$-$C_{10}$ triglycerides combined with linoleic acid (e.g. MIGLYOL® 818), $C_8$-$C_{10}$ triglycerides combined with succinic acid (e.g. MIGLYOL® 829), propylene glycol diester of $C_8$-$C_{10}$ fatty acids (e.g. MIGLYOL® 840), castor oil, cottonseed oil, sesame oil, soybean oil and safflower oil, or a combination thereof;
   d) optionally, an antioxidant; and
   e) optionally, at least one pharmaceutically acceptable additive, excipient or mixtures thereof;
wherein no other pharmaceutically acceptable polymers are present.

In still another embodiment, the present invention provides for a long-acting injectable composition for the treatment and/or prevention (prophylaxis) of parasitic infections and infestations in or on animals comprising:
   a) an antiparasitic effective amount of at least one isoxazoline compound of formula (Va) as described above, or a pharmaceutically acceptable salt thereof;
   b) at least one pharmaceutically acceptable polymer which is a liquid PEG;
   c) optionally, a co-solvent, wherein the co-solvent is a $C_1$-$C_6$alcohol, benzyl alcohol, or a combination thereof;
   d) optionally, an antioxidant; and
   e) optionally, at least one pharmaceutically acceptable additive, excipient or mixtures thereof;
wherein no other pharmaceutically acceptable polymers are present.

In still another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Va) as described above, or a pharmaceutically acceptable salt thereof;
b) at least one pharmaceutically acceptable polymer which is a liquid PEG;
c) optionally, a co-solvent, wherein the co-solvent is ethanol, isopropanol, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In still another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Va) as described above, or a pharmaceutically acceptable salt thereof;
b) at least one pharmaceutically acceptable polymer which is a liquid PEG;
c) optionally, at least one co-solvent wherein said co-solvent is a $C_8$-$C_{10}$ triglyceride, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In still another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Va) as described above, or a pharmaceutically acceptable salt thereof;
b) at least one neutral oil, wherein said neutral oil is a $C_8$-$C_{10}$ triglyceride; c) optionally, at least one co-solvent wherein said co-solvent is ethanol, isopropanol, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising
a) an antiparasitic effective amount of at least one compound of formula (VI) as described above, or a pharmaceutically acceptable salt thereof;
b) at least one pharmaceutically acceptable polymer which is a liquid PEG and/or a pharmaceutically acceptable neutral oil;
c) optionally, at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (VI) as described above, or a pharmaceutically acceptable salt thereof;
b) at least one pharmaceutically acceptable polymer which is a liquid PEG and/or a pharmaceutically acceptable neutral oil;
c) optionally, at least one co-solvent, wherein said co-solvent is a polar solvent miscible with water;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (VI) as described above, or a pharmaceutically acceptable salt thereof;
b) at least one pharmaceutically acceptable polymer which is a liquid PEG and/or a pharmaceutically acceptable neutral oil;
c) optionally, at least one co-solvent wherein said co-solvent is not miscible with water or only partially soluble in water;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one compound of formula (VIa):

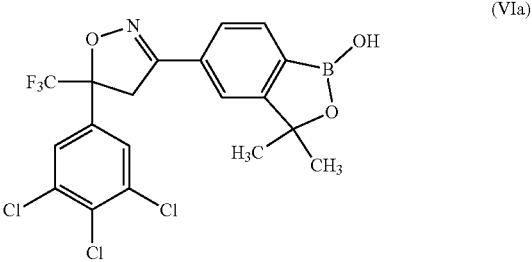 [SMILES: CC1(C)OB(O)c2ccc(C3=NOC(c4cc(Cl)c(Cl)c(Cl)c4)(C(F)(F)F)C3)cc21]

or a pharmaceutically acceptable salt thereof;
b) at least one pharmaceutically acceptable polymer which is a liquid PEG and/or a pharmaceutically acceptable neutral oil;
c) optionally, at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:

a) an antiparasitic effective amount of at least one isoxazoline compound of formula (VIa) as described above, or a pharmaceutically acceptable salt thereof;
b) at least one pharmaceutically acceptable polymer which is a liquid PEG and/or a pharmaceutically acceptable neutral oil;
c) optionally, at least one co-solvent, wherein said co-solvent is a polar solvent miscible with water;
d) optionally, an antioxidant; and
e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (VIa) as described above, or a pharmaceutically acceptable salt thereof;
b) at least one pharmaceutically acceptable polymer which is a liquid PEG and/or a pharmaceutically acceptable neutral oil;
c) optionally, at least one co-solvent wherein said co-solvent is not miscible with water or only partially soluble in water;
d) optionally, an antioxidant; and
e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (VIa) as described above, or a pharmaceutically acceptable salt thereof;
b) at least one pharmaceutically acceptable polymer which is a liquid PEG;
c) optionally, a co-solvent, wherein the co-solvent is a $C_1$-$C_6$alcohol, a glycol ether (e.g., including, but limited to, diethyleneglycol monoethyl ether, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), glycerol, propylene glycol, cyclic carbonates (e.g., propylene carbonate), 2-pyrrolidone, N-methylpyrrolidone, dimethyl isosorbide (DMI), dimethylacetamide, dimethylsulfoxide or glycerol formal, or a combination thereof;
d) optionally, an antioxidant; and
e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (VIa) as described above, or a pharmaceutically acceptable salt thereof;
b) at least one pharmaceutically acceptable polymer which is a liquid PEG and/or a pharmaceutically acceptable neutral oil;
c) optionally, a co-solvent, wherein the co-solvent is benzyl alcohol, benzyl benzoate, ethyl acetate, triacetin, lipids, $C_8$-$C_{10}$ triglycerides (e.g. MIGLYOL® 810 and MIGLYOL®812), $C_8$-$C_{10}$ triglycerides combined with linoleic acid (e.g. MIGLYOL® 818), $C_8$-$C_{10}$ triglycerides combined with succinic acid (e.g. MIGLYOL® 829), propylene glycol diester of $C_8$-$C_{10}$ fatty acids (e.g. MIGLYOL® 840), castor oil, cottonseed oil, sesame oil, soybean oil and safflower oil, or a combination thereof;
d) optionally, an antioxidant; and
e) optionally, at least one pharmaceutically acceptable additive, excipient or mixtures thereof;

wherein no other pharmaceutically acceptable polymers are present.

In still another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (VIa) as described above, or a pharmaceutically acceptable salt thereof;
b) at least one pharmaceutically acceptable polymer which is a liquid PEG;
c) optionally, a co-solvent, wherein the co-solvent is a $C_1$-$C_6$alcohol, benzyl alcohol, or a combination thereof;
d) optionally, an antioxidant; and
e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (VIa) as described above, or a pharmaceutically acceptable salt thereof;
b) at least one pharmaceutically acceptable polymer which is a liquid PEG and/or a pharmaceutically acceptable neutral oil;
c) optionally, at least one co-solvent wherein said co-solvent is ethanol, isopropanol, benzyl alcohol, or a combination thereof;
d) optionally, an antioxidant; and
e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (VIa) as described above, or a pharmaceutically acceptable salt thereof;
b) at least one pharmaceutically acceptable polymer which is a liquid PEG;
c) optionally, at least one co-solvent wherein said co-solvent is a $C_8$-$C_{10}$ triglyceride, benzyl alcohol, or a combination thereof;
d) optionally, an antioxidant; and
e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (VIa) as described above, or a pharmaceutically acceptable salt thereof;
b) at least one neutral oil, wherein said neutral oil is a $C_8$-$C_{10}$ triglyceride;
c) optionally, at least one co-solvent wherein said co-solvent is ethanol, isopropanol, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the long-acting injectable compositions of present invention comprise an antiparasitic effective amount of at least one isoxazoline of formula (Ib), which has the formula:

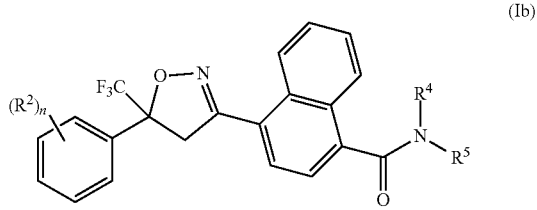

(Ib)

or a pharmaceutically acceptable salt thereof
wherein
$R^2$ independently is halogen, $C_1$-$C_6$ alkyl or $C_1$-$C_6$ haloalkyl
$R^4$ is H or $C_1$-$C_6$ alkyl;
$R^5$ is $C_1$-$C_4$ alkyl optionally substituted with one or more $R^7$; and $R^7$ is $C_2$-$C_7$ alkylcarbonyl, $C_2$-$C_7$ alkoxycarbonyl, $C_2$-$C_7$ alkylaminocarbonyl, $C_3$-$C_9$ dialkylaminocarbonyl, $C_2$-$C_7$ haloalkylcarbonyl, $C_2$-$C_7$ haloalkoxycarbonyl, $C_2$-$C_7$ haloalkylaminocarbonyl, $C_3$-$C_9$ dihaloalkylaminocarbonyl (e.g., —$CH_2C(O)NHCH_2CF_3$); and
n is 0, 1 or 2.

In another embodiment, the present invention provides for a long-acting injectable composition for the treatment and/or prevention (prophylaxis) of parasitic infections and infestations in or on animals comprising:
a) an antiparasitic effective amount of an isoxazoline compound of formula (Ic):

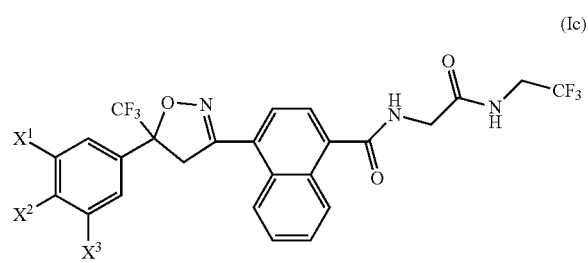

(Ic)

or a pharmaceutically acceptable salt thereof
wherein
$X^1$, $X^2$ and $X^3$ are each independently H, halogen, $C_1$-$C_3$alkyl or $C_1$-$C_3$haloalkyl;

b) at least one pharmaceutically acceptable polymer which is a liquid PEG and/or a pharmaceutically acceptable neutral oil;
c) optionally, at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Ic) as described above, or a pharmaceutically acceptable salt thereof;
b) at least one pharmaceutically acceptable polymer which is a liquid PEG and/or a pharmaceutically acceptable neutral oil;
c) optionally, at least one co-solvent, wherein said co-solvent is a polar solvent miscible with water;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of at least one isoxazoline compound of formula (Ic) as described above, or a pharmaceutically acceptable salt thereof;
b) at least one pharmaceutically acceptable polymer which is a liquid PEG and/or a pharmaceutically acceptable neutral oil;
c) optionally, at least one co-solvent wherein said co-solvent is not miscible with water or only partially soluble in water;
d) optionally, an antioxidant; and
e) optionally, at least one pharmaceutically acceptable additive, excipient or mixtures thereof;
wherein no other pharmaceutically acceptable polymers are present.

In one embodiment, the long-acting injectable compositions of the invention comprise a compound of formula (Ic) wherein $X^1$ and $X^3$ are independently halogen and $X^2$ is hydrogen.

In another embodiment, the long-acting injectable compositions of the invention comprise a compound of formula (Ic), wherein $X^1$, $X^2$ and $X^3$ are each independently halogen.

In another embodiment of the invention, the long-acting injectable compositions comprise a compound of formula (Ic), wherein $X^1$ and $X^3$ are each independently halogen and $X^2$ is $C_1$-$C_3$haloalkyl.

In still another embodiment, the invention provides a long-acting injectable composition comprising a compound of formula (Ic), wherein $X^1$ and $X^2$ are independently halogen and $X^3$ is $C_1$-$C_3$haloalkyl.

In another embodiment, the invention provides a long-acting injectable composition comprising a compound of formula (Ic), wherein $X^1$ and $X^2$ are independently halogen and $X^3$ is $CF_3$.

In another embodiment, the invention provides a long-acting injectable composition comprising a compound of formula (Ic), wherein $X^1$ and $X^3$ are chloro and $X^2$ is hydrogen.

In yet another embodiment, the invention provides a long-acting injectable composition comprising a compound of formula (Ic), wherein $X^1$ is chloro, $X^2$ is fluoro and $X^3$ is $CF_3$.

In another embodiment, the invention provides a long-acting injectable composition comprising a compound of formula (Ic), wherein $X^1$ and $X^3$ are chloro and $X^2$ is fluoro.

In another embodiment, the long-acting injectable compositions of present invention comprise an antiparasitic effective amount of 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound of formula Ia).

In another embodiment, the present invention provides for a long-acting injectable composition for the treatment and/or prevention (prophylaxis) of parasitic infections and infestations in or on animals comprising:
  a) an antiparasitic effective amount of an isoxazoline compound of formula (Ic):

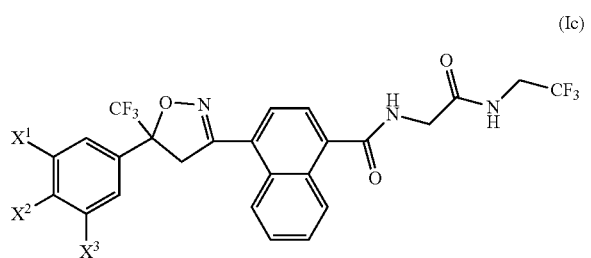

(Ic)

or a pharmaceutically acceptable salt thereof
  wherein
  $X^1$ and $X^3$ are each independently halogen or $C_1$-$C_3$ haloalkyl; and
  $X^2$ is halogen or hydrogen;
  b) at least one pharmaceutically acceptable polymer which is a liquid PEG and/or a pharmaceutically acceptable neutral oil;
  c) optionally, at least one co-solvent;
  d) optionally, an antioxidant; and
  e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
  a) an antiparasitic effective amount of an isoxazoline compound of formula (Ic) shown above, or a pharmaceutically acceptable salt thereof,
  wherein
  $X^1$ and $X^3$ are each independently halogen or $C_1$-$C_3$ haloalkyl; and
  $X^2$ is halogen or hydrogen;
  b) at least one pharmaceutically acceptable polymer which is a liquid PEG and/or a pharmaceutically acceptable neutral oil;
  c) optionally, at least one co-solvent, wherein said co-solvent is a polar solvent miscible with water;
  d) optionally, an antioxidant; and
  e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
  a) an antiparasitic effective amount of at least one isoxazoline compound of formula (Ic) as described above, or a pharmaceutically acceptable salt thereof;
  wherein
  $X^1$ and $X^3$ are each independently halogen or $C_1$-$C_3$ haloalkyl; and
  $X^2$ is halogen or hydrogen;
  b) at least one pharmaceutically acceptable polymer which is a liquid PEG and/or a pharmaceutically acceptable neutral oil;
  c) optionally, at least one co-solvent wherein said co-solvent is not miscible with water or only partially soluble in water;
  d) optionally, an antioxidant; and
  e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
  a) an antiparasitic effective amount of an isoxazoline compound of formula (Ic) as shown above, or a pharmaceutically acceptable salt thereof,
  wherein
  $X^1$ and $X^2$ are each independently chloro or fluoro; and
  $X^3$ is chloro or $CF_3$;
  b) at least one pharmaceutically acceptable polymer which is a liquid PEG and/or a pharmaceutically acceptable neutral oil;
  c) optionally, at least one co-solvent;
  d) optionally, an antioxidant; and
  e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
  a) an antiparasitic effective amount of an isoxazoline compound of formula (Ic) as shown above, or a pharmaceutically acceptable salt thereof,
  wherein
  $X^1$ and $X^2$ are each independently chloro or fluoro; and
  $X^3$ is chloro or $CF_3$;
  b) at least one pharmaceutically acceptable polymer which is a liquid PEG and/or a pharmaceutically acceptable neutral oil;
  c) optionally, at least one co-solvent, wherein said co-solvent is a polar solvent that is miscible with water;
  d) optionally, an antioxidant; and
  e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of at least one isoxazoline compound of formula (Ic) as described above, or a pharmaceutically acceptable salt thereof;
  wherein
  $X^1$ and $X^2$ are each independently chloro or fluoro; and $X^3$ is chloro or $CF_3$;
- b) at least one pharmaceutically acceptable polymer which is a liquid PEG and/or a pharmaceutically acceptable neutral oil;
- c) optionally, at least one co-solvent wherein said co-solvent is not miscible with water or only partially soluble in water;
- d) optionally, an antioxidant; and
- e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of at least one isoxazoline compound of formula (Ic) as described above, or a pharmaceutically acceptable salt thereof;
  wherein
  $X^1$ and $X^2$ are each independently chloro or fluoro; and $X^3$ is chloro or $CF_3$;
- b) at least one pharmaceutically acceptable polymer which is a liquid PEG;
- c) optionally, a co-solvent, wherein the co-solvent is a $C_1$-$C_6$alcohol, a glycol ether (e.g., including, but limited to, diethyleneglycol monoethyl ether, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), glycerol, propylene glycol, cyclic carbonates (e.g., propylene carbonate), 2-pyrrolidone, N-methylpyrrolidone, dimethyl isosorbide (DMI), dimethylacetamide, dimethylsulfoxide or glycerol formal, or a combination thereof;
- d) optionally, an antioxidant; and
- e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of at least one isoxazoline compound of formula (Ic) as described above, or a pharmaceutically acceptable salt thereof;
  wherein
  $X^1$ and $X^2$ are each independently chloro or fluoro; and $X^3$ is chloro or $CF_3$;
- b) at least one pharmaceutically acceptable polymer which is a liquid PEG;
- c) optionally, a co-solvent, wherein the co-solvent is benzyl alcohol, benzyl benzoate, ethyl acetate, triacetin, lipids, $C_8$-$C_{10}$ triglycerides (e.g. MIGLYOL® 810 and MIGLYOL®812), $C_8$-$C_{10}$ triglycerides combined with linoleic acid (e.g. MIGLYOL® 818), $C_8$-$C_{10}$ triglycerides combined with succinic acid (e.g. MIGLYOL® 829), propylene glycol diester of $C_8$-$C_{10}$ fatty acids (e.g. MIGLYOL® 840), castor oil, cottonseed oil, sesame oil, soybean oil and safflower oil, or a combination thereof;
- d) optionally, an antioxidant; and
- e) optionally, at least one surfactant and/or at least one additional pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of at least one isoxazoline compound of formula (Ic) as described above, or a pharmaceutically acceptable salt thereof;
  wherein
  $X^1$ and $X^2$ are each independently chloro or fluoro; and $X^3$ is chloro or $CF_3$;
- b) at least one pharmaceutically acceptable polymer which is a liquid PEG;
- c) optionally, at least one co-solvent wherein said co-solvent is a $C_8$-$C_{10}$ triglyceride, benzyl alcohol, or a combination thereof;
- d) optionally, an antioxidant; and
- e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of at least one isoxazoline compound of formula (Ic) as described above, or a pharmaceutically acceptable salt thereof;
  wherein
  $X^1$ and $X^2$ are each independently chloro or fluoro; and $X^3$ is chloro or $CF_3$;
- b) at least one neutral oil, wherein said neutral oil is a $C_8$-$C_{10}$ triglyceride;
- c) optionally, at least one co-solvent wherein said co-solvent is ethanol, isopropanol, benzyl alcohol, or a combination thereof;
- d) optionally, an antioxidant; and
- e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of an isoxazoline compound of formula (Ic) as shown above, or a pharmaceutically acceptable salt thereof
  wherein
  $X^1$ and $X^3$ are each chloro; and
  $X^2$ is fluoro or hydrogen;
- b) at least one pharmaceutically acceptable polymer which is a liquid PEG and/or a pharmaceutically acceptable neutral oil;
- c) optionally, at least one co-solvent;
- d) optionally, an antioxidant; and
- e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
  a) an antiparasitic effective amount of an isoxazoline compound of formula (Ic) as shown above, or a pharmaceutically acceptable salt thereof,
  wherein
  $X^1$ and $X^3$ are each chloro; and
  $X^2$ is fluoro or hydrogen;
  b) at least one pharmaceutically acceptable polymer which is a liquid PEG and/or a pharmaceutically acceptable neutral oil;
  c) optionally, at least one co-solvent, wherein said co-solvent is a polar solvent that is miscible with water;
  d) optionally, an antioxidant; and
  e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
  a) an antiparasitic effective amount of at least one isoxazoline compound of formula (Ic) as described above, or a pharmaceutically acceptable salt thereof;
  wherein
  $X^1$ and $X^3$ are each chloro; and
  $X^2$ is fluoro or hydrogen;
  b) at least one pharmaceutically acceptable polymer which is a liquid PEG and/or a pharmaceutically acceptable neutral oil;
  c) optionally, at least one co-solvent wherein said co-solvent is not miscible with water or only partially soluble in water;
  d) optionally, an antioxidant; and
  e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
  a) an antiparasitic effective amount of an isoxazoline compound of formula (Ic) as shown above,
  or a pharmaceutically acceptable salt thereof,
  wherein
  $X^1$ is chloro;
  $X^2$ is fluoro; and
  $X^3$ is $CF_3$;
  b) at least one pharmaceutically acceptable polymer which is a liquid PEG and/or a pharmaceutically acceptable neutral oil;
  c) optionally, at least one co-solvent;
  d) optionally, an antioxidant; and
  e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
  a) an antiparasitic effective amount of an isoxazoline compound of formula (Ic) as described above, or a pharmaceutically acceptable salt thereof,
  wherein
  $X^1$ is chloro;
  $X^2$ is fluoro; and
  $X^3$ is $CF_3$;
  b) at least one pharmaceutically acceptable polymer which is a liquid PEG and/or a pharmaceutically acceptable neutral oil;
  c) optionally, at least one co-solvent, wherein said co-solvent is a polar solvent that is miscible with water;
  d) optionally, an antioxidant; and
  e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
  a) an antiparasitic effective amount of at least one isoxazoline compound of formula (Ic) as described above, or a pharmaceutically acceptable salt thereof;
  wherein
  $X^1$ is chloro;
  $X^2$ is fluoro; and
  $X^3$ is $CF_3$;
  b) at least one pharmaceutically acceptable polymer which is a liquid PEG and/or a pharmaceutically acceptable neutral oil;
  c) optionally, at least one co-solvent wherein said co-solvent is not miscible with water or only partially soluble in water;
  d) optionally, an antioxidant; and
  e) optionally, at least one pharmaceutically acceptable additive, excipient or mixtures thereof;
  wherein no other pharmaceutically acceptable polymers are present.

In another embodiment, the present invention provides for a long-acting injectable composition for the treatment and/or prevention (prophylaxis) of parasitic infections and infestations in or on animals comprising:
  a) an antiparasitic effective amount of at least one isoxazoline compound of formula (Ic) as described above, or a pharmaceutically acceptable salt thereof;
  wherein
  $X^1$ is chloro;
  $X^2$ is fluoro; and
  $X^3$ is $CF_3$;
  b) at least one pharmaceutically acceptable polymer which is a liquid PEG and/or a pharmaceutically acceptable neutral oil;
  c) optionally, a co-solvent, wherein the co-solvent is a $C_1$-$C_6$alcohol, a glycol ether (e.g., including, but limited to, diethyleneglycol monoethyl ether, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), glycerol, propylene glycol, cyclic carbonates (e.g., propylene carbonate), 2-pyrrolidone, N-methylpyrrolidone, dimethyl isosorbide (DMI), dimethylacetamide, dimethylsulfoxide or glycerol formal, or a combination thereof;
  d) optionally, an antioxidant; and e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of at least one isoxazoline compound of formula (Ic) as described above, or a pharmaceutically acceptable salt thereof;
  wherein
  $X^1$ is chloro;
  $X^2$ is fluoro; and
  $X^3$ is $CF_3$;
- b) at least one pharmaceutically acceptable polymer which is a liquid PEG;
- c) optionally, a co-solvent, wherein the co-solvent is benzyl alcohol, benzyl benzoate, ethyl acetate, triacetin, lipids, $C_8$-$C_{10}$ triglycerides (e.g. MIGLYOL® 810 and MIGLYOL®812), $C_8$-$C_{10}$ triglycerides combined with linoleic acid (e.g. MIGLYOL® 818), $C_8$-$C_{10}$ triglycerides combined with succinic acid (e.g. MIGLYOL® 829), propylene glycol diester of $C_8$-$C_{10}$ fatty acids (e.g. MIGLYOL® 840), castor oil, cottonseed oil, sesame oil, soybean oil and safflower oil, or a combination thereof;
- d) optionally, an antioxidant; and
- e) optionally, at least one surfactant and optionally at least one additional pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of at least one isoxazoline compound of formula (Ic) as described above, or a pharmaceutically acceptable salt thereof;
  wherein
  $X^1$ is chloro;
  $X^2$ is fluoro; and
  $X^3$ is $CF_3$;
- b) at least one pharmaceutically acceptable polymer which is a liquid PEG and/or a pharmaceutically acceptable neutral oil;
- c) optionally, at least one co-solvent wherein said co-solvent is a $C_1$-$C_6$ alcohol, benzyl alcohol, or a combination thereof;
- d) optionally, an antioxidant; and
- e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of at least one isoxazoline compound of formula (Ic) as described above, or a pharmaceutically acceptable salt thereof;
  wherein
  $X^1$ is chloro;
  $X^2$ is fluoro; and
  $X^3$ is $CF_3$;
- b) at least one pharmaceutically acceptable polymer which is a liquid PEG and/or a pharmaceutically acceptable neutral oil;
- c) optionally, at least one co-solvent wherein said co-solvent is ethanol, isopropanol, benzyl alcohol, or a combination thereof;
- d) optionally, an antioxidant; and
- e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of at least one isoxazoline compound of formula (Ic) as described above, or a pharmaceutically acceptable salt thereof;
  wherein
  $X^1$ is chloro;
  $X^2$ is fluoro; and
  $X^3$ is $CF_3$;
- b) at least one pharmaceutically acceptable polymer which is a liquid PEG;
- c) optionally, at least one co-solvent wherein said co-solvent is a $C_8$-$C_{10}$ triglyceride, benzyl alcohol, or a combination thereof;
- d) optionally, an antioxidant; and
- e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of at least one isoxazoline compound of formula (Ic) as described above, or a pharmaceutically acceptable salt thereof;
  wherein
  $X^1$ is chloro;
  $X^2$ is fluoro; and
  $X^3$ is $CF_3$;
- b) at least one neutral oil, wherein said neutral oil is a $C_8$-$C_{10}$ triglyceride;
- c) optionally, at least one co-solvent wherein said co-solvent is ethanol, isopropanol, benzyl alcohol, or a combination thereof;
- d) optionally, an antioxidant; and
- e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:
- a) an antiparasitic effective amount of an isoxazoline compound of formula (Ic) as shown above, or a pharmaceutically acceptable salt thereof,
  wherein
  $X^1$ and $X^3$ are chloro; and
  $X^2$ is fluoro;
- b) at least one pharmaceutically acceptable polymer which is a liquid PEG and/or a pharmaceutically acceptable neutral oil;
- c) optionally, at least one co-solvent;

d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of an isoxazoline compound of formula (Ic) as described above, or a pharmaceutically acceptable salt thereof;
wherein
$X^1$ and $X^3$ are chloro; and
$X^2$ is fluoro;
b) at least one pharmaceutically acceptable polymer which is a liquid PEG and/or a pharmaceutically acceptable neutral oil;
c) optionally, at least one co-solvent, wherein said co-solvent is a polar solvent that is miscible with water;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of an isoxazoline compound of formula (Ic) as described above, or a pharmaceutically acceptable salt thereof
wherein
$X^1$ and $X^3$ are chloro; and
$X^2$ is fluoro;
b) at least one pharmaceutically acceptable polymer which is a liquid PEG and/or a pharmaceutically acceptable neutral oil;
c) optionally, at least one co-solvent wherein said co-solvent is not miscible with water or only partially soluble in water;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of an isoxazoline compound of formula (Ic) as described above, or a pharmaceutically acceptable salt thereof
wherein
$X^1$ and $X^3$ are chloro; and
$X^2$ is fluoro;
b) at least one pharmaceutically acceptable polymer which is a liquid PEG and/or a pharmaceutically acceptable neutral oil;
c) optionally, a co-solvent, wherein the co-solvent is a $C_1$-$C_6$ alcohol, a glycol ether (e.g., including, but limited to, diethyleneglycol monoethyl ether, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), glycerol, propylene glycol, cyclic carbonates (e.g., propylene carbonate), 2-pyrrolidone, N-methylpyrrolidone, dimethyl isosorbide (DMI), dimethylacetamide, dimethylsulfoxide or glycerol formal, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of an isoxazoline compound of formula (Ic) as described above, or a pharmaceutically acceptable salt thereof
wherein
$X^1$ and $X^3$ are chloro; and
$X^2$ is fluoro;
b) at least one pharmaceutically acceptable polymer which is a liquid PEG;
c) optionally, a co-solvent, wherein the co-solvent is benzyl alcohol, benzyl benzoate, ethyl acetate, triacetin, lipids, $C_8$-$C_{10}$ triglycerides (e.g. MIGLYOL® 810 and MIGLYOL®812), $C_8$-$C_{10}$ triglycerides combined with linoleic acid (e.g. MIGLYOL® 818), $C_8$-$C_{10}$ triglycerides combined with succinic acid (e.g. MIGLYOL® 829), propylene glycol diester of $C_8$-$C_{10}$ fatty acids (e.g. MIGLYOL® 840), castor oil, cottonseed oil, sesame oil, soybean oil and safflower oil, or a combination thereof;
d) optionally, an antioxidant; and
e) optionally, at least one surfactant, and optionally at least one additional pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of an isoxazoline compound of formula (Ic) as described above, or a pharmaceutically acceptable salt thereof
wherein
$X^1$ and $X^3$ are chloro; and
$X^2$ is fluoro;
b) at least one pharmaceutically acceptable polymer which is a liquid PEG;
c) optionally, at least one co-solvent wherein said co-solvent is a $C_8$-$C_{10}$ triglyceride, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of an isoxazoline compound of formula (Ic) as described above, or a pharmaceutically acceptable salt thereof
wherein
$X^1$ and $X^3$ are chloro; and
$X^2$ is fluoro;

b) at least one neutral oil, wherein said neutral oil is a $C_8$-$C_{10}$ triglyceride;

c) optionally, at least one co-solvent wherein said co-solvent is ethanol, isopropanol, benzyl alcohol, or a combination thereof;

d) optionally, an antioxidant; and e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:

a) an antiparasitic effective amount of an isoxazoline compound of formula (Ic) as shown above, or a pharmaceutically acceptable salt thereof, wherein $X^1$, $X^2$ and $X^3$ are each chloro;

b) at least one pharmaceutically acceptable polymer which is a liquid PEG and/or a pharmaceutically acceptable neutral oil;

c) optionally, at least one co-solvent;

d) optionally, an antioxidant; and e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:

a) an antiparasitic effective amount of an isoxazoline compound of formula (Ic) as described above, or a pharmaceutically acceptable salt thereof wherein $X^1$, $X^2$ and $X^3$ are each chloro;

b) at least one pharmaceutically acceptable polymer which is a liquid PEG and/or a pharmaceutically acceptable neutral oil;

c) optionally, at least one co-solvent, wherein said co-solvent is a polar solvent that is miscible with water;

d) optionally, an antioxidant; and e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:

a) an antiparasitic effective amount of an isoxazoline compound of formula (Ic) as described above, or a pharmaceutically acceptable salt thereof wherein $X^1$, $X^2$ and $X^3$ are each chloro;

b) at least one pharmaceutically acceptable polymer which is a liquid PEG and/or a pharmaceutically acceptable neutral oil;

c) optionally, at least one co-solvent wherein said co-solvent is not miscible with water or only partially soluble in water;

d) optionally, an antioxidant; and e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:

a) an antiparasitic effective amount of an isoxazoline compound of formula (Ic) as described above, or a pharmaceutically acceptable salt thereof wherein $X^1$, $X^2$ and $X^3$ are each chloro;

b) at least one pharmaceutically acceptable polymer which is a liquid PEG and/or a pharmaceutically acceptable neutral oil;

c) optionally, a co-solvent, wherein the co-solvent is a $C_1$-$C_6$alcohol, a glycol ether (e.g., including, but limited to, diethyleneglycol monoethyl ether, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), glycerol, propylene glycol, cyclic carbonates (e.g., propylene carbonate), 2-pyrrolidone, N-methylpyrrolidone, dimethyl isosorbide (DMI), dimethylacetamide, dimethylsulfoxide or glycerol formal, or a combination thereof;

d) optionally, an antioxidant; and e) optionally, at least one pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:

a) an antiparasitic effective amount of an isoxazoline compound of formula (Ic) as described above, or a pharmaceutically acceptable salt thereof wherein $X^1$, $X^2$ and $X^3$ are each chloro;

b) at least one pharmaceutically acceptable polymer which is a liquid PEG;

c) optionally, a co-solvent, wherein the co-solvent is benzyl alcohol, benzyl benzoate, ethyl acetate, triacetin, lipids, $C_8$-$C_{10}$ triglycerides (e.g. MIGLYOL® 810 and MIGLYOL®812), $C_8$-$C_{10}$ triglycerides combined with linoleic acid (e.g. MIGLYOL® 818), $C_8$-$C_{10}$ triglycerides combined with succinic acid (e.g. MIGLYOL® 829), propylene glycol diester of $C_8$-$C_{10}$ fatty acids (e.g. MIGLYOL® 840), castor oil, cottonseed oil, sesame oil, soybean oil and safflower oil, or a combination thereof;

d) optionally, an antioxidant; and e) optionally, at least one surfactant, and optionally at least one additional pharmaceutically acceptable additive, excipient or mixtures thereof;

wherein no other pharmaceutically acceptable polymers are present.

In another embodiment, the present invention provides for a long-acting injectable composition for the treatment and/or prevention (prophylaxis) of parasitic infections and infestations in or on animals comprising:

a) an antiparasitic effective amount of an isoxazoline compound of formula (Ic) as described above, or a pharmaceutically acceptable salt thereof wherein
X¹, X² and X³ are each chloro;
b) at least one pharmaceutically acceptable polymer which is a liquid PEG and/or a neutral oil;
c) optionally, a co-solvent, wherein the co-solvent is a $C_1$-$C_6$alcohol, benzyl alcohol, or a combination thereof;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of an isoxazoline compound of formula (Ic) as shown above, or a pharmaceutically acceptable salt thereof,
wherein
X¹, X² and X³ are each independently chloro or fluoro;
b) at least one pharmaceutically acceptable polymer which is a liquid PEG and/or a pharmaceutically acceptable neutral oil;
c) optionally, at least one co-solvent;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of an isoxazoline compound of formula (Ic) as described above, or a pharmaceutically acceptable salt thereof
wherein
X¹, X² and X³ are each independently chloro or fluoro;
b) at least one pharmaceutically acceptable polymer which is a liquid PEG and/or a pharmaceutically acceptable neutral oil;
c) optionally, at least one co-solvent, wherein said co-solvent is a polar solvent that is miscible with water;
d) optionally, an antioxidant; and
e) optionally, at least one pharmaceutically acceptable additive, excipient or mixtures thereof;
wherein no other pharmaceutically acceptable polymers are present.

In another embodiment, the present invention provides for a long-acting injectable composition for the treatment and/or prevention (prophylaxis) of parasitic infections and infestations in or on animals comprising:
a) an antiparasitic effective amount of an isoxazoline compound of formula (Ic) as described above, or a pharmaceutically acceptable salt thereof
wherein
X¹, X² and X³ are each independently chloro or fluoro;
b) at least one pharmaceutically acceptable polymer which is a liquid PEG and/or a pharmaceutically acceptable neutral oil;
c) optionally, at least one co-solvent wherein said co-solvent is not miscible with water or only partially soluble in water;
d) optionally, an antioxidant; and
e) optionally, at least one pharmaceutically acceptable additive, excipient or mixtures thereof;
wherein no other pharmaceutically acceptable polymers are present.

The compounds of formula (I) through formula (VIa) can exist as stereoisomers, and each individual stereoisomer present are encompassed by the structural formulas depicted herein. The various stereoisomers include enantiomers, diastereomers and atop isomers. For avoidance of doubt, when an isoxazoline compound (e.g. any of the isoxazoline active agents as described herein) includes two or more stereoisomers (e.g. an (S)- and (R)-enantiomers), the formulae depicted herein that does not explicitly include stereochemical configurations encompasses each of the possible stereoisomers. One of skill in the art will understand that one stereoisomer of an active isoxazoline compound may be more active and/or may exhibit beneficial properties relative to the other enantiomer. In addition, the skilled person in the art knows how to separate, enrich, and/or selectively prepare a stereoisomer of the isoxazoline compounds described herein. The isoxazoline compounds described herein contain a chiral quaternary carbon atom in the five-membered isoxazoline ring (shown by the asterisk (*) in the structures below); therefore, the compounds will contain at least two possible stereoisomers. As an example for the compounds of formula (Ia), the two possible stereoisomers resulting from the quaternary carbon are shown as formulae (S)-Ia and (R)-Ia:

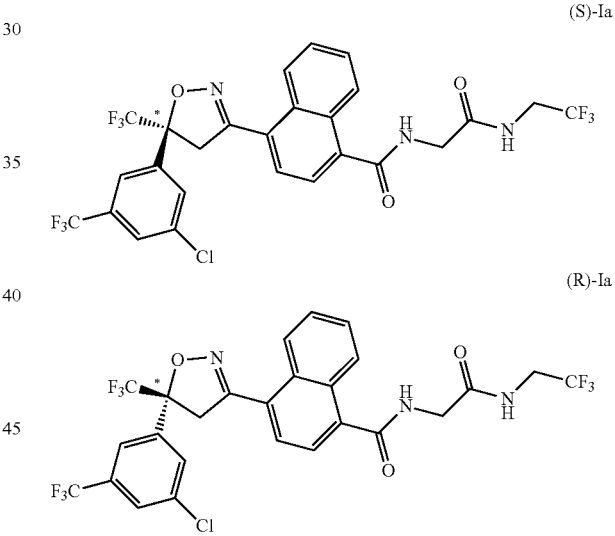

The compound of formula (S)-Ia above has the (S) configuration at the chiral carbon atom and the compound of formula (R)-Ia has the (R) configuration. Molecular depictions drawn herein follow standard conventions for depicting stereochemistry. To indicate stereo configuration, bonds rising from the plane of the drawing and towards the viewer are denoted by solid wedges wherein the broad end of the wedge is attached to the atom rising from the plane of the drawing towards the viewer. Bonds going below the plane of the drawing and away from the viewer are denoted by dashed wedges wherein the narrow end of the wedge is attached to the atom further away from the viewer. Constant width lines indicate bonds with a direction opposite or neutral relative to bonds shown with solid or dashed wedges; constant width lines also depict bonds in molecules or parts of molecules in which no particular stereo configuration is intended to be specified.

In one embodiment of the invention, the more biologically active enantiomer is believed to be formula (S)-Ia. Similarly, the more biologically active enantiomers of isoxazoline compounds of formula (Ib), (Ic) and (II) to (VIa) are believed to have the (S) configuration at the chiral carbon of the isoxazoline ring. In certain embodiments, an isoxazoline compound of the invention, or compositions comprising the compound, are enriched in an enantiomer that displays significant in vitro and in vivo activity (the eutomer) with a favorable toxicity profile relative to a compound or a composition enriched with the other corresponding enantiomer that displays significantly less in vitro and in vivo activity (the distomer).

When enantiomerically enriched, one enantiomer is present in greater amounts than the other, and the extent of enrichment may be defined by an expression of enantiomeric excess ("ee"), which is defined as (2x-1)·100%, where x is the mole fraction of the dominant enantiomer in the mixture (e.g., an ee of 20% corresponds to a 60:40 ratio of enantiomers). In some embodiments, the compositions of the invention comprise compounds that have at least a 50% enantiomeric excess. In other embodiments, the compositions of the invention comprise compounds that have at least a 75% enantiomeric excess, at least a 90% enantiomeric excess, or at least a 94% enantiomeric excess of the more active isomer. Of particular note are enantiomerically pure embodiments of the more active isomer (the eutomer).

Compounds of this invention may also exist as one or more conformational isomers due to restricted rotation about the amide bond bonded to the aryl or heteroaryl ring (e.g. the amide bonded to the naphthyl group in formula (I)). This invention comprises mixtures of conformational isomers. In addition, this invention includes compounds that are enriched in one conformer relative to others.

It will be appreciated that in addition to the compounds of formula (Ia), the other isoxazoline compounds of formula (I), formula (Ib), formula (Ic), formula (II), formula (II-1.1001) to formula (II-1.025), formula (II-2.001) to formula (II-018), formula (III), formula (IV), formula (V), formula (Va), formula (VI) and formula (VIa) will also have at least two possible enantiomers as a result of the quaternary carbon atom on the isoxazoline ring. In addition, certain compounds may include other chiral centers in one or more substituents.

This invention comprises racemic mixtures, for example, equal amounts of the enantiomers of formulae (I) to (VIa). The invention also includes compounds of formula (I), formula (Ia), formula (Ib), formula (Ic), formula (II), formula (II-1.1001) to formula (II-1.025), formula (II-2.001) to formula (II-018), formula (III), formula (IV), formula (V), formula (Va), formula (VI) or formula (VIa), that are enriched in one enantiomer compared to the racemic mixture. Also included are the essentially pure enantiomers of the compounds of formula (I), formula (Ia), formula (Ib), formula (Ic), formula (II), formula (II-1.1001) to formula (II-1.025), formula (II-2.001) to formula (II-018), formula (III), formula (IV), formula (V), formula (Va), formula (VI) or formula (VIa).

Hence, in one embodiment, the long-acting injectable compositions of present invention comprise an antiparasitic effective amount of at least one isoxazoline of formula (I), formula (Ia), formula (Ib), formula (Ic), formula (II), formula (II-1.1001) to formula (II-1.025), formula (II-2.001) to formula (II-018), formula (III), formula (IV), formula (V), formula (Va), formula (VI) or formula (VIa), which is substantially enriched in one enantiomer, or a pharmaceutically acceptable salt thereof. The term "substantially enriched" means that the compound is enriched in a weight:weight ratio of at least about 1.5 or higher in favor of the desired enantiomer. In another embodiment, the long-acting compositions of the invention comprise at least one isoxazoline compound of formula (I), formula (Ia), formula (Ib), formula (Ic), formula (II), formula (II-1.1001) to formula (II-1.025), formula (II-2.001) to formula (II-018), formula (III), formula (IV), formula (V), formula (Va), formula (VI) or formula (VIa) that are enriched in one enantiomer in a weight:weight ratio of at least 2:1, at least 5:1 or at least 10:1. In another embodiment, the compositions comprise at least one compound of formula (I), formula (Ia), formula (Ib), formula (Ic), formula (II), formula (II-1.1001) to formula (II-1.025), formula (II-2.001) to formula (II-018), formula (III), formula (IV), formula (V), formula (Va), formula (VI) or formula (VIa), which is enriched in one enantiomer in a weight:weight ratio of at least 15:1 or at least 20:1, or a pharmaceutically acceptable salt thereof. In an embodiment, the isoxazoline compounds of formula (I), formula (Ia), formula (Ib), formula (Ic), formula (II), formula (II-1.1001) to formula (II-1.025), formula (II-2.001) to formula (II-018), formula (III), formula (IV), formula (V), formula (Va), formula (VI) or formula (VIa) present in the compositions of the invention are essentially pure enantiomers.

In another embodiment of the invention, the compositions comprise a compound of formula (I), formula (Ia), formula (Ib), formula (Ic), formula (II), formula (II-1.1001) to formula (II-1.025), formula (II-2.001) to formula (II-018), formula (III), formula (IV), formula (V), formula (Va), formula (VI) or formula (VIa), that is enriched in the (S)-enantiomer in a weight:weight ratio is at least approximately 1.5:1 or 2:1. In yet another embodiment, the compositions of the invention comprise a compound of formula (I), formula (Ia), formula (Ib), formula (Ic), formula (II), formula (II-1.1001) to formula (II-1.025), formula (II-2.001) to formula (II-018), formula (III), formula (IV), formula (V), formula (Va), formula (VI) or formula (VIa), that is enriched in the (S)-enantiomer in a weight:weight ratio of at least about 5:1 or greater. In still another embodiment, the compositions of the invention comprise a compound of formula (I), formula (Ia), formula (Ib), formula (Ic), formula (II), formula (II-1.1001) to formula (II-1.025), formula (II-2.001) to formula (II-018), formula (III), formula (IV), formula (V), formula (Va), formula (VI) or formula (VIa), that is enriched in the (S)-enantiomer in a weight:weight ratio of at least approximately 10:1, 20:1, or greater. In still another embodiment, the compositions of the invention comprise a compound of formula (I), formula (Ia), formula (Ib), formula (Ic), formula (II), formula (II-1.1001) to formula (II-1.025), formula (II-2.001) to formula (II-018), formula (III), formula (IV), formula (V), formula (Va), formula (VI) or formula (VIa), that is essentially the pure (S)-enantiomer.

In one embodiment, the compositions of the invention comprise a compound of formula (I), (Ia), (Ib) or (Ic) that is substantially enriched in an enantiomer. In another embodiment, the long-acting injectable compositions of the invention comprise a compound of formula (I), (Ia), (Ib) or (Ic) that is substantially enriched in the (S)-enantiomer. In another embodiment, the long-acting injectable compositions of the invention comprise a compound of formula (I), (Ia), (Ib) or (Ic) that is substantially enriched in the (R)-enantiomer.

In another embodiment of the invention, the compositions comprise a compound of formula (I), (Ia), (Ib) or (Ic) that is enriched in the (S)-enantiomer in a weight:weight ratio is at least approximately 1.5:1 or 2:1 or greater. In yet another embodiment, the compositions of the invention comprise a compound of formula (I), (Ia), (Ib) or (Ic) that is enriched in the (S)-enantiomer in a weight:weight ratio of at least about 5:1 or greater. In still another embodiment, the compositions of the invention comprise a compound of formula (I), (Ia), (Ib) or (Ic) that is enriched in the (S)-enantiomer in a weight:weight ratio of at least approximately 10:1, 20:1, or greater. In still another embodiment, the compositions of the invention comprise a compound of formula (I), (Ia), (Ib) or (Ic) that is essentially the pure (S)-enantiomer.

In another embodiment of the invention, the compositions comprise a compound of formula (I), (Ia), (Ib) or (Ic) that is enriched in the (R)-enantiomer in a weight:weight ratio is at least approximately 2:1 or greater. In yet another embodiment, the compositions of the invention comprise a compound of formula (I), (Ia), (Ib) or (Ic) that is enriched in the (R)-enantiomer in a weight:weight ratio of at least about 5:1 or greater. In still another embodiment, the compositions of the invention comprise a compound of formula (I), (Ia), (Ib) or (Ic) that is enriched in the (R)-enantiomer in a weight:weight ratio of at least about 10:1, 20:1, or greater. In still another embodiment, the compositions of the invention comprise a compound of formula (I), (Ia), (Ib) or (Ic) that is essentially the pure (R)-enantiomer.

In another embodiment of the invention, the compositions comprise a compound of formula (II), formula (II-1.1001) to formula (II-1.025), formula (II-2.001) to formula (II-018), formula (III), formula (IV), formula (V), formula (Va), formula (VI) or formula (VIa), that is enriched in the (R)-enantiomer in a weight:weight ratio is at least approximately 2:1 or greater. In yet another embodiment, the compositions of the invention comprise a compound of formula (II), formula (II-1.1001) to formula (II-1.025), formula (II-2.001) to formula (II-018), formula (III), formula (IV), formula (V), formula (Va), formula (VI) or formula (VIa), that is enriched in the (R)-enantiomer in a weight:weight ratio of at least about 5:1 or greater. In still another embodiment, the compositions of the invention comprise a compound of formula (II), formula (II-1.1001) to formula (II-1.025), formula (II-2.001) to formula (II-018), formula (III), formula (IV), formula (V), formula (Va), formula (VI) or formula (VIa), that is enriched in the (R)-enantiomer in a weight:weight ratio of at least approximately 10:1, 20:1, or greater. In still another embodiment, the compositions of the invention comprise a compound of formula (II), formula (II-1.1001) to formula (II-1.025), formula (II-2.001) to formula (II-018), formula (III), formula (IV), formula (V), formula (Va), formula (VI) or formula (VIa), that is essentially the pure (R)-enantiomer.

In another embodiment, the long-acting injectable compositions of present invention comprise an antiparasitic effective amount of at least one isoxazoline disclosed in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 WO 2008/122375, WO 2014/439475 A1 and WO2012 120135A1, all of which are incorporated herein by reference in their entirety.

In yet another embodiment, the long-acting injectable compositions of present invention comprise an antiparasitic effective amount of at least one isoxazoline compound described in WO 2009/02451A2 and WO 2011/075591A1, both incorporated herein by reference in their entirety.

In yet another embodiment, the long-acting injectable compositions of present invention comprise an antiparasitic effective amount of at least one isoxazoline which is compound 11-1 described in WO 2009/02451A2, which has the structure:

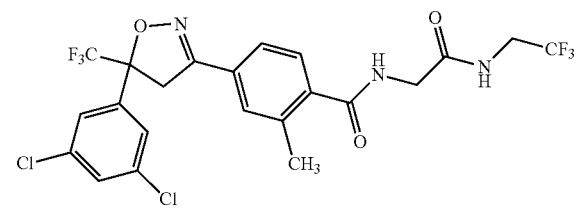 [SMILES: Cc1cc(C2=NOC(c3cc(Cl)cc(Cl)c3)(C(F)(F)F)C2)ccc1C(=O)NCC(=O)NCC(F)(F)F]

In one embodiment, the compositions of the invention may comprise about 0.5 to about 50% (w/v) of an isoxazoline active agent of any of formulae (I), (Ia), (Ic), (II), (III), (IV), (V), (Va), (VI) or (VIa), or a pharmaceutically acceptable salt thereof, either as a racemic mixture or enriched in an enantiomer as described above. In another embodiment, the compositions of the invention may comprise about 1 to about 40% (w/v) of an isoxazoline active agent of any of formulae (I), (Ia), (Ib), (Ic), (II), (III), (IV), (V), (Va), (VI) or (VIa), or a pharmaceutically acceptable salt thereof. In yet another embodiment, the compositions of the invention may comprise about 1 to about 30% (w/v), about 1 to about 20% (w/v) or about 1 to about 15% (w/v) of an isoxazoline active agent of any of formulae (I), (Ia), (Ib), (Ic), (II), (III), (IV), (V), (Va), (VI) or (VIa), or a pharmaceutically acceptable salt thereof. In another embodiment, the compositions of the invention may comprise about 0.5 to about 10% (w/v) or about 0.5% to about 5% (w/v) of an isoxazoline active agent of any of formulae (I), (Ia), (Ib), (Ic), (II), (III), (IV), (V), (Va), (VI) or (VIa), or a pharmaceutically acceptable salt thereof.

In another embodiment, the compositions of the invention may comprise about 5 to about 40% (w/v) or about 5 to about 30% (w/v) of an isoxazoline active agent, or a pharmaceutically acceptable salt thereof. In another embodiment, the compositions may comprise about 10% to about 40% (w/v) of an isoxazoline active agent, or a pharmaceutically acceptable salt thereof. In yet another embodiment, the compositions of the invention may comprise about 15% to about 40% (w/v), about 15% to about 35% (w/v) or about 15% to about 30% (w/v) of an isoxazoline compound, or a pharmaceutically acceptable salt thereof.

In certain embodiments the present invention provides for long-acting injectable compositions for the treatment and/or prevention of parasitic infections and infestations in or on animals comprising:
 a) about 0.5 to 30% (w/v) of an isoxazoline active agent, such as, for example, any of the isoxazoline compounds provided for in the embodiments above (e.g., a compound of any of formula I to VIa described above), or a pharmaceutically acceptable salt thereof;
 b) a pharmaceutically acceptable polymer which is a liquid PEG and/or a pharmaceutically acceptable neutral oil;
 c) optionally, about 1% to 40% (w/v) of co-solvent;
 d) optionally, about 0.01% to about 2.0% (w/v) of an antioxidant; and
 e) optionally about 0.01% to about 5.0% (w/v) of a pharmaceutically acceptable additive, excipient or mixtures thereof;
 wherein the only pharmaceutically acceptable polymer present in said long-acting injectable composition is a liquid PEG and wherein the liquid PEG and/or neutral oil is present in the overall composition in a proportion representing the complement to 100% of the composition.

In another embodiment the present invention provides for long-acting injectable compositions for the treatment and/or prevention of parasitic infections and infestations in or on animals comprising:
- a) about 0.5 to 20% (w/v) of an isoxazoline active agent, such as, for example, any of the isoxazoline compounds provided for in the embodiments above (e.g., a compound of any of formula I to VIa described above), or a pharmaceutically acceptable salt thereof;
- b) pharmaceutically acceptable polymer which is a liquid PEG and/or a pharmaceutically acceptable neutral oil;
- c) optionally, about 1% to 40% (w/v) of co-solvent;
- d) optionally, about 0.01% to about 2.0% (w/v) of an antioxidant; and
- e) optionally about 0.01% to about 5.0% (w/v) of a pharmaceutically acceptable additive, excipient or mixtures thereof;
- wherein the only pharmaceutically acceptable polymer present in said long-acting injectable composition is a liquid PEG and wherein the liquid PEG and/or neutral oil is present in the overall composition in a proportion representing the complement to 100% of the composition.

In certain embodiments the present invention provides for long-acting injectable compositions for the treatment and/or prevention of parasitic infections and infestations in or on animals comprising:
- a) about 5 to 30% (w/v) of an isoxazoline active agent, such as, for example, any of the isoxazoline compounds provided for in the embodiments above (e.g., a compound of any of formula I to VIa described above), or a pharmaceutically acceptable salt thereof;
- b) pharmaceutically acceptable polymer which is a liquid PEG and/or a pharmaceutically acceptable neutral oil;
- c) optionally, about 1% to 40% (w/v) of co-solvent;
- d) optionally, about 0.01% to about 2.0% (w/v) of an antioxidant; and
- e) optionally about 0.01% to about 5.0% (w/v) of a pharmaceutically acceptable additive, excipient or mixtures thereof;
- wherein the only pharmaceutically acceptable polymer present in said long-acting injectable composition is a liquid PEG and wherein the liquid PEG and/or neutral oil is present in the overall composition in a proportion representing the complement to 100% of the composition.

In certain embodiments the present invention provides for long-acting injectable compositions for the treatment and/or prevention of parasitic infections and infestations in or on animals comprising:
- a) about 0.5 to 30% (w/v) of an isoxazoline active agent, such as, for example, any of the isoxazoline compounds provided for in the embodiments above (e.g., a compound of any of formula I to VIa described above), or a pharmaceutically acceptable salt thereof;
- b) a pharmaceutically acceptable polymer which is a liquid PEG and/or a pharmaceutically acceptable neutral oil;
- c) optionally, about 1% to 40% (w/v) of co-solvent, wherein said co-solvent is a polar solvent that is miscible with water;
- d) optionally, about 0.01% to about 2.0% (w/v) of an antioxidant; and
- e) optionally about 0.01% to about 5.0% (w/v) of a pharmaceutically acceptable additive, excipient or mixtures thereof;
- wherein the only pharmaceutically acceptable polymer present in said long-acting injectable composition is a liquid PEG and wherein the liquid PEG and/or neutral oil is present in the overall composition in a proportion representing the complement to 100% of the composition.

In another embodiment the present invention provides for long-acting injectable compositions for the treatment and/or prevention of parasitic infections and infestations in or on animals comprising:
- a) about 0.5 to 20% (w/v) of an isoxazoline active agent, such as, for example, any of the isoxazoline compounds provided for in the embodiments above (e.g., a compound of any of formula I to VIa described above), or a pharmaceutically acceptable salt thereof;
- b) pharmaceutically acceptable polymer which is a liquid PEG and/or a pharmaceutically acceptable neutral oil;
- c) optionally, about 1% to 40% (w/v) of co-solvent, wherein said co-solvent is a polar solvent that is miscible with water;
- d) optionally, about 0.01% to about 2.0% (w/v) of an antioxidant; and
- e) optionally about 0.01% to about 5.0% (w/v) of a pharmaceutically acceptable additive, excipient or mixtures thereof;
- wherein the only pharmaceutically acceptable polymer present in said long-acting injectable composition is a liquid PEG and wherein the liquid PEG and/or neutral oil is present in the overall composition in a proportion representing the complement to 100% of the composition.

In certain embodiments the present invention provides for long-acting injectable compositions for the treatment and/or prevention of parasitic infections and infestations in or on animals comprising:
- a) about 5 to 30% (w/v) of an isoxazoline active agent, such as, for example, any of the isoxazoline compounds provided for in the embodiments above (e.g., a compound of any of formula I to VIa described above), or a pharmaceutically acceptable salt thereof;
- b) pharmaceutically acceptable polymer which is a liquid PEG and/or a pharmaceutically acceptable neutral oil;
- c) optionally, about 1% to 40% (w/v) of co-solvent, wherein said co-solvent is a polar solvent that is miscible with water;
- d) optionally, about 0.01% to about 2.0% (w/v) of an antioxidant; and
- e) optionally about 0.01% to about 5.0% (w/v) of a pharmaceutically acceptable additive, excipient or mixtures thereof;
- wherein the only pharmaceutically acceptable polymer present in said long-acting injectable composition is a liquid PEG and wherein the liquid PEG and/or neutral oil is present in the overall composition in a proportion representing the complement to 100% of the composition.

In certain embodiments the present invention provides for long-acting injectable compositions for the treatment and/or prophylaxis of parasitic infections and infestations in or on animals comprising:
- a) about 0.5 to 30% (w/v) of an isoxazoline active agent of the formula (Ia), (e.g., a compound of formulae I-VIa), such as, a compound of the formula:

(Ia)
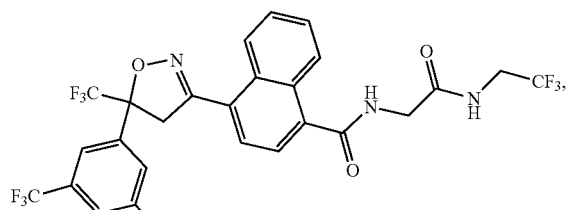
(S)-Ia
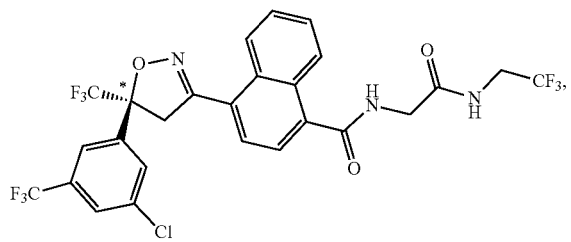
(R)-Ia
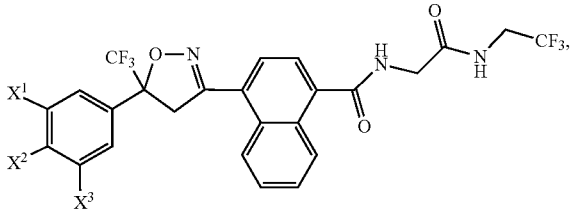
(Ic)
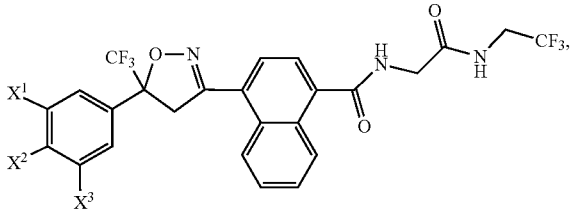
wherein $X^1$, $X^2$ and $X^3$ are independently chloro, fluoro or $CF_3$;
(S)-Ic
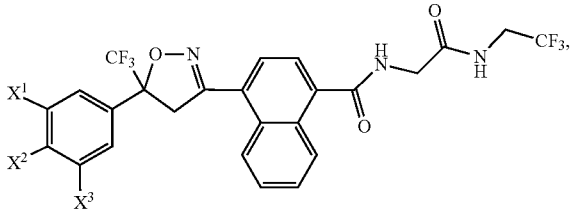
wherein $X^1$, $X^2$ and $X^3$ are independently chloro, fluoro or $CF_3$;
(R)-Ic
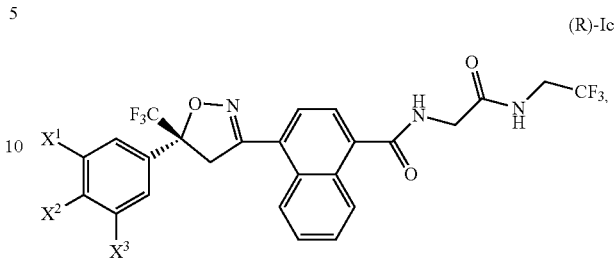
wherein $X^1$, $X^2$ and $X^3$ are independently chloro, fluoro or $CF_3$;
(III)
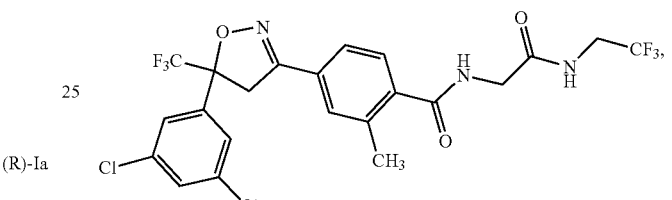
(S)-III
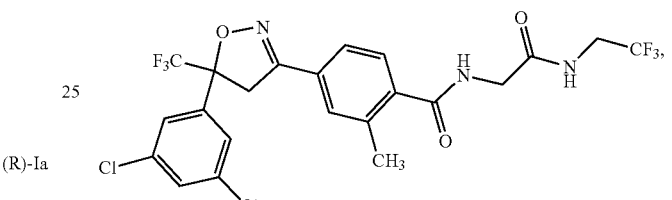
(IV)
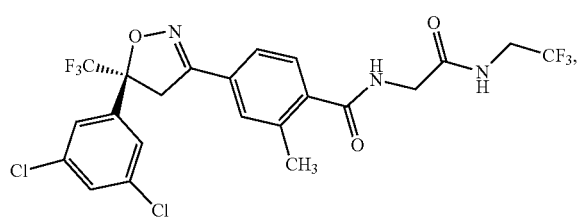
(S)-IV
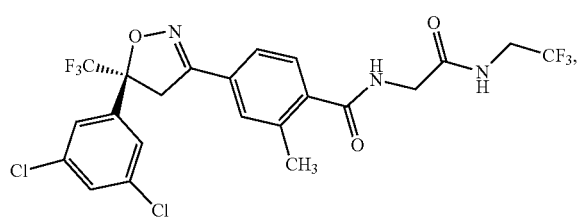
(Va)
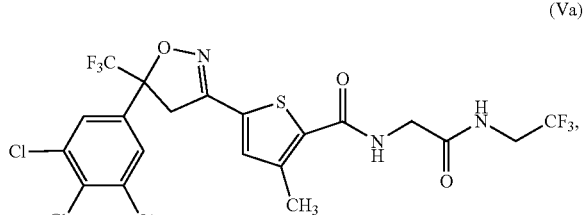

-continued

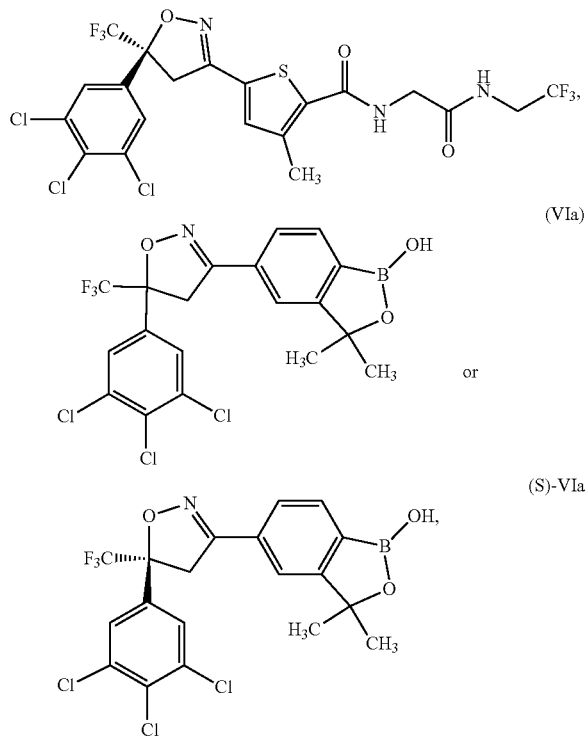

or a pharmaceutically acceptable salt thereof,
b) pharmaceutically acceptable polymer which is a liquid PEG and/or a pharmaceutically acceptable neutral oil;
c) optionally, about 1% to 40% (w/v) of a co-solvent, wherein the co-solvent is a $C_1$-$C_6$alcohol, a glycol ether (e.g., including, but limited to, diethyleneglycol monoethyl ether, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), glycerol, propylene glycol, cyclic carbonates (e.g., propylene carbonate), 2-pyrrolidone, N-methylpyrrolidone, dimethyl isosorbide (DMI), dimethylacetamide, dimethylsulfoxide or glycerol formal, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG and/or neutral oil is present in the overall composition in a proportion representing the complement to 100% of the composition.

In certain embodiments the present invention provides for long-acting injectable compositions for the treatment and/or prophylaxis of parasitic infections and infestations in or on animals comprising:
a) about 0.5 to 20% (w/v) of an isoxazoline active agent of the formula (Ia), (S)-Ia, (R)-Ia, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$; (R)-Ic wherein $X^1$, $X^2$ and $X^3$ are independently chloro, fluoro or $CF_3$; (III), (S)-III, (IV), (S)-IV, (Va), (S)-Va, (VIa) or (S)-VIa as shown above;
or a pharmaceutically acceptable salt thereof,
b) pharmaceutically acceptable polymer which is a liquid PEG and/or a pharmaceutically acceptable neutral oil;
c) optionally, about 1% to 40% (w/v) of co-solvent, wherein the co-solvent is a $C_1$-$C_6$alcohol, a glycol ether (e.g., including, but limited to, diethyleneglycol monoethyl ether, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), glycerol, propylene glycol, cyclic carbonates (e.g., propylene carbonate), 2-pyrrolidone, N-methylpyrrolidone, dimethyl isosorbide (DMI), dimethylacetamide, dimethylsulfoxide or glycerol formal, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG and/or neutral oil is present in the overall composition in a proportion representing the complement to 100% of the composition.

In other embodiments the present invention provides for long-acting injectable compositions for the treatment and/or prophylaxis of parasitic infections and infestations in or on animals comprising:
a) about 1 to 20% (w/v) of an isoxazoline active agent of the formula (Ia), (S)-Ia, (R)-Ia, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$; (R)-Ic wherein $X^1$, $X^2$ and $X^3$ are independently chloro, fluoro or $CF_3$; (III), (S)-III, (IV), (S)-IV, (Va), (S)-Va, (Va) or (S)-VIa as shown above;
or a pharmaceutically acceptable salt thereof,
b) pharmaceutically acceptable polymer which is a liquid PEG and/or a pharmaceutically acceptable neutral oil;
c) optionally, about 1% to 40% (w/v) of co-solvent, wherein the co-solvent is a $C_1$-$C_6$alcohol, a glycol ether (e.g., including, but limited to, diethyleneglycol monoethyl ether, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), glycerol, propylene glycol, cyclic carbonates (e.g., propylene carbonate), 2-pyrrolidone, N-methylpyrrolidone, dimethyl isosorbide (DMI), dimethylacetamide, dimethylsulfoxide or glycerol formal, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG and/or neutral oil is present in the overall composition in a proportion representing the complement to 100% of the composition.

In other embodiments the present invention provides for long-acting injectable compositions for the treatment and/or prophylaxis of parasitic infections and infestations in or on animals comprising:
- a) about 1 to 15% (w/v) of an isoxazoline active agent of the formula (Ia), (S)-Ia, (R)-Ia, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$; (R)-Ic wherein $X^1$, $X^2$ and $X^3$ are independently chloro, fluoro or $CF_3$; (III), (S)-III, (IV), (S)-IV, (Va), (S)-Va, (Va) or (S)-VIa as shown above;
- or a pharmaceutically acceptable salt thereof,
- b) pharmaceutically acceptable polymer which is a liquid PEG and/or a pharmaceutically acceptable neutral oil;
- c) optionally, about 1% to 40% (w/v) of co-solvent, wherein the co-solvent is a $C_1$-$C_6$alcohol, a glycol ether (e.g., including, but limited to, diethyleneglycol monoethyl ether, butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), glycerol, propylene glycol, cyclic carbonates (e.g., propylene carbonate), 2-pyrrolidone, N-methylpyrrolidone, dimethyl isosorbide (DMI), dimethylacetamide, dimethylsulfoxide or glycerol formal, or a combination thereof;
- d) optionally, about 0.01% to about 2.0% (w/v) of an antioxidant; and
- e) optionally about 0.01% to about 5.0% (w/v) of a pharmaceutically acceptable additive, excipient or mixtures thereof;
- wherein the only pharmaceutically acceptable polymer present in said long-acting injectable composition is a liquid PEG and wherein the liquid PEG and/or neutral oil is present in the overall composition in a proportion representing the complement to 100% of the composition.

In certain embodiments the present invention provides for long-acting injectable compositions for the treatment and/or prophylaxis of parasitic infections and infestations in or on animals comprising:
- a) about 0.5 to 30% (w/v) of an isoxazoline active agent of the formula (Ia), (S)-Ia, (R)-Ia, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$; (R)-Ic wherein $X^1$, $X^2$ and $X^3$ are independently chloro, fluoro or $CF_3$; (III), (S)-III, (IV), (S)-IV, (Va), (S)-Va, (Va) or (S)-VIa as shown above, or a pharmaceutically acceptable salt thereof;
- b) pharmaceutically acceptable polymer which is a liquid PEG;
- c) optionally, about 1% to 40% (w/v) of a co-solvent, wherein the co-solvent is benzyl alcohol, benzyl benzoate, ethyl acetate, triacetin, lipids, $C_8$-$C_{10}$ triglycerides (e.g. MIGLYOL® 810 and MIGLYOL®812), $C_8$-$C_{10}$ triglycerides combined with linoleic acid (e.g. MIGLYOL® 818), $C_8$-$C_{10}$ triglycerides combined with succinic acid (e.g. MIGLYOL® 829), propylene glycol diester of $C_8$-$C_{10}$ fatty acids (e.g. MIGLYOL® 840), castor oil, cottonseed oil, sesame oil, soybean oil and safflower oil, or a combination thereof;
- d) optionally, about 0.01% to about 2.0% (w/v) of an antioxidant; and
- e) optionally about 0.01% to about 5.0% (w/v) of a pharmaceutically acceptable additive, excipient or mixtures thereof;
- wherein the only pharmaceutically acceptable polymer present in said long-acting injectable composition is a liquid PEG and wherein the liquid PEG is present in the overall composition in a proportion representing the complement to 100% of the composition.

In certain embodiments the present invention provides for long-acting injectable compositions for the treatment and/or prophylaxis of parasitic infections and infestations in or on animals comprising:
- a) about 0.5 to 20% (w/v) of an isoxazoline active agent of the formula (Ia), (S)-Ia, (R)-Ia, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$; (R)-Ic wherein $X^1$, $X^2$ and $X^3$ are independently chloro, fluoro or $CF_3$; (III), (S)-III, (IV), (S)-IV, (Va), (S)-Va, (Va) or (S)-VIa as shown above;
- or a pharmaceutically acceptable salt thereof,
- b) pharmaceutically acceptable polymer which is a liquid PEG;
- c) optionally, about 5% to 40% (w/v) of co-solvent, wherein the co-solvent is benzyl alcohol, benzyl benzoate, ethyl acetate, triacetin, lipids, $C_8$-$C_{10}$ triglycerides (e.g. MIGLYOL® 810 and MIGLYOL®812), $C_8$-$C_{10}$ triglycerides combined with linoleic acid (e.g. MIGLYOL® 818), $C_8$-$C_{10}$ triglycerides combined with succinic acid (e.g. MIGLYOL® 829), propylene glycol diester of $C_8$-$C_{10}$ fatty acids (e.g. MIGLYOL® 840), castor oil, cottonseed oil, sesame oil, soybean oil and safflower oil, or a combination thereof;
- d) optionally, about 0.01% to about 2.0% (w/v) of an antioxidant; and
- e) optionally about 0.01% to about 5.0% (w/v) of a pharmaceutically acceptable additive, excipient or mixtures thereof;
- wherein the only pharmaceutically acceptable polymer present in said long-acting injectable composition is a liquid PEG and wherein the liquid PEG is present in the overall composition in a proportion representing the complement to 100% of the composition.

In other embodiments the present invention provides for long-acting injectable compositions for the treatment and/or prophylaxis of parasitic infections and infestations in or on animals comprising:
- a) about 1 to 20% (w/v) of an isoxazoline active agent of the formula (Ia), (S)-Ia, (R)-Ia, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$; (R)-Ic wherein $X^1$, $X^2$ and $X^3$ are independently chloro, fluoro or $CF_3$; (III), (S)-III, (IV), (S)-IV, (Va), (S)-Va, (Va) or (S)-VIa as shown above;
- or a pharmaceutically acceptable salt thereof,
- b) pharmaceutically acceptable polymer which is a liquid PEG;
- c) optionally, about 1% to 40% (w/v) of co-solvent, wherein the co-solvent is benzyl alcohol, benzyl benzoate, ethyl acetate, triacetin, lipids, $C_8$-$C_{10}$ triglycerides (e.g. MIGLYOL® 810 and MIGLYOL®812), $C_8$-$C_{10}$ triglycerides combined with linoleic acid (e.g. MIGLYOL® 818), $C_8$-$C_{10}$ triglycerides combined with succinic acid (e.g. MIGLYOL® 829), propylene glycol diester of $C_8$-$C_{10}$ fatty acids (e.g. MIGLYOL® 840), castor oil, cottonseed oil, sesame oil, soybean oil and safflower oil, or a combination thereof;
- d) optionally, about 0.01% to about 2.0% (w/v) of an antioxidant; and e) optionally about 0.01% to about 5.0% (w/v) of a pharmaceutically acceptable additive, excipient or mixtures thereof;

wherein the only pharmaceutically acceptable polymer present in said long-acting injectable composition is a liquid PEG and wherein the liquid PEG is present in the overall composition in a proportion representing the complement to 100% of the composition.

In other embodiments the present invention provides for long-acting injectable compositions for the treatment and/or prophylaxis of parasitic infections and infestations in or on animals comprising:
a) about 1 to 15% (w/v) of an isoxazoline active agent of the formula (Ia), (S)-Ia, (R)-Ia, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$; (R)-Ic wherein $X^1$, $X^2$ and $X^3$ are independently chloro, fluoro or $CF_3$; (III), (S)-III, (IV), (S)-IV, (Va), (S)-Va, (VIa) or (S)-VIa as shown above; or a pharmaceutically acceptable salt thereof,
b) pharmaceutically acceptable polymer which is a liquid PEG;
c) optionally, about 1% to 40% (w/v) of co-solvent, wherein the co-solvent is benzyl alcohol, benzyl benzoate, ethyl acetate, triacetin, lipids, $C_8$-$C_{10}$ triglycerides (e.g. MIGLYOL® 810 and MIGLYOL®812), $C_8$-$C_{10}$ triglycerides combined with linoleic acid (e.g. MIGLYOL® 818), $C_8$-$C_{10}$ triglycerides combined with succinic acid (e.g. MIGLYOL® 829), propylene glycol diester of $C_8$-$C_{10}$ fatty acids (e.g. MIGLYOL® 840), castor oil, cottonseed oil, sesame oil, soybean oil and safflower oil, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;

wherein the only pharmaceutically acceptable polymer present in said long-acting injectable composition is a liquid PEG and wherein the liquid PEG is present in the overall composition in a proportion representing the complement to 100% of the composition. In certain embodiments the present invention provides for long-acting injectable compositions for the treatment and/or prophylaxis of parasitic infections and infestations in or on animals comprising: a) about 0.5 to 30% (w/v) of an isoxazoline active agent of the formula (Ia), (S)-Ia, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$; (III), (S)-III, (IV), (S)-IV, (S)-Va, (VIa) or (S)-VIa as shown above, or a pharmaceutically acceptable salt thereof;
b) pharmaceutically acceptable polymer which is a liquid PEG and/or a pharmaceutically acceptable neutral oil;
c) optionally, about 1% to 40% (w/v) of a co-solvent, wherein the co-solvent is a $C_1$-$C_6$alcohol, benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG and/or neutral oil is present in the overall composition in a proportion representing the complement to 100% of the composition.

In certain embodiments the present invention provides for long-acting injectable compositions for the treatment and/or prophylaxis of parasitic infections and infestations in or on animals comprising:
a) about 0.5 to 20% (w/v) of an isoxazoline active agent of the formula (Ia), (S)-Ia, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$; (III), (S)-III, (IV), (S)-IV, (S)-Va, (VIa) or (S)-VIa as shown above, or a pharmaceutically acceptable salt thereof;
b) pharmaceutically acceptable polymer which is a liquid PEG and/or a pharmaceutically acceptable neutral oil;
c) optionally, about 1% to 40% (w/v) of co-solvent, wherein the co-solvent is a $C_1$-$C_6$alcohol, benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG and/or neutral oil is present in the overall composition in a proportion representing the complement to 100% of the composition.

In other embodiments the present invention provides for long-acting injectable compositions for the treatment and/or prophylaxis of parasitic infections and infestations in or on animals comprising:
a) about 1 to 20% (w/v) of an isoxazoline active agent of the formula (Ia), (S)-Ja, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$; (III), (S)-III, (IV), (S)-IV, (S)-Va, (VIa) or (S)-VIa as shown above, or a pharmaceutically acceptable salt thereof,
b) pharmaceutically acceptable polymer which is a liquid PEG and/or a pharmaceutically acceptable neutral oil;
c) optionally, about 1% to 40% (w/v) of co-solvent, wherein the co-solvent is a $C_1$-$C_6$alcohol, benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG and/or neutral oil is present in the overall composition in a proportion representing the complement to 100% of the composition.

In other embodiments the present invention provides for long-acting injectable compositions for the treatment and/or prophylaxis of parasitic infections and infestations in or on animals comprising:
a) about 1 to 15% (w/v) of an isoxazoline active agent of the formula (Ia), (S)-Ia, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$;

(III), (S)-III, (IV), (S)-IV, (S)-Va, (VIa) or (S)-VIa as shown above, or a pharmaceutically acceptable salt thereof;

or a pharmaceutically acceptable salt thereof,
b) pharmaceutically acceptable polymer which is a liquid PEG and/or a pharmaceutically acceptable neutral oil;
c) optionally, about 1% to 40% (w/v) of co-solvent, wherein the co-solvent is a $C_1$-$C_6$alcohol, benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;

wherein the only pharmaceutically acceptable polymer present in said long-acting injectable composition is a liquid PEG and wherein the liquid PEG and/or neutral oil is present in the overall composition in a proportion representing the complement to 100% of the composition.

In certain embodiments the present invention provides for long-acting injectable compositions for the treatment and/or prophylaxis of parasitic infections and infestations in or on animals comprising:
a) about 0.5 to 30% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;
b) pharmaceutically acceptable polymer which is a liquid PEG;
c) optionally, about 1% to 40% (w/v) of a co-solvent, wherein the co-solvent is ethanol, isopropanol or benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;

wherein the only pharmaceutically acceptable polymer present in said long-acting injectable composition is a liquid PEG and wherein the liquid PEG and/or neutral oil is present in the overall composition in a proportion representing the complement to 100% of the composition.

In certain embodiments the present invention provides for long-acting injectable compositions for the treatment and/or prophylaxis of parasitic infections and infestations in or on animals comprising:
a) about 0.5 to 30% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;
b) at least one pharmaceutically acceptable polymer which is a liquid PEG;
c) optionally, about 1% to 40% (w/v) of a co-solvent, wherein said co-solvent is a $C_8$-Cia triglyceride, benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;

wherein the only pharmaceutically acceptable polymer present in said long-acting injectable composition is a liquid PEG and wherein the liquid PEG and/or neutral oil is present in the overall composition in a proportion representing the complement to 100% of the composition.

In certain embodiments the present invention provides for long-acting injectable compositions for the treatment and/or prophylaxis of parasitic infections and infestations in or on animals comprising:
a) about 0.5 to 30% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;
b) at least one neutral oil, wherein said neutral oil is a $C_8$-$C_{10}$ triglyceride;
c) optionally, about 1% to 40% (w/v) of a co-solvent, wherein said co-solvent is ethanol, isopropanol, benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;

wherein the only pharmaceutically acceptable polymer present in said long-acting injectable composition is a liquid PEG and wherein the liquid PEG and/or neutral oil is present in the overall composition in a proportion representing the complement to 100% of the composition.

In certain embodiments the present invention provides for long-acting injectable compositions for the treatment and/or prophylaxis of parasitic infections and infestations in or on animals comprising:
a) about 0.5 to 20% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;
b) pharmaceutically acceptable polymer which is a liquid PEG;
c) optionally, about 1% to 40% (w/v) of co-solvent, wherein the co-solvent is ethanol, isopropanol or benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;

wherein the only pharmaceutically acceptable polymer present in said long-acting injectable composition is a liquid PEG and wherein the liquid PEG and/or neutral oil is present in the overall composition in a proportion representing the complement to 100% of the composition.

In other embodiments the present invention provides for long-acting injectable compositions for the treatment and/or prophylaxis of parasitic infections and infestations in or on animals comprising:
a) about 1 to 20% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;
or a pharmaceutically acceptable salt thereof,
b) pharmaceutically acceptable polymer which is a liquid PEG;

c) optionally, about 1% to 40% (w/v) of co-solvent, wherein the co-solvent is ethanol, isopropanol or benzyl alcohol, or a combination thereof;

d) optionally, about 0.01% to about 2.0% (w/v) of an antioxidant; and e) optionally about 0.01% to about 5.0% (w/v) of a pharmaceutically acceptable additive, excipient or mixtures thereof;

wherein the only pharmaceutically acceptable polymer present in said long-acting injectable composition is a liquid PEG and wherein the liquid PEG and/or neutral oil is present in the overall composition in a proportion representing the complement to 100% of the composition.

In other embodiments the present invention provides for long-acting injectable compositions for the treatment and/or prophylaxis of parasitic infections and infestations in or on animals comprising:

a) about 1 to 15% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;

or a pharmaceutically acceptable salt thereof, b) pharmaceutically acceptable polymer which is a liquid PEG;

c) optionally, about 1% to 40% (w/v) of co-solvent, wherein the co-solvent is ethanol, isopropanol or benzyl alcohol, or a combination thereof;

d) optionally, about 0.01% to about 2.0% (w/v) of an antioxidant; and e) optionally about 0.01% to about 5.0% (w/v) of a pharmaceutically acceptable additive, excipient or mixtures thereof;

wherein the only pharmaceutically acceptable polymer present in said long-acting injectable composition is a liquid PEG and wherein the liquid PEG and/or neutral oil is present in the overall composition in a proportion representing the complement to 100% of the composition.

In certain embodiments the present invention provides for long-acting injectable compositions for the treatment and/or prophylaxis of parasitic infections and infestations in or on animals comprising:

a) about 0.5 to 30% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;

b) pharmaceutically acceptable polymer which is a liquid PEG and/or a neutral oil;

c) optionally, about 1% to 20% (w/v) of a co-solvent, wherein the co-solvent is ethanol, isopropanol or benzyl alcohol, or a combination thereof;

d) optionally, about 0.01% to about 2.0% (w/v) of an antioxidant; and e) optionally about 0.01% to about 5.0% (w/v) of a pharmaceutically acceptable additive, excipient or mixtures thereof;

wherein the only pharmaceutically acceptable polymer present in said long-acting injectable composition is a liquid PEG and wherein the liquid PEG and/or neutral oil is present in the overall composition in a proportion representing the complement to 100% of the composition.

In certain embodiments the present invention provides for long-acting injectable compositions for the treatment and/or prophylaxis of parasitic infections and infestations in or on animals comprising:

a) about 0.5 to 20% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;

b) pharmaceutically acceptable polymer which is a liquid PEG and/or a neutral oil;

c) optionally, about 1% to 20% (w/v) of co-solvent, wherein the co-solvent is ethanol, isopropanol or benzyl alcohol, or a combination thereof;

d) optionally, about 0.01% to about 2.0% (w/v) of an antioxidant; and e) optionally about 0.01% to about 5.0% (w/v) of a pharmaceutically acceptable additive, excipient or mixtures thereof;

wherein the only pharmaceutically acceptable polymer present in said long-acting injectable composition is a liquid PEG and wherein the liquid PEG and/or neutral oil is present in the overall composition in a proportion representing the complement to 100% of the composition.

In other embodiments the present invention provides for long-acting injectable compositions for the treatment and/or prophylaxis of parasitic infections and infestations in or on animals comprising:

a) about 1 to 20% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;

or a pharmaceutically acceptable salt thereof, b) pharmaceutically acceptable polymer which is a liquid PEG and/or a neutral oil;

c) optionally, about 1% to 20% (w/v) of co-solvent, wherein the co-solvent is ethanol, isopropanol or benzyl alcohol, or a combination thereof;

d) optionally, about 0.01% to about 2.0% (w/v) of an antioxidant; and e) optionally about 0.01% to about 5.0% (w/v) of a pharmaceutically acceptable additive, excipient or mixtures thereof;

wherein the only pharmaceutically acceptable polymer present in said long-acting injectable composition is a liquid PEG and wherein the liquid PEG and/or neutral oil is present in the overall composition in a proportion representing the complement to 100% of the composition.

In other embodiments the present invention provides for long-acting injectable compositions for the treatment and/or prophylaxis of parasitic infections and infestations in or on animals comprising:

a) about 1 to 15% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;

or a pharmaceutically acceptable salt thereof, b) pharmaceutically acceptable polymer which is a liquid PEG and/or a neutral oil;

c) optionally, about 1% to 20% (w/v) of co-solvent, wherein the co-solvent is ethanol, isopropanol or benzyl alcohol, or a combination thereof;

d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG and/or neutral oil is present in the overall composition in a proportion representing the complement to 100% of the composition.

In other embodiments the present invention provides for long-acting injectable compositions for the treatment and/or prophylaxis of parasitic infections and infestations in or on animals comprising:
a) about 1 to 15% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;
or a pharmaceutically acceptable salt thereof,
b) pharmaceutically acceptable polymer which is a liquid PEG;
c) optionally, about 1% to 20% (w/v) of a co-solvent wherein said co-solvent is a $C_8$-Cia triglyceride, benzyl alcohol, or a combination thereof;
d) optionally, about 0.01% to about 2.0% (w/v) of an antioxidant; and
e) optionally about 0.01% to about 5.0% (w/v) of at least one pharmaceutically acceptable additive, excipient or mixtures thereof;
wherein the only pharmaceutically acceptable polymer present in said long-acting injectable composition is a liquid PEG and wherein the liquid PEG and/or neutral oil is present in the overall composition in a proportion representing the complement to 100% of the composition.

In other embodiments the present invention provides for long-acting injectable compositions for the treatment and/or prophylaxis of parasitic infections and infestations in or on animals comprising:
a) about 1 to 15% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;
or a pharmaceutically acceptable salt thereof,
b) at least one neutral oil, wherein said neutral oil is a $C_8$-$C_{10}$ triglyceride;
c) optionally, about 1% to 20% (w/v) at least one co-solvent, wherein said co-solvent is ethanol, isopropanol, benzyl alcohol, or a combination thereof;
d) optionally, about 0.01% to about 2.0% (w/v) of an antioxidant; and
e) optionally about 0.01% to about 5.0% (w/v) of at least one pharmaceutically acceptable additive, excipient or mixtures thereof;
wherein the only pharmaceutically acceptable polymer present in said long-acting injectable composition is a liquid PEG and wherein the liquid PEG and/or neutral oil is present in the overall composition in a proportion representing the complement to 100% of the composition.

In certain embodiments the present invention provides for long-acting injectable compositions for the treatment and/or prophylaxis of parasitic infections and infestations in or on animals comprising:
a) about 0.5 to 30% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;
b) pharmaceutically acceptable polymer which is a liquid PEG;
c) optionally, about 2% to 15% (w/v) of a co-solvent, wherein the co-solvent is ethanol, isopropanol or benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG is present in the overall composition in a proportion representing the complement to 100% of the composition.

In certain embodiments the present invention provides for long-acting injectable compositions for the treatment and/or prophylaxis of parasitic infections and infestations in or on animals comprising:
a) about 0.5 to 20% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;
b) pharmaceutically acceptable polymer which is a liquid PEG;
c) optionally, about 2% to 15% (w/v) of co-solvent, wherein the co-solvent is ethanol, isopropanol or benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG is present in the overall composition in a proportion representing the complement to 100% of the composition.

In other embodiments the present invention provides for long-acting injectable compositions for the treatment and/or prophylaxis of parasitic infections and infestations in or on animals comprising:
a) about 1 to 20% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;
or a pharmaceutically acceptable salt thereof,
b) pharmaceutically acceptable polymer which is a liquid PEG;
c) optionally, about 2% to 15% (w/v) of co-solvent, wherein the co-solvent is ethanol, isopropanol or benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG is present in the overall composition in a proportion representing the complement to 100% of the composition.

In other embodiments the present invention provides for long-acting injectable compositions for the treatment and/or prophylaxis of parasitic infections and infestations in or on animals comprising:
a) about 1 to 15% (w/v) of an isoxazoline active agent of the formula (Ia), (S)-Ia, (Ic), wherein $X^1$ is chloro, $X^2$ is fluoro and $X^3$ is $CF_3$; or (S)-Ic, wherein $X^1$ is chloro, $X^2$ is fluoro and $X^3$ is $CF_3$, as shown above, or a pharmaceutically acceptable salt thereof;
or a pharmaceutically acceptable salt thereof,
b) pharmaceutically acceptable polymer which is a liquid PEG;
c) optionally, about 2% to 15% (w/v) of co-solvent, wherein the co-solvent is ethanol, isopropanol or benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG is present in the overall composition in a proportion representing the complement to 100% of the composition.

In certain embodiments the present invention provides for long-acting injectable compositions for the treatment and/or prophylaxis of parasitic infections and infestations in or on animals comprising:
a) about 0.5 to 15% (w/v) of an isoxazoline active agent of the formula (S)-Ia or (S)-Ic, wherein $X^1$ is chloro, $X^2$ is fluoro and $X^3$ is $CF_3$, as shown above, or a pharmaceutically acceptable salt thereof;
b) pharmaceutically acceptable polymer which is a liquid PEG;
c) optionally, about 2% to 15% (w/v) of a co-solvent, wherein the co-solvent is ethanol, isopropanol or benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG is present in the overall composition in a proportion representing the complement to 100% of the composition.

In certain embodiments the present invention provides for long-acting injectable compositions for the treatment and/or prophylaxis of parasitic infections and infestations in or on animals comprising:
a) about 5 to 20% (w/v) of an isoxazoline active agent of the formula (S)-Ia or (S)-Ic, wherein $X^1$ is chloro, $X^2$ is fluoro and $X^3$ is $CF_3$; as shown above, or a pharmaceutically acceptable salt thereof;
b) pharmaceutically acceptable polymer which is a liquid PEG;
c) optionally, about 2% to 15% (w/v) of co-solvent, wherein the co-solvent is ethanol, isopropanol or benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG is present in the overall composition in a proportion representing the complement to 100% of the composition.

In other embodiments the present invention provides for long-acting injectable compositions for the treatment and/or prophylaxis of parasitic infections and infestations in or on animals comprising:
a) about 5 to 15% (w/v) of an isoxazoline active agent of the formula (S)-Ia or (S)-Ic, wherein $X^1$ is chloro, $X^2$ is fluoro and $X^3$ is $CF_3$, as shown above, or a pharmaceutically acceptable salt thereof;
or a pharmaceutically acceptable salt thereof,
b) pharmaceutically acceptable polymer which is a liquid PEG;
c) optionally, about 2% to 10% (w/v) of co-solvent, wherein the co-solvent is ethanol, isopropanol or benzyl alcohol, or a combination thereof;
d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG is present in the overall composition in a proportion representing the complement to 100% of the composition.

In certain embodiments the present invention provides for long-acting injectable compositions for the treatment and/or prophylaxis of parasitic infections and infestations in or on animals comprising:
a) about 0.5 to 30% (w/v) of an isoxazoline active agent, such as, for example, any of the isoxazoline compounds provided for in the embodiments above (e.g., a compound of any of formulae I to VIa described above), such as, a compound of the formula (Ia), (S)-Ia, (R)-Ia, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$; (R)-Ic wherein $X^1$, $X^2$ and $X^3$ are independently chloro, fluoro or $CF_3$; (III), (S)-III, (IV), (S)-IV, (Va), (S)-Va, (VIa) or (S)-VIa as shown above;
or a pharmaceutically acceptable salt thereof:
b) pharmaceutically acceptable polymer which is a liquid PEG and/or a pharmaceutically acceptable neutral oil;
c) optionally, about 5% to 40% (w/v) of co-solvent selected from the group consisting of ethanol and isopropanol;
d) optionally, about 0.01% to about 2.0% (w/v) of an antioxidant; and
e) optionally about 0.01% to about 5.0% (w/v) of a pharmaceutically acceptable additive, excipient or mixtures thereof;
wherein the only pharmaceutically acceptable polymer present in said long-acting injectable composition is a liquid PEG and wherein the liquid PEG and/or neutral oil is present in the overall composition in a proportion representing the complement to 100% of the composition.

In other embodiments the present invention provides for long-acting injectable compositions for the treatment and/or prophylaxis of parasitic infections and infestations in or on animals comprising:
 a) about 1 to 30% (w/v) of an isoxazoline active agent, such as, for example, any of the isoxazoline compounds provided for in the embodiments above (e.g., a compound of any of formulae I to VIa described above), such as, a compound of the formula (Ia), (S)-Ia, (R)-Ia, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$; (R)-Ic wherein $X^1$, $X^2$ and $X^3$ are independently chloro, fluoro or $CF_3$; (III), (S)-III, (IV), (S)-IV, (Va), (S)-Va, (VIa) or (S)-VIa as shown above;
 or a pharmaceutically acceptable salt thereof:
 b) pharmaceutically acceptable polymer which is a liquid PEG and/or a neutral oil;
 c) optionally, about 5% to 40% (w/v) of co-solvent selected from the group consisting of ethanol and isopropanol;
 d) optionally, about 0.01% to about 2.0% (w/v) of an antioxidant; and
 e) optionally about 0.01% to about 5.0% (w/v) of a pharmaceutically acceptable additive, excipient or mixtures thereof;
 wherein the only pharmaceutically acceptable polymer present in said long-acting injectable composition is a liquid PEG and wherein the liquid PEG and/or the neutral oil is present in the overall composition in a proportion representing the complement to 100% of the composition.

In yet other embodiments the present invention provides for long-acting injectable compositions for the treatment and/or prophylaxis of parasitic infections and infestations in or on animals comprising:
 a) about 1 to 20% (w/v) of an isoxazoline active agent, such as, for example, any of the isoxazoline compounds provided for in the embodiments above (e.g., a compound of formulae I-VIa), such as, a compound of the formula (Ia), (S)-Ia, (R)-Ia, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$; (R)-Ic wherein $X^1$, $X^2$ and $X^3$ are independently chloro, fluoro or $CF_3$; (III), (S)-III, (IV), (S)-IV, (Va), (S)-Va, (VIa) or (S)-VIa as shown above; or a pharmaceutically acceptable salt thereof:
 b) pharmaceutically acceptable polymer which is a liquid PEG and/or a neutral oil;
 c) optionally, about 5% to 40% (w/v) of co-solvent selected from the group consisting of ethanol and isopropanol;
 d) optionally, about 0.01% to about 2.0% (w/v) of an antioxidant; and
 e) optionally about 0.01% to about 5.0% (w/v) of a pharmaceutically acceptable additive, excipient or mixtures thereof;
 wherein the only pharmaceutically acceptable polymer present in said long-acting injectable composition is a liquid PEG and wherein the liquid PEG and/or the neutral oil is present in the overall composition in a proportion representing the complement to 100% of the composition.

In other embodiments the present invention provides for long-acting injectable compositions for the treatment and/or prophylaxis of parasitic infections and infestations in or on animals comprising:
 a) about 5 to 20% (w/v) or about 5 to about 15% (w/v) of an isoxazoline active agent, such as, for example, any of the isoxazoline compounds provided for in the embodiments above (e.g., a compound of formulae I-VIa), such as, a compound of the formula (Ia), (S)-Ia, (R)-Ia, (Ic), wherein $X^1$, $X^2$ and $X^3$ are independently chloro, fluoro or $CF_3$; (S)-Ic, wherein $X^1$, $X^2$ and $X^3$ are independently chloro, fluoro or $CF_3$; (R)-Ic wherein $X^1$, $X^2$ and $X^3$ are independently chloro, fluoro or $CF_3$; (III), (S)-III, (IV), (S)-IV, (Va), (S)-Va, (VIa) or (S)-VIa as shown above; or a pharmaceutically acceptable salt thereof:
 b) pharmaceutically acceptable polymer which is a liquid PEG;
 c) optionally, about 5% to 40% (w/v) of co-solvent selected from the group consisting of ethanol and isopropanol;
 d) optionally, about 0.01% to about 2.0% (w/v) of an antioxidant; and
 e) optionally about 0.01% to about 5.0% (w/v) of a pharmaceutically acceptable additive, excipient or mixtures thereof;
 wherein the only pharmaceutically acceptable polymer present in said long-acting injectable composition is a liquid PEG and wherein the liquid PEG is present in the overall composition in a proportion representing the complement to 100% of the composition.

Another embodiment of the present invention is a long-acting injectable composition for the treatment and/or prevention of parasitic infections and infestations in or on animals consisting essentially of:
 a) an antiparasitic effective amount of at least one isoxazoline active agent, such as, for example, any of the isoxazoline compounds provided for in the embodiments above (e.g., a compound of formulae I-VIa), and optionally at least one additionally active agent as identified in this application;
 b) a liquid PEG and/or a pharmaceutically acceptable neutral oil;
 c) optionally, at least one co-solvent wherein said co-solvent is a polar solvent miscible with water;
 d) optionally, an antioxidant; and
 e) optionally, at least one pharmaceutically acceptable additive, excipient or mixtures thereof.

Another embodiment of the present invention is a long-acting injectable composition for the treatment and/or prevention of parasitic infections and infestations in or on animals consisting of:
 a) an antiparasitic effective amount of at least one isoxazoline active agent, such as, for example, any of the isoxazoline compounds provided for in the embodiments above (e.g., a compound of formulae I-VIa), and optionally at least one additionally active agent as identified in this application;
 b) a liquid PEG and/or a pharmaceutically acceptable neutral oil;
 c) at least one co-solvent wherein said co-solvent is not miscible with water;
 d) optionally, an antioxidant; and
 e) optionally, at least one pharmaceutically acceptable additive, excipient or mixtures thereof.

In this disclosure and in the claims, terms such as "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments. The term "consisting of" excludes any element, step or ingredient not specified in the claims.

Definitions

Terms used herein will have their customary meaning in the art unless specified otherwise. The organic moieties mentioned in the definitions of the variables of formula (I) are—like the term halogen—collective terms for individual listings of the individual group members. The prefix $C_n$-$C_m$ indicates in each case the possible number of carbon atoms in the group.

The term "animal" is used herein to include all mammals, birds and fish and also include all vertebrate animals. Animals include, but are not limited to, cats, dogs, cattle, chickens, cows, deer, goats, horses, llamas, pigs, sheep and yaks. It also includes an individual animal in all stages of development, including embryonic and fetal stages. In some embodiments, the animal will be a non-human animal.

The term "essentially pure" is used herein to indicate that a compound or an enantiomer is at least about 90% pure, at least about 95%, at least about 98% pure, or higher.

The term "alkyl" refers to saturated straight, branched, primary, secondary or tertiary hydrocarbons, including those having 1 to 20 atoms. In some embodiments, alkyl groups will include $C_1$-$C_{12}$, $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

Cyclic alkyl groups or "cycloalkyl" include those with 3 to 10 carbon atoms having single or multiple condensed rings. In some embodiments, cycloalkyl groups include $C_4$-$C_7$ or $C_3$-$C_4$ cyclic alkyl groups. Non-limiting examples of cycloalkyl groups include adamantyl, cyclopropyl, cyclobutyl, cyclopentyl, cyclohexyl, cycloheptyl, cyclooctyl and the like.

The alkyl groups described herein can be unsubstituted or substituted with one or more moieties selected from the group consisting of alkyl, halo, haloalkyl, hydroxyl, carboxyl, acyl, acyloxy, amino, alkyl- or dialkylamino, amido, arylamino, alkoxy, aryloxy, nitro, cyano, azido, thiol, imino, sulfonic acid, sulfate, sulfonyl, sulfanyl, sulfinyl, sulfamoyl, ester, phosphonyl, phosphinyl, phosphoryl, phosphine, thioester, thioether, acid halide, anhydride, oxime, hydrazine, carbamate, phosphoric acid, phosphate, phosphonate, or any other viable functional group that does not inhibit the biological activity of the compounds of the invention, either unprotected, or protected as necessary, as known to those skilled in the art, for example, as taught in Greene, et al., Protective Groups in Organic Synthesis, John Wiley and Sons, Third Edition, 1999, hereby incorporated by reference.

Terms including the term "alkyl" such as "alkylcycloalkyl," "cycloalkylalkyl," "alkylamino," or "dialkylamino" will be understood to comprise an alkyl group as defined above linked to the other functional group, where the group is linked to the compound through the last group listed, as understood by those of skill in the art.

The term "alkenyl" refers to both straight and branched carbon chains which have at least one carbon-carbon double bond. In some embodiments, alkenyl groups may include $C_2$-$C_{20}$ alkenyl groups. In other embodiments, alkenyl includes $C_2$-$C_{12}$, $C_2$-$C_{10}$, $C_2$-$C_8$, $C_2$-$C_6$ or $C_2$-$C_4$ alkenyl groups. In one embodiment of alkenyl, the number of double bonds is 1-3, in another embodiment of alkenyl, the number of double bonds is one or two. Other ranges of carbon-carbon double bonds and carbon numbers are also contemplated depending on the location of the alkenyl moiety on the molecule. "$C_2$-$C_{10}$-alkenyl" groups may include more than one double bond in the chain. Examples include, but are not limited to, ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl; 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkynyl" refers to both straight and branched carbon chains which have at least one carbon-carbon triple bond. In one embodiment of alkynyl, the number of triple bonds is 1-3; in another embodiment of alkynyl, the number of triple bonds is one or two. In some embodiments, alkynyl groups include from $C_2$-$C_{20}$ alkynyl groups. In other embodiments, alkynyl groups may include $C_2$-$C_{12}$, $C_2$-$C_{10}$, $C_2$-$C_8$, $C_2$-$C_6$ or $C_2$-$C_4$ alkynyl groups. Other ranges of carbon-carbon triple bonds and carbon numbers are also contemplated depending on the location of the alkenyl moiety on the molecule. For example, the term "$C_2$-$C_{10}$-alkynyl" as used herein refers to a straight-chain or branched unsaturated hydrocarbon group having 2 to 10 carbon atoms and containing at least one triple bond, such as ethynyl, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1- yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the like.

The term "haloalkyl" refers to an alkyl group, as defined herein, which is substituted by one or more halogen atoms. For example $C_1$-$C_4$-haloalkyl includes, but is not limited to, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like.

The term "haloalkenyl" refers to an alkenyl group, as defined herein, which is substituted by one or more halogen atoms.

The term "haloalkynyl" refers to an alkynyl group, as defined herein, which is substituted by one or more halogen atoms.

"Alkoxy" refers to alkyl-O—, wherein alkyl is as defined above. Similarly, the terms "alkenyloxy," "alkynyloxy," "haloalkoxy," "haloalkenyloxy," "haloalkynyloxy," "cycloalkoxy," "cycloalkenyloxy," "halocycloalkoxy," and "halocycloalkenyloxy" refer to the groups alkenyl-O—, alkynyl-O—, haloalkyl-O—, haloalkenyl-O—, haloalkynyl-O—, cycloalkyl-O—, cycloalkenyl-O—, halocycloalkyl-O—, and halocycloalkenyl-O—, respectively, wherein alkenyl, alkynyl, haloalkyl, haloalkenyl, haloalkynyl, cycloalkyl, cycloalkenyl, halocycloalkyl, and halocycloalkenyl are as defined above. Examples of $C_1$-$C_6$-alkoxy include, but are not limited to, methoxy, ethoxy, $C_2H_5$—$CH_2O$—, $(CH_3)_2CHO$—, n-butoxy, $C_2H_5$—$CH(CH_3)O$—, $(CH_3)_2CH$—$CH_2O$—, $(CH_3)_3CO$—, n-pentoxy, 1-methylbutoxy, 2-methylbutoxy, 3-methylbutoxy, 1,1-dimethylpropoxy, 1,2-dimethylpropoxy, 2,2-dimethyl-propoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like.

The term "alkylthio" refers to alkyl-S—, wherein alkyl is as defined above. Similarly, the terms "haloalkylthio," "cycloalkylthio," and the like, refer to haloalkyl-S— and cycloalkyl-S— where haloalkyl and cycloalkyl are as defined above.

The term "alkylsulfinyl" refers to alkyl-S(O)—, wherein alkyl is as defined above. Similarly, the term "haloalkylsulfinyl" refers to haloalkyl-S(O)— where haloalkyl is as defined above.

The term "alkylsulfonyl" refers to alkyl-S(O)$_2$—, wherein alkyl is as defined above. Similarly, the term "haloalkylsulfonyl" refers to haloalkyl-S(O)$_2$— where haloalkyl is as defined above.

The term alkylamino and dialkylamino refer to alkyl-NH— and (alkyl)$_2$N— where alkyl is as defined above. Similarly, the terms "haloalkylamino" refers to haloalkyl-NH— where haloalkyl is as defined above.

The terms "alkylcarbonyl," "alkoxycarbonyl," "alkylaminocarbonyl," and "dialkylaminocarbonyl" refer to alkyl-C(O)—, alkoxy-C(O)—, alkylamino-C(O)— and dialkylamino-C(O)— where alkyl, alkoxy, alkylamino and dialkylamino are as defined above. Similarly, the terms "haloalkylcarbonyl," "haloalkoxycarbonyl," "haloalkylaminocarbonyl," and "dihaloalkylaminocarbonyl" refer to the groups haloalkyl-C(O)—, haloalkoxy-C(O)—, haloalkylamino-C(O)— and dihaloalkylamino-C(O)— where haloalkyl, haloalkoxy, haloalkylamino and dihaloalkylamino are as defined above.

"Aryl" refers to a monovalent aromatic carbocyclic group of from 6 to 14 carbon atoms having a single ring or multiple condensed rings. In some embodiments, aryl groups include $C_6$-$C_{10}$ aryl groups. Aryl groups include, but are not limited to, phenyl, biphenyl, naphthyl, tetrahydronaphtyl, phenylcyclopropyl and indanyl. Aryl groups may be unsubstituted or substituted by one or more moieties selected from halogen, cyano, nitro, hydroxy, mercapto, amino, alkyl, alkenyl, alkynyl, cycloalkyl, cycloalkenyl, haloalkyl, haloalkenyl, haloalkynyl, halocycloalkyl, halocycloalkenyl, alkoxy, alkenyloxy, alkynyloxy, haloalkoxy, haloalkenyloxy, haloalkynyloxy, cycloalkoxy, cycloalkenyloxy, halocycloalkoxy, halocycloalkenyloxy, alkylthio, haloalkylthio, cycloalkylthio, halocycloalkylthio, alkylsulfinyl, alkenylsulfinyl, alkynyl-sulfinyl, haloalkylsulfinyl, haloalkenylsulfinyl, haloalkynylsulfinyl, alkylsulfonyl, alkenylsulfonyl, alkynylsulfonyl, haloalkyl-sulfonyl, haloalkenylsulfonyl, haloalkynylsulfonyl, alkylamino, alkenylamino, alkynylamino, di(alkyl)amino, di(alkenyl)-amino, di(alkynyl)amino, or trialkylsilyl.

The terms "aralkyl" or "arylalkyl" refers to an aryl group that is bonded to the parent compound through a diradical alkylene bridge, (—$CH_2$—)$_n$, where n is 1-12 and where "aryl" is as defined above.

"Heteroaryl" refers to a monovalent aromatic group of from 1 to 15 carbon atoms, preferably from 1 to 10 carbon atoms, having one or more oxygen, nitrogen, and sulfur heteroatoms within the ring, preferably 1 to 4 heteroatoms, or 1 to 3 heteroatoms. The nitrogen and sulfur heteroatoms may optionally be oxidized. Such heteroaryl groups can have a single ring (e.g., pyridyl or furyl) or multiple condensed rings provided that the point of attachment is through a heteroaryl ring atom. Preferred heteroaryls include pyridyl, pyridazinyl, pyrimidinyl, pyrazinyl, triazinyl, pyrrolyl, indolyl, quinolinyl, isoquinolinyl, quinazolinyl, quinoxalinnyl, furanyl, thiophenyl, furyl, pyrrolyl, imidazolyl, oxazolyl, isoxazolyl, isothiazolyl, pyrazolyl benzofuranyl, and benzothiophenyl. Heteroaryl rings may be unsubstituted or substituted by one or more moieties as described for aryl above.

"Heterocyclyl," "heterocyclic" or "heterocyclo" refer to fully saturated or unsaturated, cyclic groups, for example, 3 to 7 membered monocyclic or 4 to 7 membered monocyclic; 7 to 11 membered bicyclic, or 10 to 15 membered tricyclic ring systems, which have one or more oxygen, sulfur or nitrogen heteroatoms in ring, preferably 1 to 4 or 1 to 3 heteroatoms. The nitrogen and sulfur heteroatoms may optionally be oxidized and the nitrogen heteroatoms may optionally be quaternized. The heterocyclic group may be attached at any heteroatom or carbon atom of the ring or ring system and may be unsubstituted or substituted by one or more moieties as described for aryl groups above.

Exemplary monocyclic heterocyclic groups include, but are not limited to, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like.

Exemplary bicyclic heterocyclic groups include, but are not limited to, indolyl, benzothiazolyl, benzoxazolyl, benzodioxolyl, benzothienyl, quinuclidinyl, quinolinyl, tetrahydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl and the like.

Exemplary tricyclic heterocyclic groups include carbazolyl, benzidolyl, phenanthrolinyl, acridinyl, phenanthridinyl, xanthenyl, and the like.

Halogen means the atoms fluorine, chlorine, bromine and iodine. The designation of "halo" (e.g. as illustrated in the term haloalkyl) refers to all degrees of substitutions from a single substitution to a perhalo substitution (e.g. as illustrated with methyl as chloromethyl ($-CH_2Cl$), dichloromethyl ($-CHCl_2$), trichloromethyl ($-CCl_3$)).

By the term "enriched" is meant when the weight:weight ratio is at least approximately 1.05 or higher in favor of the enantiomer that displays significant in vitro and in vivo activity (the eutomer).

Stereoisomers and Polymorphic Forms

As noted above, it will be appreciated by those of skill in the art that certain compounds within the compositions of the invention may exist and be isolated as optically active and racemic forms. Compounds having one or more chiral centers, including at a sulfur atom, may be present as single enantiomers or diastereomers or as mixtures of enantiomers and/or diastereomers. For example, it is well known in the art that sulfoxide compounds may be optically active and may exist as single enantiomers or racemic mixtures. In addition, compounds within the compositions of the invention may include one or more chiral centers, which results in a theoretical number of optically active isomers. Where compounds within the compositions of the invention include n chiral centers, the compounds may comprise up to $2^n$ optical isomers. The present invention encompasses compositions comprising the specific enantiomers or diastereomers of each compound as well as mixtures of different enantiomers and/or diastereomers of the compounds of the invention that possess the useful properties described herein. In addition, the invention encompasses compositions comprising one or more conformational isomers (e.g. rotamers) as well as mixtures of conformational isomers. Conformational isomers of the isoxazoline compounds may be produced by a restriction of rotation about the amide bond bonded to the aryl or heteroaryl ring (e.g. the amide bonded to the naphthyl group in formula (I)). The optically active forms can be prepared by, for example, resolution of the racemic forms by selective crystallization techniques, by synthesis from optically active precursors, by chiral synthesis, by chromatographic separation using a chiral stationary phase or by enzymatic resolution.

In addition, the compounds within the compositions of the invention may exist as hydrates or solvates, in which a certain stoichiometric amount of water or a solvent is associated with the molecule in the crystalline form. The compositions of the invention may include hydrates and solvates of the active agents. In some embodiments, the compositions of the invention may include up to 15% (w/w), up to 20% (w/w), or up to 30% (w/w) of a particular solid form.

Salts

Also contemplated within the scope of the invention are acid or base salts, where applicable, of the compounds of the invention provided for herein.

The term "acid salt" contemplates salts of the compounds with all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, acetic acid, propionic acid, isopropionic acid, valeric acid, α-hydroxy acids such as glycolic acid and lactic acid, chloroacetic acid, benzoic acid, methane sulfonic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, see-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base salt" contemplates salts of the compounds with all pharmaceutically acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts ($NH4^+$), alkyl- and dialkylammonium salts, and salts of cyclic amines such as the morpholine and piperidine salts.

In another embodiment, the long-acting injectable compositions of present invention comprise an effective amount of at least one isoxazoline or a pharmaceutically acceptable salt thereof in combination at least one other active agent. In one embodiment, the long-acting injectable compositions comprise an effective amount of at least one isoxazoline compound of formula (I) to (VI), or a pharmaceutically acceptable salt thereof, in combination with at least one other active agent that is systemically-active.

Additional veterinary/pharmaceutical active ingredients may be used with the compositions of the invention. In some embodiments, the additional active agents may include, but are not limited to, acaricides, anthelmintics, anti-parasitics and insecticides. Anti-parasitic agents can include both ectoparasiticidal and/or endoparasiticidal agents.

Veterinary pharmaceutical agents that may be included in the compositions of the invention are well-known in the art (see e.g. *Plumb' Veterinary Drug Handbook,* 5th Edition, ed. Donald C. Plumb, Blackwell Publishing, (2005) or *The Merck Veterinary Manual,* 9th Edition, (January 2005)) and include but are not limited to acarbose, acepromazine maleate, acetaminophen, acetazolamide, acetazolamide sodium, acetic acid, acetohydroxamic acid, acetylcysteine, acitretin, acyclovir, albendazole, albuterol sulfate, alfentanil, allopurinol, alprazolam, altrenogest, amantadine, amikacin sulfate, aminocaproic acid, aminopentamide hydrogen sulfate, aminophylline/theophylline, amiodarone, amitriptyline, amlodipine besylate, ammonium chloride, ammonium molybdate, amoxicillin, clavulanate potassium, amphotericin B desoxycholate, amphotericin B lipid-based, ampicillin, amprolium, antacids (oral), antivenin, apomorphione, apramycin sulfate, ascorbic acid, asparaginase, aspiring, atenolol, atipamezole, atracurium besylate, atropine sulfate, aurnofin, aurothioglucose, azaperone, azathioprine, azithromycin, baclofen, barbituates, benazepril, betamethasone, bethanechol chloride, bisacodyl, bismuth subsalicylate, bleomycin sulfate, boldenone undecylenate, bromides, bromocriptine mesylate, budenoside, buprenorphine, buspirone, busulfan, butorphanol tartrate, cabergoline, calcitonin salmon, calcitrol, calcium salts, captopril, carbenicillin indanyl sodium, carbimazole, carboplatin, carnitine, carprofen, carvedilol, cefadroxil, cefazolin sodium, cefixime, clorsulon, cefoperazone sodium, cefotaxime sodium, cefotetan disodium, cefoxitin sodium, cefpodoxime proxetil, ceftazidime, ceftiofur sodium, ceftiofur, ceftiaxone sodium, cephalexin, cephalosporins, cephapirin, charcoal (activated), chlorambucil, chloramphenicol, chlordiazepoxide, chlordiazepoxide+/− clidinium bromide, chlorothiazide, chlorpheniramine maleate, chlorpromazine, chlorpropamide, chlortetracycline, chorionic gonadotropin (HCG), chromium, cimetidine, ciprofloxacin, cisapride, cisplatin, citrate salts, clarithromycin, clemastine fumarate, clenbuterol, clindamycin, clofazimine, clomipramine, claonazepam, clonidine, cloprostenol sodium, clorazepate dipotassium, clorsulon, cloxacillin, codeine phosphate, colchicine, corticotropin (ACTH), cosyntropin, cyclophosphamide, cyclosporine, cyproheptadine, cytarabine, dacarbazine, dactinomycin/actinomycin D, dalteparin sodium, danazol, dantrolene sodium, dapsone, decoquinate, deferoxamine mesylate, deracoxib, deslorelin acetate, desmopressin acetate, desoxycorticosterone pivalate, detomidine, dexamethasone, dexpanthenol, dexraazoxane, dextran, diazepam, diazoxide (oral), dichlorphenamide, diclofenac sodium, dicloxacillin, diethylcarbamazine citrate, diethylstilbestrol (DES), difloxacin, digoxin, dihydrotachysterol (DHT), diltiazem, dimenhydrinate, dimercaprol/BAL, dimethyl sulfoxide, dinoprost tromethamine, diphenylhydramine, disopyramide phosphate, dobutamine, docusate/DSS, dolasetron mesylate, domperidone, dopamine, doramectin, doxapram, doxepin, doxorubicin, doxycycline, edetate calcium disodium. calcium EDTA, edrophonium chloride, enalapril/enalaprilat, enoxaparin sodium, enrofloxacin, ephedrine sulfate, epinephrine, epoetin/erythropoietin, eprinomectin, epsiprantel, erythromycin, esmolol, estradiol cypionate, ethacrynic acid/ethacrynate sodium, ethanol (alcohol), etidronate sodium, etodolac, etomidate, euthanasia agents w/pentobarbital, famotidine, fatty acids (essential/omega), felbamate, fentanyl, ferrous sulfate, filgrastim, finasteride, fipronil, florfenicol, fluconazole, flucytosine, fludrocortisone acetate, flumazenil, flumethasone, flunixin meglumine, fluorouracil (5-FU), fluoxetine, fluticasone propionate, fluvoxamine maleate, fomepizole (4-MP), furazolidone, furosemide, gabapentin, gemcitabine, gentamicin sulfate, glimepiride, glipizide, glucagon, glucocorticoid agents, glucosamine/chondroitin sulfate, glutamine, glyburide, glycerin (oral), glycopyrrolate, gonadorelin, grisseofulvin, guaifenesin, halothane, hemoglobin glutamer-200 (OXYGLOBIN®), heparin, hetastarch, hyaluronate sodium, hydrazaline, hydrochlorothiazide, hydrocodone bitartrate, hydrocortisone, hydromorphone, hydroxyurea, hydroxyzine, ifosfamide, imidacloprid, imidocarb dipropinate, impenem-cilastatin sodium, imipramine, inamrinone lactate, insulin, interferon alfa-2a (human recombinant), iodide (sodium/potassium), ipecac (syrup), ipodate sodium, iron dextran, isoflurane, isoproterenol, isotretinoin, isoxsuprine, itraconazole, ivermectin, kaolin/pectin, ketamine, ketoconazole, ketoprofen, ketorolac tromethamine, lactulose, leuprolide, levamisole, levetiracetam, levothyroxine sodium, lidocaine, lincomycin, liothyronine sodium, lisinopril, lomustine (CCNU), lufenuron, lysine, magnesium, mannitol, marbofloxacin, mechlorethamine, meclizine, meclofenamic acid, medetomidine, medium chain triglycerides, medroxyprogesterone acetate, megestrol acetate, melarsomine, melatonin, meloxican, melphalan, meperidine, mercaptopurine, meropenem, metformin, methadone, methazolamide, methenamine mandelate/hippurate, methimazole, methionine, methocarbamol, methohexital sodium, methotrexate, methoxyflurane, methylene blue, methylphenidate, methylprednisolone, metoclopramide, metoprolol, metronidaxole, mexiletine, mibolerlone, midazolam milbemycin oxime, mineral oil, minocycline, misoprostol, mitotane, mitoxantrone, morphine sulfate, moxidectin, naloxone, mandrolone decanoate, naproxen, narcotic (opiate) agonist analgesics, neomycin sulfate, neostigmine, niacinamide, nitazoxanide, nitenpyram, nitrofurantoin, nitroglycerin, nitroprusside sodium, nizatidine, novobiocin sodium, nystatin, octreotide acetate, olsalazine sodium, omeprozole, ondansetron, opiate antidiarrheals, orbifloxacin, oxacillin sodium, oxazepam, oxibutynin chloride, oxymorphone, oxytretracycline, oxytocin, pamidronate disodium, pancreplipase, pancuronium bromide, paromomycin sulfate, parozetine, pencillamine, general information penicillins, penicillin G, penicillin V potassium, pentazocine, pentobarbital sodium, pentosan polysulfate sodium, pentoxifylline, pergolide mesylate, phenobarbital, phenoxybenzamine, pheylbutazone, phenylephrine, phenypropanolamine, phenytoin sodium, pheromones, parenteral phosphate, phytonadione/vitamin K-1, pimobendan, piperazine, pirlimycin, piroxicam, polysulfated glycosaminoglycan, ponazuril, potassium chloride, pralidoxime chloride, prazosin, prednisolone/prednisone, primidone, procainamide, procarbazine, prochlorperazine, propantheline bromide, Propionibacterium acnes injection, propofol, propranolol, protamine sulfate, pseudoephedrine, psyllium hydrophilic mucilloid, pyridostigmine bromide, pyrilamine maleate, pyrimethamine, quinacrine, quinidine, ranitidine, rifampin, s-adenosyl-methionine (SAMe), saline/hyperosmotic laxative, selamectin, selegiline/1-deprenyl, sertraline, sevelamer, sevoflurane, silymarin/milk thistle, sodium bicarbonate, sodium polystyrene sulfonate, sodium stibogluconate, sodium sulfate, sodum thiosulfate, somatotropin, sotalol, spectinomycin, spironolactone, stanozolol, streptokinase, streptozocin, succimer, succinylcholine chloride, sucralfate, sufentanil citrate, sulfachlorpyridazine sodium, sulfadiazine/trimethroprim, sulfamethoxazole/trimethoprim, sulfadimentoxine, sulfadimethoxine/ormetoprim, sulfasalazine, taurine, tepoxaline, terbinafline, terbutaline sulfate, testosterone, tetracycline, thiacetarsamide sodium, thiamine, thioguanine, thiopental sodium, thiotepa, thyrotropin, tiamulin, ticarcilin disodium, tiletamine/zolazepam, tilmocsin, tiopronin, tobramycin sulfate, tocainide, tolazoline, telfenamic acid, topiramate, tramadol, trimcinolone acetonide, trientine, trilostane, trimepraxine tartrate w/prednisolone, tripelennamine, tylosin, urdosiol, valproic acid, vanadium, vancomycin, vasopressin, vecuronium bromide, verapamil, vinblastine sulfate, vincristine sulfate, vitamin E/selenium, warfarin sodium, xylazine, yohimbine, zafirlukast, zidovudine (AZT), zinc acetate/zinc sulfate, zonisamide and mixtures thereof.

In one embodiment of the invention, arylpyrazole compounds such as phenylpyrazoles, known in the art may be combined with the isoxazoline compounds in the long-acting injectable compositions of the invention. Examples of such arylpyrazole compounds include but are not limited to those described in U.S. Pat. Nos. 6,001,384; 6,010,710; 6,083,519; 6,096,329; 6,174,540; 6,685,954 and 6,998,131 (all of which are incorporated herein by reference, each assigned to Merial, Ltd., Duluth, GA).

In another embodiment of the invention, one or more macrocyclic lactones or lactams, which act as an acaricide, anthelmintic agent and/or insecticide, can be added to the compositions of the invention.

The macrocyclic lactones include, but are not limited to, avermectins such as abamectin, dimadectin, doramectin, emamectin, eprinomectin, ivermectin, latidectin, lepimectin, selamectin and ML-1,694,554, and milbemycins such as milbemectin, milbemycin D, milbemycin oxime, moxidectin and nemadectin. Also included are the 5-oxo and 5-oxime derivatives of said avermectins and milbemycins. Examples of combinations of arylpyrazole compounds with macrocyclic lactones include but are not limited to those described in U.S. Pat. Nos. 6,426,333; 6,482,425; 6,962,713 and 6,998,131 (all incorporated herein by reference—each assigned to Merial, Ltd., Duluth, GA).

The macrocyclic lactone compounds are known in the art and can easily be obtained commercially or through synthesis techniques known in the art. Reference is made to the widely available technical and commercial literature. For avermectins, ivermectin and abamectin, reference may be made, for example, to the work "Ivermectin and Abamectin", 1989, by M. H. Fischer and H. Mrozik, William C. Campbell, published by Springer Verlag., or Albers-Schönberg et al. (1981), "Avermectins Structure Determination", J. Am. Chem. Soc., 103, 4216-4221. For doramectin, "Veterinary Parasitology", vol. 49, No. 1, July 1993, 5-15 may be consulted. For milbemycins, reference may be made, inter alia, to Davies H. G. et al., 1986, "Avermectins and Milbemycins", Nat. Prod. Rep., 3, 87-121, Mrozik H. et al., 1983, Synthesis of Milbemycins from Avermectins, Tetrahedron Lett., 24, 5333-5336, U.S. Pat. No. 4,134,973 and EP 0 677 054.

Macrocyclic lactones are either natural products or are semi-synthetic derivatives thereof. The structure of the avermectins and milbemycins are closely related, e.g., by sharing a complex 16-membered macrocyclic lactone ring. The natural product avermectins are disclosed in U.S. Pat. No. 4,310,519 and the 22,23-dihydro avermectin compounds are disclosed in U.S. Pat. No. 4,199,569. Mention is also made of U.S. Pat. Nos. 4,468,390, 5,824,653, EP 0 007 812 A1, U.K. Patent Specification 1 390 336, EP 0 002 916, and New Zealand Patent No. 237 086, inter alia. Naturally occurring milbemycins are described in U.S. Pat. No. 3,950,360 as well as in the various references cited in "The Merck Index" 12$^{th}$ ed., S. Budavari, Ed., Merck & Co., Inc. Whitehouse Station, New Jersey (1996). Latidectin is described in the "International Nonproprietary Names for Pharmaceutical Substances (INN)", WHO Drug Information, vol. 17, no. 4, pp. 263-286, (2003). Semisynthetic derivatives of these classes of compounds are well known in the art and are described, for example, in U.S. Pat. Nos. 5,077,308, 4,859,657, 4,963,582, 4,855,317, 4,871,719, 4,874,749, 4,427,663, 4,310,519, 4,199,569, 5,055,596, 4,973,711, 4,978,677, 4,920,148 and EP 0 667 054.

In another embodiment of the invention, the invention comprises a long-acting injectable composition comprising an isoxazoline compound in combination with systemically-acting compounds from a class of acaricides or insecticides known as insect growth regulators (IGRs). Compounds belonging to this group are well known to the practitioner and represent a wide range of different chemical classes. These compounds all act by interfering with the development or growth of the insect pests. Insect growth regulators are described, for example, in U.S. Pat. Nos. 3,748,356, 3,818,047, 4,225,598, 4,798,837, 4,751,225, EP 0 179 022 or U.K. 2 140 010 as well as U.S. Pat. Nos. 6,096,329 and 6,685,954 (all incorporated herein by reference).

In one embodiment the IGR is a compound that mimics juvenile hormone. Examples of juvenile hormone mimics include azadirachtin, diofenolan, fenoxycarb, hydroprene, kinoprene, methoprene, pyriproxyfen, tetrahydroazadirachtin and 4-chloro-2(2-chloro-2-methyl-propyl)-5-(6-iodo-3-pyridylmethoxy)pyridazine-3(2H)-one.

In an embodiment, the long-acting injectable compositions of present invention comprise an effective amount of at least one isoxazoline of formula (I) to (VIa), or a pharmaceutically acceptable salt thereof, in combination with methoprene or pyriproxyfen.

In another embodiment, the IGR compound is a chitin synthesis inhibitor. Chitin synthesis inhibitors include chlorofluazuron, cyromazine, diflubenzuron, fluazuron, flucycloxuron, flufenoxuron, hexaflumoron, lufenuron, tebufenozide, teflubenzuron, triflumuron, novaluron, 1-(2,6-difluorobenzoyl)-3-(2-fluoro-4-(trifluoromethyl)phenylurea, 1-(2,6-difluoro-benzoyl)-3-(2-fluoro-4-(1,1,2,2-tetrafluoroethoxy)-phenylurea and 1-(2,6-difluorobenzoyl)-3-(2-fluoro-4-trifluoromethyl)phenylurea.

In yet another embodiment of the invention, adulticide insecticides and acaricides can also be added to the long-acting compositions of the present invention. These include pyrethrins (which include cinerin I, cinerin II, jasmolin I, jasmolin II, pyrethrin I, pyrethrin II and mixtures thereof) and pyrethroids, and carbamates including, but are not limited to, benomyl, carbanolate, carbaryl, carbofuran, methiocarb, metolcarb, promacyl, propoxur, aldicarb, butocarboxim, oxamyl, thiocarboxime and thiofanox. In one embodiment, the compositions can include permethrin in combination with an isoxazoline active agent.

In some embodiments, the long-acting injectable compositions of the present invention may include one or more antinematodal agents including, but not limited to, active agents in the benzimidazoles, imidazothiazoles, tetrahydropyrimidines, and organophosphate class of compounds. In some embodiments, benzimidazoles including, but not limited to, thiabendazole, cambendazole, parbendazole, oxibendazole, mebendazole, flubendazole, fenbendazole, oxfendazole, albendazole, cyclobendazole, febantel, thiophanate and its o,o-dimethyl analogue may be included in the compositions.

In other embodiments, the long-acting injectable compositions of the present invention may include an imidazothiazole compounds including, but not limited to, tetramisole, levamisole and butamisole. In still other embodiments, the long-acting compositions of the present invention may include tetrahydropyrimidine active agents including, but not limited to, pyrantel, oxantel, and morantel. Suitable organophosphate active agents include, but are not limited to, coumaphos, trichlorfon, haloxon, naftalofos and dichlorvos, heptenophos, mevinphos, monocrotophos, TEPP, and tetrachlorvinphos.

In other embodiments, the long-acting injectable compositions of the present invention may include the antinematodal compounds phenothiazine and piperazine as the neutral compound or in various salt forms, diethylcarbamazine, phenols such as disophenol, arsenicals such as arsenamide, ethanolamines such as bephenium, thenium closylate, and methyluridine; cyanine dyes including pyrvinium chloride, pyrvinium pamoate and dithiazanine iodide; isothiocyanates including bitoscanate, suramin sodium, phthalofyne, and various natural products including, but not limited to, hygromycin B, α-santonin and kainic acid.

In other embodiments, the long-acting injectable compositions of the present invention of the invention may include anti-trematodal agents. Suitable anti-trematodal agents include, but are not limited to, the miracils such as miracil D and mirasan; praziquantel, clonazepam and its 3-methyl derivative, oltipraz, lucanthone, hycanthone, oxamniquine, amoscanate, niridazole, nitroxynil, various bisphenol compounds known in the art including hexachlorophene, bithionol, bithionol sulfoxide and menichlopholan; various salicylanilide compounds including tribromsalane, oxyclozanide, diloxanide, rafoxanide, brotianide, bromoxanide and closantel; triclabendazole, diamfenetide, clorsulon, hetolin and emetine.

Anticestodal compounds may also be advantageously used in the long-acting compositions of the present invention of the invention including, but not limited to, arecoline in various salt forms, bunamidine, niclosamide, nitroscanate, paromomycin and paromomycin II.

In yet other embodiments, the long-acting injectable compositions of the present invention may include other active agents that are effective against arthropod parasites. Suitable active agents include, but are not limited to, bromocyclen, chlordane, DDT, endosulfan, lindane, methoxychlor, toxaphene, bromophos, bromophos-ethyl, carbophenothion, chlorfenvinphos, chlorpyrifos, crotoxyphos, cythioate, diazinon, dichlorenthion, diemthoate, dioxathion, ethion, famphur, fenitrothion, fenthion, fospirate, iodofenphos, malathion, naled, phosalone, phosmet, phoxim, propetamphos, ronnel, stirofos, allethrin, cyhalothrin, cypermethrin, deltamethrin, fenvalerate, flucythrinate, permethrin, phenothrin, pyrethrins, resmethrin, benzyl benzoate, carbon disulfide, crotamiton, diflubenzuron, diphenylamine, disulfiram, isobornyl thiocyanato acetate, methoprene, monosulfiram, pirenonylbutoxide, rotenone, triphenyltin acetate, triphenyltin hydroxide, deet, dimethyl phthalate, and the compounds 1,5a,6,9,9a,9b-hexahydro-4a(4H)-dibenzofurancarboxaldehyde (MGK-11), 2-(2-ethylhexyl)-3a,4,7,7a-tetrahydro-4,7-methano-1H-isoindole-1,3(2H)dione (MGK-264), dipropyl-2,5-pyridinedicarboxylate (MGK-326) and 2-(octylthio)ethanol (MGK-874).

An antiparasitic agent that can be combined with an isoxazoline compounds in the long-acting compositions of the present invention can be a biologically active peptide or protein including, but not limited to, depsipeptides, which act at the neuromuscular junction by stimulating presynaptic receptors belonging to the secretin receptor family resulting in the paralysis and death of parasites. In one embodiment of the depsipeptide, the depsipeptide is emodepside (see Willson et al., *Parasitology*, January 2003, 126 (Pt 1):79-86). In another embodiment, the depsipeptide is PF1022A or a derivative thereof.

In another embodiment, the long-acting injectable compositions of the present invention may comprise an active agent from the neonicotinoid class of pesticides. The neonicotinoids bind and inhibit insect specific nicotinic acetylcholine receptors. In one embodiment, the neonicotinoid insecticidal agent that can be combined with an isoxazoline compound to form a long-acting injectable composition of the invention is imidacloprid. Imidacloprid is a well-known neonicotinoid active agent and is the key active ingredient in the topical parasiticide products Advantage®, Advantage® II, K9 Advantix®, and K9 Advantix® II sold by Bayer Animal Health and the oral soft-chewable composition Advantus™ from Piedmont Animal Health. Agents of this class are described, for example, in U.S. Pat. No. 4,742,060 or in EP 0 892 060.

In another embodiment, the long-acting injectable compositions of the present invention may comprise nitenpyram, another active agent of the neonicotinoid class of pesticides. Nitenpyram has the following chemical structure and is the active ingredient in the oral product CAPSTAR™ Tablets sold by Novartis Animal Health.

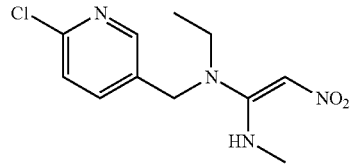 [SMILES: CCN(Cc1ccc(Cl)nc1)/C(=C/[N+](=O)[O-])NC]

Nitenpyram is active against adult fleas when given daily as an oral tablet. Nitenpyram works by interfering with normal nerve transmission and leads to the death of the insect. Nitenpyram has a very fast onset of action against fleas. For example, CAPSTAR™ Tablets begin to act against fleas in as early as 30 minutes after administration and is indicated for use as often as once a day. However, nitenpyram is only known to be effective when administered orally as a systemic parasiticide, as with CAPSTAR™ Tablets.

In yet another embodiment, the invention provides the long-acting compositions of the present invention comprising 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound of formula Ia) in combination with nitenpyram.

In yet another embodiment, the invention provides the long-acting compositions of the present invention comprising 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide (Compound of formula Ia) in combination with imidacloprid.

In certain embodiments, an insecticidal agent that can be combined with the long-acting compositions of the present invention is a semicarbazone, such as metaflumizone.

In another embodiment, the long-acting injectable compositions of the present invention may advantageously include a combination of isoxazoline compounds known in the art. These active agents are described in WO 2007/079162, WO 2007/075459 and US 2009/0133319, WO 2007/070606 and US 2009/0143410, WO 2009/003075, WO 2009/002809, WO 2009/024541, WO 2005/085216 and US 2007/0066617 and WO 2008/122375, all of which are incorporated herein by reference in their entirety.

In another embodiment of the invention, nodulisporic acid and its derivatives (a class of known acaricidal, anthelmintic, anti-parasitic and insecticidal agents) may be added to the long-acting compositions of the present invention. These compounds are used to treat or prevent infections in humans and animals and are described, for example, in U.S. Pat. Nos. 5,399,582, 5,962,499, 6,221,894 and 6,399,786, all of which are hereby incorporated by reference in their entirety. The compositions may include one or more of the known nodulisporic acid derivatives in the art, including all stereoisomers, such as those described in the patents cited above.

In another embodiment, anthelmintic compounds of the amino acetonitrile class (AAD) of compounds such as monepantel (ZOLVIX), and the like, may be added to the. the long-acting compositions of the present invention These compounds are described, for example, in WO 2004/024704 and U.S. Pat. No. 7,084,280 (incorporated by reference); Sager et al., Veterinary Parasitology, 2009, 159, 49-54; Kaminsky et al., Nature vol. 452, 13 Mar. 2008, 176-181.

The compositions of the invention may also include aryloazol-2-yl cyanoethylamino compounds such as those described in U.S. Pat. No. 8,088,801 to Soll et al., which is incorporated herein in its entirety, and thioamide derivatives of these compounds, as described in U.S. Pat. No. 7,964,621, which is incorporated herein by reference.

The long-acting injectable compositions of the present invention may also be combined with paraherquamide compounds and derivatives of these compounds, including derquantel (see Ostlind et al., *Research in Veterinary Science*, 1990, 48, 260-61; and Ostlind et al., *Medical and Veterinary Entomology*, 1997, 11, 407-408). The paraherquamide family of compounds is a known class of compounds that include a spirodioxepino indole core with activity against certain parasites (see *Tet. Lett.* 1981, 22, 135; *J. Antibiotics* 1990, 43, 1380, and *J. Antibiotics* 1991, 44, 492). In addition, the structurally related marcfortine family of compounds, such as marcfortines A-C, are also known and may be combined with the compositions of the invention (see *J. Chem. Soc.—Chem. Comm.* 1980, 601 and *Tet. Lett.* 1981, 22, 1977). Further references to the paraherquamide derivatives can be found, for example, in WO 91/09961, WO 92/22555, WO 97/03988, WO 01/076370, WO 09/004432, U.S. Pat. Nos. 5,703,078 and 5,750,695, all of which are hereby incorporated by reference in their entirety.

In general, the additional active agent is included in the long-acting compositions of the present invention in an amount of between about 0.1 µg and about 1000 mg. More typically, the additional active agent may be included in an amount of about 10 µg to about 500 mg, about 1 mg to about 300 mg, about 10 mg to about 200 mg or about 10 mg to about 100 mg.

In other embodiments of the invention, the additional active agent may be included in the composition to deliver a dose of about 5 µg/kg to about 50 mg/kg per weight of the animal. In other embodiments, the additional active agent may be present in an amount sufficient to deliver a dose of about 0.01 mg/kg to about 30 mg/kg, about 0.1 mg/kg to about 20 mg/kg, or about 0.1 mg/kg to about 10 mg/kg of weight of animal. In other embodiments, the additional active agent may be present in a dose of about 5 µg/kg to about 200 µg/kg or about 0.1 mg/kg to about 1 mg/kg of weight of animal. In still another embodiment of the invention, the additional active agent is included in a dose between about 0.5 mg/kg to about 50 mg/kg.

The long-acting compositions of the present invention, which include at least an isoxazoline active agent, at least one liquid PEG and/or a neutral oil and optionally a co-solvent, have been surprisingly discovered to be stable and effective against a broad spectrum of ectoparasites, and possibly also endoparasites if another active is included, for an extended period of time; e.g., a period from three (3) to six (6) months while exhibiting favorable properties with respect to the site of injection.

Liquid PEGs as provided for herein are those polyethylene glycols that are liquid at room temperature (20-30° C.). Polyethylene glycols have the following structural formula:

H—(O—CH$_2$—CH$_2$)$_n$—OH.

Non-limiting examples for n in the above formula are those compounds when n is from 1 to about 10,000 (e.g., from about 4 to about 25). Liquid PEGs include combinations of different polyethylene glycols. Non-limiting examples of liquid PEGs include PEG 200, PEG 300, PEG 400, PEG 600, and PEG 1000 or combinations thereof.

Pharmaceutically acceptable polymers other than PEGs are specifically excluded from the inventive long-acting compositions. Examples of pharmaceutically acceptable polymers that are specifically excluded from the inventive long-acting compositions include polylactides, polyglycolides, polycaprolactones, polyanhydrides, polyamides, polyurethanes, polyester amides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(amino acids), poly(methyl vinyl ether), poly(maleic anhydride), chitin, chitosan, and copolymers, terpolymers, or combinations or mixtures therein including copolymers of polylactides, polycaprolactones, polyglycolides (e.g., poly(lactide-co-glycolide).

In some embodiments, poloxamers may be included in the compositions. For the purpose of the compositions described herein, poloxamers are not considered pharmaceutically-acceptable polymers but solvents or surfactants. Poloxamers are a family of synthetic block copolymers of ethylene oxide and propylene oxide. Poloxamers may be liquid, a milky white paste or a powder and are represented by the following structure:

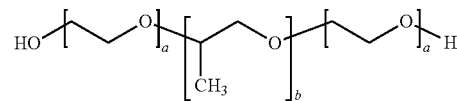

where a is an integer between 2 and 130 and b is an integer between 15 and 67 (see, U.S. Pat. No. 3,740,421, incorporated herein by reference). Poloxamer are available from commercial sources such as BASF and Croda. An example of a poloxamer that may be used in the compositions of the invention is P-124 which is a solid at room temperature. The viscosity of the long-acting injectable compositions is an important parameter with respect to the ability to easily administer the composition to animals. Typically, viscosities of about less than 150 centipois (cPs) are acceptable. Thus, in one embodiment, the viscosity of the compositions of the invention at 25° C. is about less than 150 cPs. In other embodiments, the viscosity of the compositions of the invention are 25° C. is about less than 140 cPs, less than about 130 cPs or less than about 120 cPs. In other embodiments, the viscosity of the compositions of the invention at 25° C. is about less than 110 cPs or less than about 100 cPs.

The co-solvents used in the long-acting injectable compositions may be a single or a blend of co-solvents. Co-solvents may be used in the compositions of the invention to improve the solubility of the isoxazoline active agent and/or to lower the viscosity of the compositions. In one embodiment, the co-solvents used in the long-acting injectable compositions of the present invention include polar solvents that are miscible in water. Non-limiting examples of these co-solvents include ethanol, isopropanol, glycol ethers (e.g., including, but limited to, diethyleneglycol monoethyl ether (DGME, Transcutol®), butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), propylene glycol, glycerin, carbonates (e.g., propylene carbonate or ethylene carbonate), 2-pyrrolidone, substituted 2-pyrrolidones including N-methylpyrrolidone, 1-ethylpyrrolidone, 1-octylpyrrolidone, 1-dodecylpyrrolidone, 1-isopropylpyrrolidone, 1-(sec- or t- or n-butyl)pyrrolidone, 1-hexylpyrrolidone, 1-vinyl-2-pyrrolidone, 1-cyclohexylpyrrolidone, 1-(2-hydroxyethyl)-pyrrolidone, 1-(3-hydroxypropyl)pyrrolidone, 1-(2-methoxyethyl)-pyrrolidone, 1-(3-methoxypropyl)pyrrolidone and 1-benzylpyrrolidone; dimethyl isosorbide (DMI), dimethylacetamide (DMA), dimethylsulfoxide (DMSO), glycerol formal or a mixture of at least two of these solvents.

In one embodiment, the long-acting compositions of the invention comprise a polar protic solvent including, but not limited to, an alcohol such a $C_1$-$C_6$alcohol including, but not limited to, ethanol, isopropanol. In another embodiment, the polar protic solvent is a glycol, such as glycerol or propylene glycol, or a glycol ether such as diethylene glycol monoethyl ether (Transcutol) or other commonly used glycol ethers such as those described above.

In another embodiment, the long-acting injectable compositions of the invention comprise a polar aprotic solvent including, but not limited to, N-methylpyrrolidone, dimethyl isosorbide, dimethylacetamide, dimethylsulfoxide or propylene carbonate.

In yet another embodiment of the invention, the compositions of the invention include non-water miscible co-solvents or solvents with only partial solubility in water. Non-water miscible solvents include esters of aliphatic carboxylic acids (including fatty acids) and glycerol (glycerides) or esters of aliphatic carboxylic acids (including fatty acids) and propylene glycol. Non-water miscible solvents also include oils that are acceptable for injectable compositions. Non-limiting examples of these co-solvents include benzyl alcohol, benzyl benzoate, ethyl acetate, triacetin, lipids, triglycerides including medium chain triglycerides such $C_8$-$C_{10}$ triglycerides such as capric/caprilic triglycerides, propylene glycol derivatives (e.g. propylene glycol monolaurate), caprylocaproyl polyoxyl-8 glycerides (Labrasol) (non-ionic water dispersible surfactant, isopropyl myristate, or a mixture of at least two of these co-solvents.

In one embodiment, the composition of the invention may include pharmaceutically acceptable neutral oils as a main component of the composition or as a co-solvent with the liquid PEG. When a neutral oil us used in combination with a liquid PEG, it may be necessary to use a bridging solvent or a surfactant to ensure miscibility. Some neutral oils are triglycerides of fractionated plant fatty acids with chain lengths of $C_8$ to $C_{10}$, including caprylic/capric triglycerides. Two commercially available products are known as MIGLYOL® 810 and MIGLYOL®812. In another embodiment, the neutral oil is a triglyceride of fractionated plant fatty acids with chain lengths of $C_8$ and $C_{10}$ combined with linoleic acid (about 4-5%). A commercially available product is known as MIGLYOL® 818. In yet another embodiment, the neutral oil is a glycerin ester of fractionated plant fatty acids with chain lengths of $C_8$ and $C_{10}$ combined with succinic acid. A commercially available product is known as MIGLYOL® 829. In another embodiment, the neutral oil may be a propylene glycol diester of saturated plant fatty acids with chain lengths of $C_8$ and $C_{10}$. A commercially available product is known as MIGLYOL® 840 (propylene glycol dicaprylate/dicaprate). In yet another embodiment, the co-solvent may be a mixture of two or more neutral oils. Other oils that are acceptable to include in the long-acting injectable compositions of the invention include, but are not limited to, castor oil, cottonseed oil, sesame oil, soybean oil and safflower oil.

In one embodiment, the compositions of the invention may comprise about 0.5% to about 70% (w/v) of a co-solvent. In another embodiment, the compositions of the invention may comprise about 0.5% to about 60% (w/v) or about 1 to about 50% (w/v) of a co-solvent. In still another embodiment, the compositions may comprise about 1% to about 40% (w/v), about 5% to about 50% (w/v), about 5% to about 40% (w/v) or about 5% to about 35% (w/v) of a co-solvent. In other embodiments, the compositions of the invention may comprise about 1% to about 20% (w/v), about 2% to about 15% (w/v) or about 2% to about 10% (w/v) of the co-solvent.

The long-acting injectable compositions of the invention may include pharmaceutically acceptable additives or excipients. Pharmaceutically acceptable additives and excipients include, but are not limited to, surfactants, anti-oxidants, preservatives, pH stabilizing agents (e.g. buffers), and other non-active excipients. In another embodiment, the compositions of the invention may comprise about 0.01% to about 20% (w/v) of a pharmaceutically acceptable additive, excipient or mixtures thereof. In other embodiments, the compositions may comprise about 0.01% to about 5% (w/v), about 0.1% to about 10% (w/v) or about 0.1% to about 5% (w/v) of a pharmaceutically acceptable additive, excipient or mixtures thereof. In other embodiments the compositions may comprise about 5 to about 15% (w/v) or about 5 to about 10% (w/v) of a pharmaceutically acceptable additive, excipient or mixtures thereof. In yet another embodiment, the compositions may comprise about 7 to about 10% of a pharmaceutically acceptable additive, excipient or mixtures thereof.

Surfactants may be present in the inventive compositions at concentrations of about 0.1% to about 10% (w/w), about 1% to about 10% (w/w) or about 5% to about 10% (w/w). More typically, surfactants may be present at concentrations of about 0.1% to about 5% (w/w) or about 1 to about 5% (w/w). Examples of surfactants that may be used in the compositions include, but are not limited to, glyceryl monooleate, polyoxyethylene sorbitan fatty acid esters, sorbitan esters including sorbitan monooleate (Span® 20), polyvinyl alcohol, polysorbates including polysorbate 20 and polysorbate 80, d-α-tocopherol polyethylene glycol 1000 succinate (TPGS), sodium lauryl sulfate, co-polymers of ethylene oxide and propylene oxide (e.g. poloxamers such as LUTROL® F87 and the like), polyethylene glycol castor oil derivatives including polyoxyl 35 castor oil (Cremophor® EL), polyoxyl 40 hydrogenated castor oil (Cremophor® RH 40), polyoxyl 60 hydrogenated castor oil (Cremophor® RH60); propylene glycol monolaurate (LAUROGLYCOL®); glyceride esters including glycerol caprylate/caprate (CAPMUL® MCM), polyglycolized glycerides (GELUCIRE®), PEG 300 caprylic/capric glycerides (Softigen® 767), PEG 400 caprylic/capric glycerides (Labrasol®), PEG 300 oleic glycerides (Labrafil® M-1944CS), PEG 300 linoleic glycerides (Labrafil® M-2125CS); polyethylene glycol stearates and polyethylene glycol hydroxy stearates including polyoxyl 8 stearate (PEG 400 monostearate), polyoxyl 40 stearate (PEG 1750 monostearate, and the like). Polyethylene glycol stearates (synonyms include macrogol stearates, polyoxylstearates, polyoxyethylene stearates, ethoxylated stearates; CAS No. 9004-99-3, 9005-08-7) are mixtures of mono- and distearate esters of mixed polyoxyethylene polymers. Polyethylene glycol hydroxystearate is a mixture of mono- and diesters of hydroxystearic acid with polyethylene glycols. One polyethylene glycol hydroxystearate that may be used in the compositions is polyethylene glycol 12-hydroxystearate. In another embodiment, the inventive compositions may include the surfactant polyethylene glycol 15 12-hydroxystearate (Kolliphor® HS 15 from BASF), a mixture of mono- and diesters of 12-hydroxystearic acid with 15 moles of ethylene oxide. Again, these compounds, as well as their amounts are well known in the art. In another embodiment of the invention, the inventive compositions may include polyoxyl 35 castor oil (Kolliphor® EL) as a surfactant. In other embodiments, the inventive compositions may include polyoxyl 40 hydrogenated castor oil (Kolliphor® RH 40) or polyoxyl 60 hydrogenated castor oil as surfactants. The compositions of the invention may also include a combination of surfactants.

The inventive compositions may contain other inert ingredients such as antioxidants, preservatives, or pH stabilizers. These compounds are well known in the composition art. Antioxidants such as vitamin E, alpha tocopherol, ascorbic acid, ascorbyl palmitate, citric acid, fumaric acid, malic acid, sodium ascorbate, sodium metabisulfate, sodium metabisulfite, n-propyl gallate, BHA (butylated hydroxy anisole), BHT (butylated hydroxy toluene), BHA and citric acid, monothioglycerol, tert-butyl hydroquinone (TBHQ), and the like, may be added to the present composition. The antioxidants are generally included in the compositions of the invention in amounts of about 0.01% to about 3%, or from about 0.01 to about 2% (w/v), based upon total weight of the composition (w/w). In another embodiment, the compositions contain about 0.05 to about 1.0% (w/w) of one or a mixture of antioxidants.

Preservatives, such as the parabens (methylparaben and/or propylparaben), are suitably used in the composition in amounts ranging from about 0.01 to about 2.0%, with about 0.05 to about 1.0% being especially preferred. Other preservatives include benzalkonium chloride, benzethonium chloride, benzoic acid, benzyl alcohol, bronopol, butylparaben, cetrimide, chlorhexidine, chlorobutanol, chlorocresol, cresol, ethylparaben, imidurea, methylparaben, phenol, phenoxyethanol, phenylethyl alcohol, phenylmercuric acetate, phenylmercuric borate, phenylmercuric nitrate, potassium sorbate, sodium benzoate, sodium propionate, sorbic acid, thimerosal, and the like. Preferred ranges for these compounds include from about 0.01 to about 5%.

Compounds which stabilize the pH of the composition are also contemplated. Again, such compounds are well known to a practitioner in the art as well as how to use these compounds. Buffering systems include, for example, systems selected from the group consisting of acetic acid/acetate, malic acid/malate, citric acid/citrate, tartaric acid/tartrate, lactic acid/lactate, phosphoric acid/phosphate, glycine/glycimate, tris, glutamic acid/glutamates and sodium carbonate.

Dosage forms may contain from about 0.5 mg to about 5 g of an active agent or a combination of active agents. More typically, the amount of active agent(s) in the compositions of the invention will be from about 1 mg to about 3 g. In another embodiment, the amount of active agent(s) in the compositions will be from about 20 mg to about 3 g. In another embodiment, the amount of active agent(s) present in the compositions will be from about 20 mg to about 2 g, about 20 mg to about 1.5 g or about 20 mg to about 1 g. In other embodiments, the amount of active agent(s) in the compositions will be from about 20 mg to about 500 mg, about 30 mg to about 200 mg or about 50 mg to about 200 mg. In still another embodiment, the amount of active agent(s) present in the compositions will be from about 50 mg to about 2 g, about 50 mg to about 1 g or about 50 mg to about 500 mg. In yet another embodiment of the invention, the about of active agent(s) present will be from about 100 mg to about 2 g, about 100 mg to about 1 g or about 100 mg to about 500 mg.

In another embodiment, the amount of active agent(s) present in the compositions of the invention is from about 1 mg to about 500 mg of an active agent, about 1 mg to about 100 mg or about 1 mg to about 25 mg. In still other embodiments, the amount of the active agent present in the compositions is about 10 mg about 50 mg or about 10 mg to about 100 mg. In other embodiments, the amount of active agent present in the compositions is about 50 mg to about 200 mg, about 100 mg to about 300 mg, about 100 mg to about 400 mg, about 200 mg to about 500 mg, about 300 mg to about 600 mg, about 400 mg to about 800 mg, or about 500 mg to about 1000 mg.

The compositions of the invention are made by mixing the appropriate amount of the active agents, a liquid PEG and/or a neutral oil, a co-solvent (if present) and, optionally, an antioxidant, pharmaceutically acceptable additive and/or excipient to form a composition of the invention. In some embodiments the compositions of the present invention can be obtained by following the method of making these forms described above by the description of making these forms found in general composition text known to those in the art, e.g. *Remington—The Science and Practice of Pharmacy* ($21^{st}$ *Edition*) (2005), *Goodman & Gilman's The Pharmacological Basis of Therapeutics* ($11^{th}$ *Edition*) (2005) and *Ansel's Pharmaceutical Dosage Forms and Drug Delivery Systems* ($8^{th}$ *Edition*), edited by Allen et al., Lippincott Williams & Wilkins, (2005).

Methods of Treatment

In another aspect of the invention, a method for preventing or treating a parasite infestation/infection in an animal is provided, comprising administering to the animal a long-acting injectable composition comprising an effective amount of at least one isoxazoline compound, a liquid PEG and/or a neutral oil, optionally a co-solvent, and optionally, an antioxidant, pharmaceutically acceptable additive and/or excipient. The compositions of the invention have long-lasting efficacy against ectoparasites (e.g. fleas and ticks) and in certain embodiments may also be active against endoparasites that harm animals.

In one embodiment of the invention, methods for the treatment or prevention of a parasitic infestation or infection in a livestock animal are provided, which comprise administering a long-acting injectable composition comprising an effective amount of at least one isoxazoline active agent to the animal. Ectoparasites against which the methods and compositions of the invention are effective include, but are not limited to, fleas, ticks, mites, mosquitoes, flies and lice. In certain embodiments wherein the inventive compositions include one or more additional active agents that are active against internal parasites the compositions and methods of the invention may also be effective against endoparasites including, but not limited to, cestodes, nematodes, hookworms and roundworms of the digestive tract of animals and humans.

In an alternative embodiment of the invention, methods for the treatment or prevention of a parasitic infestation or infection in a domestic animal are provided, which comprise administering a long-acting injectable composition comprising an effective amount of at least one isoxazoline active agent to the animal. Ectoparasites against which the methods and compositions of the invention are effective include, but are not limited to, fleas, ticks, mites, mosquitoes, flies and lice. In certain embodiments wherein the inventive compositions include one or more additional active agents that are active against internal parasites the compositions and methods of the invention may also be effective against endoparasites including, but not limited to, cestodes, nematodes, hookworms and roundworms of the digestive tract of animals and humans.

In one embodiment for treatment against ectoparasites, the ectoparasite is one or more insect or arachnid including those of the genera *Ctenocephalides, Rhipicephalus, Dermacentor, Ixodes, Boophilus, Amblyomma, Haemaphysalis, Hyalomma, Sarcoptes, Psoroptes*, Otodectes, Chorioptes, *Hypoderma, Damalinia, Linognathus, Haematopinus, Solenoptes, Trichodectes*, and *Felicola*.

In another embodiment for the treatment against ectoparasites, the ectoparasite is from the genera *Ctenocephalides, Rhipicephalus, Dermacentor, Ixodes* and/or *Boophilus*. The ectoparasites treated include but are not limited to fleas, ticks, mites, mosquitoes, flies, lice, blowfly and combinations thereof. Specific examples include, but are not limited to, cat and dog fleas (*Ctenocephalides felis, Ctenocephalides* sp., and the like), ticks (*Rhipicephalus* sp., *Ixodes* sp., *Dermacentor* sp., *Amblyomma* sp., and the like), and mites (*Demodex* sp., *Sarcoptes* sp., Otodectes sp., and the like), lice (*Trichodectes* sp., *Cheyletiella* sp., *Linognathus* sp., and the like), mosquitoes (*Aedes* sp., *Culex* sp., *Anopheles* sp., and the like) and flies (*Haematobia* sp., including *Haematobia irritans, Musca* sp., *Stomoxys* sp., including *Stomoxys calcitrans, Dermatobia* sp., *Cochliomyia* sp., and the like).

Additional examples of ectoparasites include but are not limited to the tick genus *Boophilus*, especially those of the species *microplus* (cattle tick), *decoloratus* and *annulatus*; myiasis such as *Dermatobia hominis* (known as Berne in Brazil) and *Cochliomyia hominivorax* (greenbottle); sheep myiasis such as *Lucilia sericata, Lucilia cuprina* (known as blowfly strike in Australia, New Zealand and South Africa). Flies proper, namely those whose adult constitutes the parasite, such as *Haematobia irritans* (horn fly) and *Stomoxys calcitrans* (stable fly); lice such as *Linognathus vituli*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

In some embodiments of the invention, the composition can also be used to treat against endoparasites such as those helminths selected from the group consisting of Anaplocephala, *Ancylostoma, Necator, Ascaris, Capillaria, Cooperia, Dipylidium, Dirofilaria, Echinococcus, Enterobius, Fasciola, Haemonchus, Oesophagostomum, Ostertagia, Toxocara, Strongyloides, Toxascaris, Trichinella, Trichuris*, and *Trichostrongylus*, among others.

In one embodiment, the invention provides methods for the treatment and prevention of parasitic infections and infestations in or on animals (either wild or domesticated), including livestock and companion animals such as cats, dogs, horses, birds including chickens, sheep, goats, pigs, deer, turkeys and cattle, with the aim of ridding these hosts of parasites commonly encountered by such animals.

In an embodiment, the invention provides methods and compositions for the treatment or prevention of parasitic infections and infestations in livestock animals (e.g., sheep and cattle) or companion animals including, but not limited to, cats and dogs. The methods and compositions are particularly effective for preventing or treating parasitic infestations of cattle and sheep with fleas and ticks.

In another embodiment, the methods and compositions of the invention are used for the treatment or prevention of parasitic infections and infestations in cattle or sheep. When treating livestock animals such as cattle or sheep, the methods and compositions are particularly effective against *Rhipicephalus* (*Boophilus*) *microplus, Haematobia irritans* (horn fly), *Stomoxys calcitrans* (stable fly), and sheep myiasis such as *Lucilia sericata, Lucilia cuprina* (known as blowfly strike in Australia, New Zealand and South Africa).

The terms "treating" or "treat" or "treatment" are intended to mean the administration of a long-acting composition of the present invention to an animal that has a parasitic infestation for the eradication of the parasite or the reduction of the number of the parasites infesting the animal undergoing treatment. It is noted that the compositions of the invention may be used to prevent such a parasitic infestation.

The terms "prevent", "prevention" or "prophylaxis" are intended to mean the administration of the long-acting compositions of the present invention to the animal before the parasitic infection or infestation has occurred in order to keep said infection or infestation from occurring. Administration of the long-acting compositions at recommended regular intervals effectively prevents new parasitic infestations or infections in animals by killing new parasites that attack an animal before they can multiply to establish an infestation or infection.

The compositions of the invention are administered in parasiticidally effective amounts which are which are suitable to control the parasite in question to the desired extent, as described below. In each aspect of the invention, the compounds and compositions of the invention can be applied against a single pest or combinations thereof.

By "antiparasitic effective amount" is intended a sufficient amount of a composition of the invention to eradicate or reduce the number of parasites infesting the animal. In some embodiments, an effective amount of the active agent achieves at least 70% efficacy against the target parasite. In other embodiments, an effective amount of the active agent achieves at least 80%, or at least 90% efficacy against the target pests. Preferably, an effective amount of the active agent will achieve at least 95%, at least 98% or 100% efficacy against the target parasites.

Generally, a dose of from about 0.001 to about 100 mg per kg of body weight given as a single dose or in divided doses for a period of from 1 to 5 days will be satisfactory but, of course, there can be instances where higher or lower dosage ranges are indicated, and such are within the scope of this invention. It is well within the routine skill of the practitioner to determine a particular dosing regimen for a specific host and parasite.

In some embodiments for companion animals, the dose of the isoxazoline active agent administered from the topical compositions of the invention is between about 0.1 to about 50 mg per kg of body weight. More typically the dose of the isoxazoline active agent administered is about 0.5 to about 30 mg/kg or about 0.5 to about 30 mg/kg body weight. In yet another embodiment, the dose of the isoxazoline active agent will be from about 0.5 to about 20 mg/kg, about 0.5 to about 10 mg/kg or about 0.5 to about 5 mg/kg body weight. In another embodiment, the dose will be from about 0.5 to about 2.5 mg/kg body weight. In another embodiment, the dose of the isoxazoline active agent administered is about 10 to about 30 mg/kg, about 15 to about 30 mg/kg or about 20 to about 30 mg/kg of body weight.

In other embodiments, the dose administered may be lower depending on the animal and the isoxazoline administered. For example, if the composition comprises the more active enantiomer of the isoxazoline compounds a lower dose may be administered. In some embodiments, the dose is from about 0.1 to about 30 mg/kg of body weight. In another embodiment, the dose may be from about 0.1 to about 20 mg/kg or about 0.1 to about 10 mg/kg of body weight. In another embodiment, a dose of from about 0.1 to about 5 mg/kg, from about 0.1 to about 2.5 mg/kg body weight will be used. In other embodiments, the dose may be from about 1 to about 20 mg/kg of body weight or about 1 to about 10 mg/kg. In yet another embodiment, the dose may be from about 5 to about 20 mg/kg or about 10 to about 20 mg/kg of body weight.

The volume of the dose of the long-acting injectable compositions is typically less than about 10 mL/50 kg body weight of the animal being treated. In other embodiments, the injection volume is about 7 mL/50 kg body weight. In yet other embodiments, the injection volume is less than about 5 mL/50 kg, less than about 3 mL/50 kg body weight or less than about 2 mL/50 kg of body weight. In yet other embodiments, the injection volume is from about 0.1 to about 2 mL/50 kg body weight of the animal. In other embodiments, the injection volume is about 0.05 to about 1 mL/50 kg body weight of the animal.

In other embodiments for the treatment of livestock animals such as cattle or sheep, doses of the isoxazoline active agent administered may be about 0.1 to about 40 mg/kg of body weight. More typically the doses administered will be about 1 to about 30 mg/kg, about 1 to about 20 mg/kg or about 1 to about 10 mg/kg of bodyweight. In yet another embodiment, the dose may be from about 10 to about 25 mg/kg, about 15 to about 30 mg/kg of body weight or about 20-30 mg/kg of body weight.

In one embodiment of the method of use in livestock animals (e.g., cattle or sheep), the long-acting compositions of the present invention comprising an isoxazoline compound has an efficacy against ectoparasites including, but not limited to, fleas, ticks, mites, and parasitic flies, of at least about 90.0% or higher for about 3 months, or longer. In another embodiment, the long-acting compositions of the present invention provide an efficacy against ectoparasites of at least 95.0% or higher for about 3 months or longer.

In another embodiment, the long-acting compositions of the present invention provide an efficacy against ectoparasites in livestock animals (e.g., cattle or sheep) of at least about 80% for two months, or longer. In another embodiment, the long-acting compositions of the present invention efficacy against ectoparasites in livestock animals (e.g., cattle or sheep) of about 90% for at least about 2 months. In still another embodiment, the compositions provide an efficacy of about 95% for about 2 months or longer. In another embodiment, the long-acting compositions of the present invention efficacy against ectoparasites in livestock animals (e.g., cattle or sheep) of about 90% for about 3 months, or longer. In still another embodiment, the compositions provide an efficacy of about 95% for about 3 months or longer.

In another embodiment, the long-acting compositions of the present invention have an efficacy of at least about 80% against ectoparasites for about 3 months, or longer. In still another embodiment, the long-acting compositions of the invention provide an efficacy of at least about 90% against ectoparasites for 3 months or longer. In yet another embodiment, the long-acting compositions of the present invention of the invention provide an efficacy of at least about 95% against ectoparasites for 3 months or longer. In still another embodiment, the long-acting compositions of the present invention provide an efficacy against ectoparasites in livestock animals (e.g., cattle or sheep) of at least 80% or at least 90% for about 3 months to about 6 months or longer.

In other embodiments, the long-acting compositions of the invention have an efficacy of at least about 90% against ectoparasites including, but not limited to, fleas, ticks, mites and parasitic flies, of about 7 months or longer, about 8 months or longer or about 9 months or longer. In other embodiments, the long-acting compositions of the invention have an efficacy of at least about 90% against ectoparasites including, but not limited to, fleas, ticks, mites and parasitic flies, of about 10 months or longer, about 118 months or longer or even about 12 months or longer.

In another aspect of the invention, a kit for the treatment or prevention of a parasitic infestation in an animal is provided, which comprises a long-acting composition of the invention and a syringe.

Antiparasitic Compounds

In a second aspect of the invention, novel and inventive pesticidal and parasiticidal isoxazoline compounds of formula (Id) are provided:

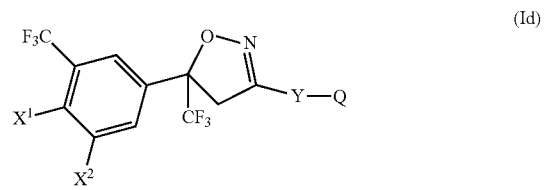

(Id)

wherein $X^1$ is bromo, chloro, iodo or fluoro; and $X^2$ is chloro, fluoro or $CF_3$;

Y is a group Y-1, Y-2, Y-3, Y-4 where Z is N or CH, Y-5 or Y-6

Y-1

Y-2

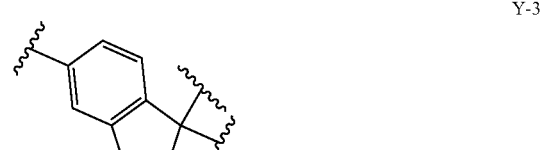

Y-3

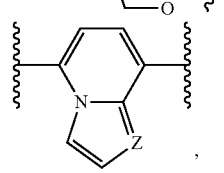

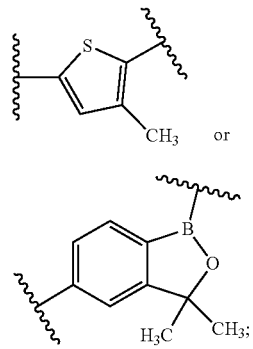

Y-5

Y-6

Q is OH, —C(O)NHCH$_2$C(O)NHCH$_2$CF$_3$, —C(O)CH$_2$S(O)$_2$CH$_3$,
—C(O)NHCH$_2$CH$_2$SCH$_3$ or (—CH$_2$—)(—CH$_2$-)N(CO)CH$_2$S(O)$_2$CH$_3$.

The second aspect of the present invention includes at least the following features:

(a) In one embodiment, the invention provides novel compounds of formula (Id), or pharmaceutically or agriculturally acceptable salts thereof, which are active against arthropod pests and parasites that harm animals and plants;

(b) veterinary and pesticidal compositions for combating and controlling pests and parasites comprising a pesticidally or parasiticidally effective amount of the compounds of formula (Id), or pharmaceutically or agriculturally acceptable salts thereof, in combination with a pharmaceutically or agriculturally acceptable carrier or diluent;

(c) plant propagation material (e.g. seed), comprising at least one compound of formula (Id), or agriculturally acceptable salts thereof.

(d) veterinary and pesticidal compositions for combating arthropod pests and parasites comprising a pesticidally or parasiticidally effective amount of the compounds of the invention, or pharmaceutically or agriculturally acceptable salts thereof, in combination with at least one additional active agent and a pharmaceutically or agriculturally acceptable carrier or diluent;

(e) methods for treating a parasitic infestation/infection in or on an animal are provided, which methods comprise administering a parasiticidally effective amount of a compound of formula (Id), or pharmaceutically acceptable salts thereof, to the animal in need thereof;

(f) methods for the prevention of a parasitic infestation/infection of an animal, which comprise administering a parasiticidally effective amount of a compound of formula (Id), or pharmaceutically acceptable salts thereof, to the animal in need thereof;

(g) methods for combating or controlling pests that are detrimental to crops, plants, plant propagation material, or material containing wood or derived from wood, comprising contacting the crop, plants, plant propagation material, or material containing wood or derived from wood, with a pesticidally effective amount of a compound of formula (Id), or an agriculturally acceptable salt thereof, or a composition comprising the compounds;

(h) methods for combating or controlling pests at a locus, comprising administering a pesticidally or parasiticidally effective amount of a compound of formula (Id), or pharmaceutically or agriculturally acceptable salts thereof, to the locus;

(i) use of the compounds of formula (Id), or pharmaceutically or agriculturally acceptable salts thereof, for controlling pests, including parasites, in or on an animal or on crops, plants, plant propagation material, or material containing wood or derived from wood; and (j) use of the compounds of formula (Id), or pharmaceutically acceptable salts thereof, in the manufacture of a veterinary medicament for controlling pests, including parasites.

An important aspect of the invention is to provide isoxazoline active agents that exhibit surprising and unexpected fast-acting and long-lasting efficacy against parasites, particularly ticks, than isoxazoline active compounds having different substitution patterns on the phenyl ring bound to the quaternary carbon of the isoxazoline ring. Thus, it has been found that the compound of formula (Id) in which Y is Y-2, Q is —C(O)NHCH$_2$C(O)NHCH$_2$CF$_3$, X$^1$ is fluoro and X$^2$ is chloro, which is not specifically described in WO 2007/079162 A1 or WO 2009/002890 A2, has been found to have surprisingly improved duration of activity against the tick *Rhipicephalus microplus* (formerly *Boophilus microplus*) on cattle compared with known isoxazoline compounds in which Y is Y-2 and Q is —C(O)NHCH$_2$C(O)NHCH$_2$CF$_3$ but having different substitution patterns on the phenyl ring.

Furthermore, the compound of formula (Id) in which Y is Y-2, Q is —C(O)NHCH$_2$C(O)NHCH$_2$CF$_3$, X$^1$ is fluoro and X$^2$ is chloro, has also been found to have surprisingly improved fast-acting efficacy against the tick *Rhipicephalus microplus* on cattle compared with known isoxazoline compounds in which Y is Y-2, Q is Y is Y-2, Q is —C(O)NHCH$_2$C(O)NHCH$_2$CF$_3$ but having different substitution patterns on the phenyl ring.

In one embodiment, the invention provides a compound of formula (Id) wherein the group Y is Y-1. In another embodiment Y is Y-2. In another embodiment, Y is Y-3. In another embodiment, Y is Y-4. In still another embodiment, Y is Y-5. In another embodiment, Y is Y-6.

In one embodiment, the invention provides a compound of formula (Id) wherein Y is Y-1, X$^1$ is fluoro, and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-2, X$^1$ is fluoro, and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-3, X$^1$ is fluoro, and Q is (—CH$_2$—)(—CH$_2$—)N(CO)CH$_2$S(O)$_2$CH$_3$ where each terminal CH$_2$ is bonded to the benzylic carbon of Y-3. In another embodiment, Y is Y-4, X$^1$ is fluoro, and Q is —C(O)NHCH$_2$C(O)NHCH$_2$CF$_3$, —C(O)CH$_2$S(O)$_2$CH$_3$ or —C(O)NHCH$_2$CH$_2$SCH$_3$.

In another embodiment, Y is Y-5, X$^1$ is fluoro, and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In yet another embodiment, Y is Y-6, X$^1$ is fluoro, and Q is OH.

In another embodiment, the invention provides a compound of formula (Id) wherein Y is Y-1, X$^1$ is chloro, and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-2, X$^1$ is chloro, and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-3, X$^1$ is chloro, and Q is (—CH$_2$—)(—CH$_2$—)N(CO)CH$_2$S(O)$_2$CH$_3$ where each terminal CH$_2$ is bonded to the benzylic carbon of Y-3. In another embodiment, Y is Y-4, X$^1$ is chloro, and Q is —C(O)NHCH$_2$C(O)NHCH$_2$CF$_3$, —C(O)CH$_2$S(O)$_2$CH$_3$ or —C(O)NHCH$_2$CH$_2$SCH$_3$.

In another embodiment, Y is Y-5, $X^1$ is chloro, and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In yet another embodiment, Y is Y-6, $X^1$ is chloro, and Q is OH.

In one embodiment, Y is Y-1, $X^1$ is fluoro, $X^2$ is chloro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-1, $X^1$ is fluoro, $X^2$ is fluoro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-1, $X^1$ is fluoro, $X^2$ is CF$_3$ and Q is —C(O)NHCH$_2$C(O)NHCH$_2$CF$_3$, —C(O)CH$_2$S(O)$_2$CH$_3$ or —C(O)NHCH$_2$CH$_2$SCH$_3$.

In another embodiment, Y is Y-1, $X^1$ is chloro, $X^2$ is chloro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-1, $X^1$ is chloro, $X^2$ is fluoro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-1, $X^1$ is chloro, $X^2$ is CF$_3$ and Q is —C(O)NHCH$_2$C(O)NHCH$_2$CF$_3$, —C(O)CH$_2$S(O)$_2$CH$_3$ or —C(O)NHCH$_2$CH$_2$SCH$_3$.

In one embodiment, Y is Y-1, $X^1$ is bromo, $X^2$ is chloro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-1, $X^1$ is bromo, $X^2$ is fluoro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-1, $X^1$ is bromo, $X^2$ is CF$_3$ and Q is —C(O)NHCH$_2$C(O)NHCH$_2$CF$_3$, —C(O)CH$_2$S(O)$_2$CH$_3$ or —C(O)NHCH$_2$CH$_2$SCH$_3$.

In one embodiment, Y is Y-1, $X^1$ is iodo, $X^2$ is chloro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-1, $X^1$ is iodo, $X^2$ is fluoro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-1, $X^1$ is iodo, $X^2$ is CF$_3$ and Q is —C(O)NHCH$_2$C(O)NHCH$_2$CF$_3$, —C(O)CH$_2$S(O)$_2$CH$_3$ or —C(O)NHCH$_2$CH$_2$SCH$_3$.

In one embodiment, Y is Y-2, $X^1$ is fluoro, $X^2$ is chloro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-2, $X^1$ is fluoro, $X^2$ is fluoro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-2, $X^1$ is fluoro, $X^2$ is CF$_3$ and Q is —C(O)NHCH$_2$C(O)NHCH$_2$CF$_3$, —C(O)CH$_2$S(O)$_2$CH$_3$ or —C(O)NHCH$_2$CH$_2$SCH$_3$.

In another embodiment, Y is Y-2, $X^1$ is chloro, $X^2$ is chloro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-2, $X^1$ is chloro, $X^2$ is fluoro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-2, $X^1$ is chloro, $X^2$ is CF$_3$ and Q is —C(O)NHCH$_2$C(O)NHCH$_2$CF$_3$, —C(O)CH$_2$S(O)$_2$CH$_3$ or —C(O)NHCH$_2$CH$_2$SCH$_3$.

In one embodiment, Y is Y-2, $X^1$ is bromo, $X^2$ is chloro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-2, $X^1$ is bromo, $X^2$ is fluoro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-2, $X^1$ is bromo, $X^2$ is CF$_3$ and Q is —C(O)NHCH$_2$C(O)NHCH$_2$CF$_3$, —C(O)CH$_2$S(O)$_2$CH$_3$ or —C(O)NHCH$_2$CH$_2$SCH$_3$.

In one embodiment, Y is Y-2, $X^1$ is iodo, $X^2$ is chloro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-2, $X^1$ is iodo, $X^2$ is fluoro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-2, $X^1$ is iodo, $X^2$ is CF$_3$ and Q is —C(O)NHCH$_2$C(O)NHCH$_2$CF$_3$, —C(O)CH$_2$S(O)$_2$CH$_3$ or —C(O)NHCH$_2$CH$_2$SCH$_3$.

In one embodiment, Y is Y-3, $X^1$ is fluoro, $X^2$ is chloro and Q is (—CH$_2$—)(—CH$_2$—)N(CO)CH$_2$S(O)$_2$CH$_3$ where each terminal CH$_2$ is bonded to the benzylic carbon of Y-3. In another embodiment, Y is Y-3, $X^1$ is fluoro, $X^2$ is fluoro and Q is (—CH$_2$—)(—CH$_2$—)N(CO)CH$_2$S(O)$_2$CH$_3$ where each terminal CH$_2$ is bonded to the benzylic carbon of Y-3. In another embodiment, Y is Y-3, $X^1$ is fluoro, $X^2$ is CF$_3$ and Q is (—CH$_2$—)(—CH$_2$—)N(CO)CH$_2$S(O)$_2$CH$_3$ where each terminal CH$_2$ is bonded to the benzylic carbon of Y-3.

In another embodiment, Y is Y-3, $X^1$ is chloro, $X^2$ is chloro and Q is (—CH$_2$—)(—CH$_2$—)N(CO)CH$_2$S(O)$_2$CH$_3$ where each terminal CH$_2$ is bonded to the benzylic carbon of Y-3. In another embodiment, Y is Y-3, $X^1$ is chloro, $X^2$ is fluoro and Q is (—CH$_2$—)(—CH$_2$—)N(CO)CH$_2$S(O)$_2$CH$_3$ where each terminal CH$_2$ is bonded to the benzylic carbon of Y-3. In another embodiment, Y is Y-3, $X^1$ is chloro, $X^2$ is CF$_3$ and Q is (—CH$_2$—)(—CH$_2$—)N(CO)CH$_2$S(O)$_2$CH$_3$ where each terminal CH$_2$ is bonded to the benzylic carbon of Y-3.

In one embodiment, Y is Y-3, $X^1$ is bromo, $X^2$ is chloro and Q is (—CH$_2$—)(—CH$_2$—)N(CO)CH$_2$S(O)$_2$CH$_3$ where each terminal CH$_2$ is bonded to the benzylic carbon of Y-3. In another embodiment, Y is Y-3, $X^1$ is bromo, $X^2$ is fluoro and Q is (—CH$_2$—)(—CH$_2$—)N(CO)CH$_2$S(O)$_2$CH$_3$ where each terminal CH$_2$ is bonded to the benzylic carbon of Y-3. In another embodiment, Y is Y-3, $X^1$ is bromo, $X^2$ is CF$_3$ and Q is (—CH$_2$—)(—CH$_2$—)N(CO)CH$_2$S(O)$_2$CH$_3$ where each terminal CH$_2$ is bonded to the benzylic carbon of Y-3.

In one embodiment, Y is Y-3, $X^1$ is iodo, $X^2$ is chloro and Q is (—CH$_2$—)(—CH$_2$—)N(CO)CH$_2$S(O)$_2$CH$_3$ where each terminal CH$_2$ is bonded to the benzylic carbon of Y-3. In another embodiment, Y is Y-3, $X^1$ is iodo, $X^2$ is fluoro and Q is (—CH$_2$—)(—CH$_2$—)N(CO)CH$_2$S(O)$_2$CH$_3$ where each terminal CH$_2$ is bonded to the benzylic carbon of Y-3. In another embodiment, Y is Y-3, $X^1$ is iodo, $X^2$ is CF$_3$ and Q is (—CH$_2$—)(—CH$_2$—)N(CO)CH$_2$S(O)$_2$CH$_3$ where each terminal CH$_2$ is bonded to the benzylic carbon of Y-3.

In one embodiment, Y is Y-4, $X^1$ is fluoro, $X^2$ is chloro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-4, $X^1$ is fluoro, $X^2$ is fluoro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-4, $X^1$ is fluoro, $X^2$ is CF$_3$ and Q is —C(O)NHCH$_2$C(O)NHCH$_2$CF$_3$, —C(O)CH$_2$S(O)$_2$CH$_3$ or —C(O)NHCH$_2$CH$_2$SCH$_3$.

In another embodiment, Y is Y-4, $X^1$ is chloro, $X^2$ is chloro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-4, $X^1$ is chloro, $X^2$ is fluoro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-4, $X^1$ is chloro, $X^2$ is CF$_3$ and Q is —C(O)NHCH$_2$C(O)NHCH$_2$CF$_3$, —C(O)CH$_2$S(O)$_2$CH$_3$ or —C(O)NHCH$_2$CH$_2$SCH$_3$.

In one embodiment, Y is Y-4, $X^1$ is bromo, $X^2$ is chloro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-4, $X^1$ is bromo, $X^2$ is fluoro and Q is —C(O)NHCH$_2$C(O)NHCH$_2$CF$_3$, —C(O)CH$_2$S(O)$_2$CH$_3$ or —C(O)NHCH$_2$CH$_2$SCH$_3$. In another embodiment, Y is Y-4, $X^1$ is bromo, $X^2$ is CF$_3$ and Q is —C(O)NHCH$_2$C(O)NHCH$_2$CF$_3$, —C(O)CH$_2$S(O)$_2$CH$_3$ or —C(O)NHCH$_2$CH$_2$SCH$_3$.

In one embodiment, Y is Y-4, $X^1$ is iodo, $X^2$ is chloro and Q is $-C(O)NHCH_2C(O)NHCH_2CF_3$, $-C(O)CH_2S(O)_2CH_3$ or $-C(O)NHCH_2CH_2SCH_3$. In another embodiment, Y is Y-4, $X^1$ is iodo, $X^2$ is fluoro and Q is $-C(O)NHCH_2C(O)NHCH_2CF_3$, $-C(O)CH_2S(O)_2CH_3$ or $-C(O)NHCH_2CH_2SCH_3$. In another embodiment, Y is Y-4, $X^1$ is iodo, $X^2$ is $CF_3$ and Q is $-C(O)NHCH_2C(O)NHCH_2CF_3$, $-C(O)CH_2S(O)_2CH_3$ or $-C(O)NHCH_2CH_2SCH_3$.

In one embodiment, Y is Y-5, $X^1$ is fluoro, $X^2$ is chloro and Q is $-C(O)NHCH_2C(O)NHCH_2CF_3$, $-C(O)CH_2S(O)_2CH_3$ or $-C(O)NHCH_2CH_2SCH_3$. In another embodiment, Y is Y-5, $X^1$ is fluoro, $X^2$ is fluoro and Q is $-C(O)NHCH_2C(O)NHCH_2CF_3$, $-C(O)CH_2S(O)_2CH_3$ or $-C(O)NHCH_2CH_2SCH_3$. In another embodiment, Y is Y-5, $X^1$ is fluoro, $X^2$ is $CF_3$ and Q is $-C(O)NHCH_2C(O)NHCH_2CF_3$, $-C(O)CH_2S(O)_2CH_3$ or $-C(O)NHCH_2CH_2SCH_3$.

In another embodiment, Y is Y-5, $X^1$ is chloro, $X^2$ is chloro and Q is $-C(O)NHCH_2C(O)NHCH_2CF_3$, $-C(O)CH_2S(O)_2CH_3$ or $-C(O)NHCH_2CH_2SCH_3$. In another embodiment, Y is Y-5, $X^1$ is chloro, $X^2$ is fluoro and Q is $-C(O)NHCH_2C(O)NHCH_2CF_3$, $-C(O)CH_2S(O)_2CH_3$ or $-C(O)NHCH_2CH_2SCH_3$. In another embodiment, Y is Y-5, $X^1$ is chloro, $X^2$ is $CF_3$ and Q is $-C(O)NHCH_2C(O)NHCH_2CF_3$, $-C(O)CH_2S(O)_2CH_3$ or $-C(O)NHCH_2CH_2SCH_3$.

In one embodiment, Y is Y-5, $X^1$ is bromo, $X^2$ is chloro and Q is $-C(O)NHCH_2C(O)NHCH_2CF_3$, $-C(O)CH_2S(O)_2CH_3$ or $-C(O)NHCH_2CH_2SCH_3$. In another embodiment, Y is Y-5, $X^1$ is bromo, $X^2$ is fluoro and Q is $-C(O)NHCH_2C(O)NHCH_2CF_3$, $-C(O)CH_2S(O)_2CH_3$ or $-C(O)NHCH_2CH_2SCH_3$. In another embodiment, Y is Y-5, $X^1$ is bromo, $X^2$ is $CF_3$ and Q is $-C(O)NHCH_2C(O)NHCH_2CF_3$, $-C(O)CH_2S(O)_2CH_3$ or $-C(O)NHCH_2CH_2SCH_3$.

In one embodiment, Y is Y-5, $X^1$ is iodo, $X^2$ is chloro and Q is $-C(O)NHCH_2C(O)NHCH_2CF_3$, $-C(O)CH_2S(O)_2CH_3$ or $-C(O)NHCH_2CH_2SCH_3$. In another embodiment, Y is Y-5, $X^1$ is iodo, $X^2$ is fluoro and Q is $-C(O)NHCH_2C(O)NHCH_2CF_3$, $-C(O)CH_2S(O)_2CH_3$ or $-C(O)NHCH_2CH_2SCH_3$. In another embodiment, Y is Y-5, $X^1$ is iodo, $X^2$ is $CF_3$ and Q is $-C(O)NHCH_2C(O)NHCH_2CF_3$, $-C(O)CH_2S(O)_2CH_3$ or $-C(O)NHCH_2CH_2SCH_3$.

In one embodiment, Y is Y-6, $X^1$ is fluoro, $X^2$ is chloro and Q is OH. In another embodiment, Y is Y-6, $X^1$ is fluoro, $X^2$ is fluoro and Q is OH. In another embodiment, Y is Y-6, $X^1$ is fluoro, $X^2$ is $CF_3$ and Q is OH.

In another embodiment, Y is Y-6, $X^1$ is chloro, $X^2$ is chloro and Q is OH. In another embodiment, Y is Y-6, $X^1$ is chloro, $X^2$ is fluoro and Q is OH. In another embodiment, Y is Y-6, $X^1$ is chloro, $X^2$ is $CF_3$ and Q is OH.

In one embodiment, Y is Y-6, $X^1$ is bromo, $X^2$ is chloro and Q is OH. In another embodiment, Y is Y-6, $X^1$ is bromo, $X^2$ is fluoro and Q is OH. In another embodiment, Y is Y-6, $X^1$ is bromo, $X^2$ is $CF_3$ and Q is OH.

In one embodiment, Y is Y-6, $X^1$ is iodo, $X^2$ is chloro and Q is OH. In another embodiment, Y is Y-6, $X^1$ is iodo, $X^2$ is fluoro and Q is OH. In another embodiment, Y is Y-6, $X^1$ is iodo, $X^2$ is $CF_3$ and Q is OH.

In another embodiment, Y is Y-1, $X^1$ is fluoro, $X^2$ is $CF_3$ and Q is $-C(O)NHCH_2C(O)NHCH_2CF_3$. In another embodiment, Y is Y-1, $X^1$ is chloro, $X^2$ is fluoro and Q is $-C(O)NHCH_2C(O)NHCH_2CF_3$.

In one embodiment, Y is Y-2, $X^1$ is fluoro, $X^2$ is chloro and Q is $-C(O)NHCH_2C(O)NHCH_2CF_3$. In another embodiment, Y is Y-1, $X^1$ is chloro, $X^2$ is chloro and Q is $-C(O)NHCH_2C(O)NHCH_2CF_3$.

In one embodiment, Y is Y-3, $X^1$ is fluoro, $X^2$ is chloro and Q is $(-CH_2-)(-CH_2-)N(CO)CH_2S(O)_2CH_3$ where each terminal $CH_2$ is bonded to the benzylic carbon of Y-3. In another embodiment, Y is Y-3, $X^1$ is fluoro, $X^2$ is $CF_3$ and Q is $(-CH_2-)(-CH_2-)N(CO)CH_2S(O)_2CH_3$ where each terminal $CH_2$ is bonded to the benzylic carbon of Y-3.

In one embodiment, Y is Y-4 where Z is CH, $X^1$ is fluoro, $X^2$ is chloro and Q is $-C(O)NHCH_2C(O)NHCH_2CF_3$. In another embodiment, Y is Y-4 where Z is CH, $X^1$ is fluoro, $X^2$ is fluoro and Q is $-C(O)NHCH_2C(O)NHCH_2CF_3$. In yet another embodiment, Y is Y-4, $X^1$ is fluoro, $X^2$ is $CF_3$ and Q is $-C(O)NHCH_2C(O)NHCH_2CF_3$.

In another embodiment, Y is Y-4, $X^1$ is chloro, $X^2$ is chloro and Q is $-C(O)NHCH_2C(O)NHCH_2CF_3$. In another embodiment, Y is Y-4, $X^1$ is chloro, $X^2$ is fluoro and Q is $-C(O)NHCH_2C(O)NHCH_2CF_3$. In another embodiment, Y is Y-4, $X^1$ is chloro, $X^2$ is $CF_3$ and Q is $-C(O)NHCH_2C(O)NHCH_2CF_3$.

In one embodiment, Y is Y-5, $X^1$ is fluoro, $X^2$ is chloro and Q is $-C(O)NHCH_2C(O)NHCH_2CF_3$. In another embodiment, Y is Y-5, $X^1$ is fluoro, $X^2$ is fluoro and Q is $-C(O)NHCH_2C(O)NHCH_2CF_3$. In another embodiment, Y is Y-5, $X^1$ is fluoro, $X^2$ is $CF_3$ and Q is $-C(O)NHCH_2C(O)NHCH_2CF_3$.

In another embodiment, Y is Y-5, $X^1$ is chloro, $X^2$ is chloro and Q is $-C(O)NHCH_2C(O)NHCH_2CF_3$. In another embodiment, Y is Y-5, $X^1$ is chloro, $X^2$ is fluoro and Q is $-C(O)NHCH_2C(O)NHCH_2CF_3$. In another embodiment, Y is Y-5, $X^1$ is chloro, $X^2$ is $CF_3$ and Q is $-C(O)NHCH_2C(O)NHCH_2CF_3$.

In a preferred embodiment, the invention provides a compound of formula (Ie) shown below, or a pharmaceutically or pharmaceutically acceptable salt thereof:

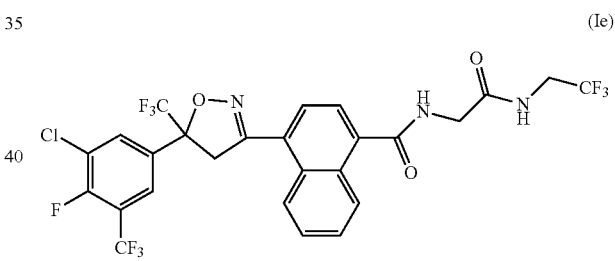

(Ie)

As noted above, the isoxazoline compounds of formula (Id) can exist as stereoisomers since there is a chiral center in the molecule. The individual stereoisomers are encompassed by the structural formulas depicted herein. The various stereoisomers include enantiomers, diastereomers and atropisomers.

Hence, in another embodiment, the invention provides isoxazoline compounds of formula (Id), and compositions comprising the compounds, which are enriched in one enantiomer, or a pharmaceutically or agriculturally acceptable salt thereof.

In another embodiment, the invention provides isoxazoline compounds of formula (Id), and compositions comprising the compounds, which are enriched an enantiomer that displays significant in vitro and in vivo activity with a favorable toxicity profile (the eutomer), or a pharmaceutically acceptable salt thereof.

In one embodiment of the invention, the more biologically active enantiomer of the compound of formula (Id) is believed to be compound of formula (S)-Id shown below. Accordingly, the more biologically active enantiomers of isoxazoline compounds of formulae (Id) wherein Y is Y-1, Y-2, Y-3, Y-4, Y-5 and Y-6 have the (S) configuration at the chiral carbon of the isoxazoline ring.

In an embodiment, the compounds of formulae formula (Id) (including (Ie)), or compositions comprising the compounds, are enriched in one enantiomer over the other enantiomer in a weight:weight ratio of at least 1.5:1. In another embodiment, the compounds of formula (Id) and compositions comprising the compounds are enriched in one enantiomer in a weight:weight ratio of at least 2:1, at least 5:1, at least 10:1 or at least 20:1.

In another embodiment, the compounds of formula (Id), or compositions comprising the compounds, are essentially pure enantiomers. In one embodiment, the compounds and composition of the invention comprises a compound of formula (Id) that is substantially enriched in an enantiomer. The term "substantially enriched" is meant wherein the weight:weight ratio is at least about 1.5:1 or higher in favor of the desired enantiomer. In another embodiment, the compounds and compositions of the invention are substantially enriched in the (S)-enantiomer. In another embodiment, the compounds and compositions of the invention are substantially enriched in the (R)-enantiomer.

In another embodiment of the invention, the compounds of formula (Id), or compositions comprising the compounds, are enriched in the (S)-enantiomer in a weight:weight ratio of at least about 2:1, (S) to (R), or greater. In yet another embodiment, the compounds or compositions of the invention comprise a compound of formula (Id) that is enriched in the (S)-enantiomer in a weight:weight ratio of at least about 5:1, (S) to (R), or greater. In still another embodiment, the compounds and compositions of the invention comprise a compound of formula (Id), that is enriched in the (S)-enantiomer in a weight:weight ratio of at least about 10:1, (S) to (R), or greater. In another embodiment, the compounds and compositions of the invention comprise a compound of formula (Id), that is enriched in the (S)-enantiomer in a weight:weight ratio of at least about 20:1, (S) to (R), or greater. In still another embodiment, the compounds and compositions of the invention comprise a compound of formula (Id), that is essentially the pure (S)-enantiomer.

In one embodiment, the invention provides a compound of formula (S)-Ie, or a pharmaceutically or pharmaceutically acceptable salt thereof, shown below:

(S)-Ie

In another embodiment, the invention provides a compound of formula (R)-Ie, or a pharmaceutically or pharmaceutically acceptable salt thereof, shown below:

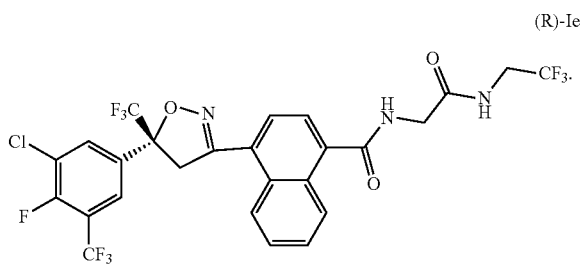 [SMILES: O=C(CNC(=O)c1ccc(C2=NO[C@](c3cc(Cl)c(F)c(C(F)(F)F)c3)(C(F)(F)F)C2)c2ccccc12)NCC(F)(F)F]

(R)-Ie

In another embodiment, the invention provides pesticidal and parasiticidal compositions comprising a compound of formula (S)-Ie. In yet another embodiment, the invention provides pesticidal and parasiticidal compositions comprising a compound of formula (R)-Ie. For the avoidance of doubt, the compositions of the invention comprising a compound of formula (S)-Ie or (R)-Ie may be enriched in the desired enantiomer at the rations discussed above for the compound of formula (Id).

Processes for the Preparation of the Compounds of Formula (Id)

The compounds of formula (Id) and intermediates used in the processes to make the compounds may be prepared by processes adapted from those described in U.S. Pat. Nos. 7,964,204, 8,410,153, 8,546,618, 8,217,180, 8,546,613, 7,662,972, 8,466,115, 8,383,659, 8,853,186, 8,618,126, US 2014/0371464, US 2015/0291612 and WO 2014/090918, all of which are incorporated herein by reference in their entirety.

In one embodiment, the compounds of the invention may be prepared according to the general process shown in Scheme 1 below, wherein Y, Q, $X^1$ and $X^2$ are as defined for formula (Id) above, W is $C_1$, Br or I and R is alkyl.

Scheme 1

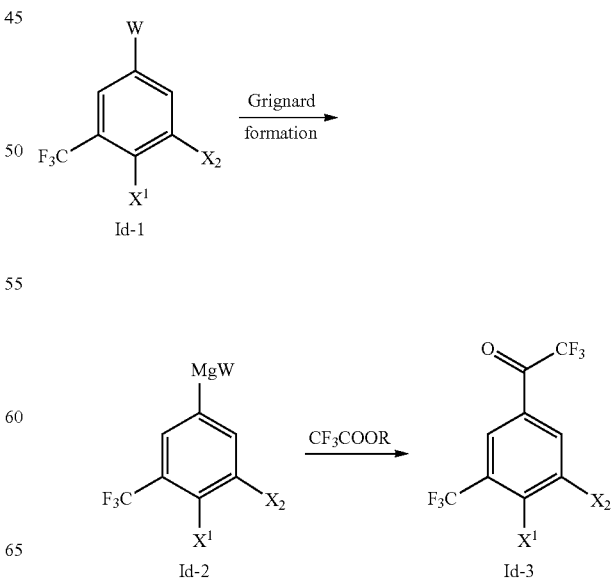

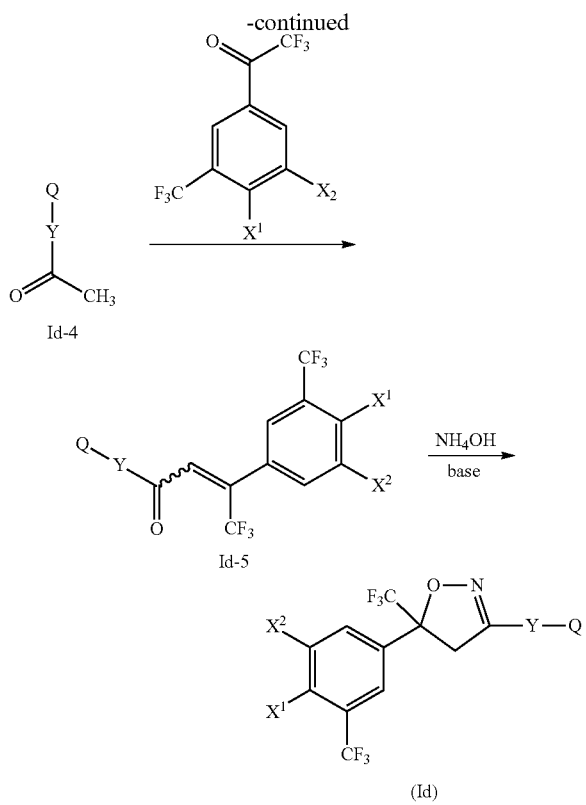

This general process is described, for example, in U.S. Pat. No. 8,546,618 to prepare compounds in which Y is Y-2. Using suitably substituted compounds of formula Id-1 and Id-4, a variety of compounds of formula (Id) may be prepared. Processes for the preparation intermediates of formula Id-1, Id-3, Id-4 and Id-5 are described in U.S. Pat. Nos. 8,546,618 and 8,217,180, both incorporated herein by reference. The formation of isoxazoline compounds of formula (Id) from Id-5 is also described in U.S. Pat. Nos. 8,546,618 and 8,217,180. Additional information on processes for the preparation of intermediates Id-1, Id-3, Id-4 and Id-5 that may be used for the preparation of compounds of formula (Id) is found in U.S. Pat. Nos. 7,662,972, 8,466,115, 8,383,659, 8,853,186, US 2014/0371464, US 2015/0291612 and WO 2014/090918, all incorporated herein by reference in their entirety.

Animal Health Applications
I. Veterinary Compositions:

The compounds of formula (Id) and compositions comprising the compounds are useful for the prevention and treatment of parasitic infestations/infections in animals. The compositions of the invention comprise an effective amount of at least one isoxazoline compound of formula (Id), or a pharmaceutically acceptable salt thereof, in combination with a pharmaceutically acceptable carrier or diluent and optionally other non-active excipients. In a preferred embodiment, the compositions of the invention comprise an effective amount of an isoxazoline of formula (Je) or (S)-Je, or a pharmaceutically acceptable salt thereof. The compositions may be in a variety of solid and liquid forms which are suitable for various forms of application or administration to an animal. For example, the veterinary compositions comprising the inventive compounds may be in compositions suitable for oral administration, injectable administration, including subcutaneous and parenteral administration, and topical administration (e.g. spot-on or pour-on). The compositions are intended to be administered to an animal including, but not limited to, mammals, birds and fish. Examples of mammals include but are not limited to humans, cattle, sheep, goats, llamas, alpacas, pigs, horses, donkeys, dogs, cats and other livestock or domestic mammals. Examples of birds include turkeys, chickens, ostriches and other livestock or domestic birds. The use of the compounds of formula (Id) to protect companion animals, such as dogs and cats, and livestock animals, such as cattle and sheep, from ectoparasites is particularly useful.

As discussed above, the compositions of the invention may be in a form suitable for oral use (see, e.g., U.S. Pat. No. 4,564,631, which is hereby incorporated by reference in its entirety), dietary supplements, troches, lozenges, chewables, tablets, hard or soft capsules, bolus, emulsions, aqueous or oily suspensions, aqueous or oily solutions, oral drench compositions, dispersible powders or granules, premixes, syrups or elixirs, enteric compositions or pastes. Compositions intended for oral use may be prepared according to any method known in the art for the manufacture of pharmaceutical compositions and such compositions may contain one or more sweetening agents, bittering agents, flavoring agents, coloring agents and preserving agents in order to provide pharmaceutically elegant and palatable preparations.

Tablets may contain the active ingredient in admixture with non-toxic, pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. Nos. 4,256,108; 4,166,452; and 4,265,874 (all incorporated herein by reference in their entirety) to form osmotic therapeutic tablets for controlled release.

Oral compositions include hard gelatin capsules, wherein the active ingredient is mixed with an inert solid diluent, for example, calcium carbonate, calcium phosphate or kaolin. Capsules may also be soft gelatin capsules, wherein the active ingredient is mixed with water or miscible solvents such as propylene glycol, PEGs and ethanol, or an oil medium, for example peanut oil, liquid paraffin, or olive oil.

In one embodiment, the compounds of formula (Id) may be administered in chewable tablet compositions or soft chewable compositions such as those described in U.S. Pat. No. 9,233,100 B2, U.S. Pat. No. 9,259,417, US 2010/0087492, US 2006/0222684, US 2004/0151759, U.S. Pat. No. 7,955,632, US 2015/0057321, US 2015/0057239 and WO 2016/073347, all incorporated herein by reference in their entirety.

The veterinary compositions may be in the form of a soft chewable composition ("soft chew") which is palatable and acceptable to the animal. In addition to the active ingredient (S), the soft chews of the invention may include one or more of the following components: a solvent or mixture of solvents, one or more fillers, one or more binders, one or more surfactants, one or more humectants, one or more lubricants, one or more disintegrants, one or more colorants, one or more antimicrobial agents, one or more antioxidants, one or more pH modifiers and one or more flavoring agents.

Solvents that may be used in the compositions of the invention include, but are not limited to, various grades of liquid polyethylene glycol (PEG) including PEG 200, PEG 300, PEG 400 and PEG 540; propylene carbonate; propylene glycol; triglycerides including, but not limited to caprylic/capric triglyceride, caprylic/capric/linoleic triglyceride (e.g. MIGLYOL® 810 and 812, caprylic/capric/succinic triglyceride, propylene glycol dicaprylate/dicaprate, and the like; water, sorbitol solution, glycerol caprylate/caprate and polyglycolized glycerides (GELUCIRE ©), or a combination thereof.

Various fillers known in the art may be used in the soft chewable compositions of the invention. Fillers include, but are not limited to, corn starch, pre-gelatinized corn starch, soy protein fines, corn cob, and corn gluten meal, and the like. In some embodiments, a combination of two or more fillers may be used in the compositions.

Binders that may be used in the compositions of the invention include, but are not limited to, polyvinylpyrrolidone (e.g. Povidone), cross-linked polyvinylpyrrolidone (Crospovidone), polyethylene glycols of various grades including PEG 3350, PEG 4000, PEG 6000, PEG 8000 and even PEG 20,000, and the like; co-polymers of vinylpyrrolidone and vinyl acetate (e.g. Copovidone) such as the product sold by BASF by the tradename Kollidon® VA 64 and the like; starch such as potato starch, tapioca starch or corn starch; molasses, corn syrup, honey, maple syrup and sugars of various types; or a combination of two or more binders.

Humectants that may be used in the compositions include, but are not limited to, glycerol (also referred to herein as glycerin), propylene glycol, cetyl alcohol and glycerol monostearate, and the like. Polyethylene glycols of various grades may also be used as humectants.

Surfactants may be present in the chewable composition at concentrations of about 0.1% to about 10% (w/w), about 1% to about 10% (w/w) or about 5% to about 10% (w/w). More typically, surfactants may be present at concentrations of about 0.1% to about 5% (w/w) or about 1 to about 5% (w/w). Examples of surfactants that may be used in the compositions include, but are not limited to, glyceryl monooleate, polyoxyethylene sorbitan fatty acid esters, sorbitan esters including sorbitan monooleate (Span® 20), polyvinyl alcohol, polysorbates including polysorbate and polysorbate 80, d-α-tocopherol polyethylene glycol 1000 succinate (TPGS), sodium lauryl sulfate, co-polymers of ethylene oxide and propylene oxide (e.g. poloxamers such as LUTROL® F87 and the like), polyethylene glycol castor oil derivatives including polyoxyl 35 castor oil (Cremophor® EL), polyoxyl 40 hydrogenated castor oil (Cremophor® RH 40), polyoxyl 60 hydrogenated castor oil (Cremophor® RH60); propylene glycol monolaurate (LAUROGLYCOL®); glyceride esters including glycerol caprylate/caprate (CAPMUL® MCM), polyglycolized glycerides (GELUCIRE®), PEG 300 caprylic/capric glycerides (Softigen® 767), PEG 400 caprylic/capric glycerides (Labrasol®), PEG 300 oleic glycerides (Labrafil® M-1944CS), PEG 300 linoleic glycerides (Labrafil® M-2125CS); polyethylene glycol stearates and polyethylene glycol hydroxy stearates including polyoxyl 8 stearate (PEG 400 monostearate), polyoxyl 40 stearate (PEG 1750 monostearate, and the like. Polyethylene glycol stearates (synonyms include macrogol stearates, polyoxylstearates, polyoxyethylene stearates, ethoxylated stearates; CAS No. 9004-99-3, 9005-08-7) are mixtures of mono- and distearate esters of mixed polyoxyethylene polymers. Polyethylene glycol hydroxystearate is a mixture of mono- and diesters of hydroxystearic acid with polyethylene glycols. One polyethylene glycol hydroxystearate that may be used in the compositions is polyethylene glycol 12-hydroxystearate. In another embodiment, the compositions may include the surfactant polyethylene glycol 15 12-hydroxystearate (Solutol® HS 15 from BASF), a mixture of mono- and diesters of 12-hydroxystearic acid with 15 moles of ethylene oxide. Again, these compounds, as well as their amounts are well known in the art. In another embodiment of the invention, the compositions may include polyoxyl 35 castor oil (Cremophor® EL) as a surfactant. In other embodiments, the chewable compositions may include polyoxyl 40 hydrogenated castor oil (Cremophor® RH 40) or polyoxyl 60 hydrogenated castor oil (Cremophor® RH60) as surfactants. The compositions of the invention may also include a combination of surfactants.

The chewable compositions may contain other inert ingredients such as antioxidants, preservatives, or pH stabilizers. These compounds are well known in the composition art. Antioxidants may be added to the compositions of the invention to inhibit degradation of the active agents. Suitable antioxidants include, but are not limited to, alpha tocopherol, ascorbic acid, ascorbyl palmitate, fumaric acid, malic acid, sodium ascorbate, sodium metabisulfate, n-propyl gallate, BHA (butylated hydroxy anisole), BHT (butylated hydroxy toluene) monothioglycerol and the like.

The chewable compositions of the invention may also include one or more lubricants and/or processing aids. In some cases, the lubricant/processing aid may also behave as a solvent, and accordingly, there some of the components of the inventive compositions may have dual functions. Lubricants/processing aids include, but are not limited to polyethylene glycols of various molecular weight ranges including PEG 3350 (Dow Chemical) and PEG 4000, corn oil, mineral oil, hydrogenated vegetable oils (STEROTEX or LUBRITAB), peanut oil and/or castor oil.

Many flavoring agents may be used in the compositions of the invention to improve the palatability of the oral veterinary compositions. Preferred flavoring agents are those that are not derived from animal sources. In various embodiments, flavoring components derived from fruit, meat (including, but not limited to pork, beef, chicken, fish, poultry, and the like), vegetable, cheese, bacon, cheese-bacon and/or artificial flavorings may be used. A flavoring component is typically chosen based upon consideration related to the organism that will be ingesting the soft chew. For example, a horse may prefer an apple flavoring component, while a dog may prefer a meat flavoring component. Although flavoring components derived from non-animal sources are preferred, in some embodiments, natural flavors containing beef or liver extracts, etc., may be used such as braised beef flavor artificial powdered beef flavor, roast beef flavor and corned beef flavor among others.

In another embodiment of the invention, the active composition may be administered via an oral drench. Drench compositions are those in which the liquid-containing compositions of the invention are administered to the mouth or throat of the animal.

The compositions of the invention may also be in the form of oil-in-water or water-in-oil emulsions. The oily phase maybe a vegetable oil, for example, olive oil or *arachis* oil, or a mineral oil, for example, liquid paraffin or mixtures of these. Suitable emulsifying agents include naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxyethylene sorbitan monooleate. The emulsions may also contain sweetening agents, bittering agents, flavoring agents, and/or preservatives.

In one embodiment, the composition of the invention may be in the form of a microemulsion. Microemulsions are well suited as the liquid carrier vehicle. Microemulsions are quaternary systems comprising an aqueous phase, an oily phase, a surfactant and a co-surfactant. They are translucent and isotropic liquids.

Microemulsions are composed of stable dispersions of micro droplets of the aqueous phase in the oily phase or conversely of micro droplets of the oily phase in the aqueous phase. The size of these micro droplets may be less than 200 nm (1000 to 100,000 nm for emulsions). The interfacial film may be composed of an alternation of surface-active (SA) and co-surface-active (Co-SA) molecules which, by lowering the interfacial tension, allows the microemulsion to be formed spontaneously.

In one embodiment of the oily phase, the oily phase may be formed from mineral or vegetable oils, from unsaturated polyglycosylated glycerides or from triglycerides, or alternatively from mixtures of such compounds. In one embodiment of the oily phase, the oily phase may be comprised of triglycerides; in another embodiment of the oily phase, the triglycerides are medium-chain triglycerides, for example $C_8$-$C_{10}$ caprylic/capric triglyceride. In another embodiment of the oily phase may represent a % v/v range of about 2 to about 15%; about 7 to about 10%; and about 8 to about 9% v/v of the microemulsion.

The aqueous phase may include, for example water or glycol derivatives, such as propylene glycol, glycol ethers, polyethylene glycols or glycerol. In one embodiment, the glycol may be propylene glycol, diethylene glycol monoethyl ether, dipropylene glycol monoethyl ether or mixtures thereof. Generally, the aqueous phase will represent a proportion from about 1 to about 4% v/v in the microemulsion.

Surfactants for the microemulsion may include diethylene glycol monoethyl ether, dipropylene glycol monomethyl ether, polyglycolide $C_8$-$C_{10}$ glycerides or polyglyceryl-6 dioleate. In addition to these surfactants, the co-surfactants may include short-chain alcohols, such as ethanol and propanol.

Some compounds are common to the three components discussed above, i.e., aqueous phase, surfactant and co-surfactant. However, it is well within the skill level of the practitioner to use different compounds for each component of the same composition. In one embodiment for the amount of surfactant/co-surfactant, the co-surfactant to surfactant ratio will be from about 1/7 to about 1/2. In another embodiment for the amount of co-surfactant, there will be from about 25 to about 75% v/v of surfactant and from about 10 to about 55% v/v of co-surfactant in the microemulsion.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as sucrose, saccharin or aspartame, bittering agents, and flavoring agents may be added to provide a palatable oral preparation. These compositions may be preserved by the addition of an antioxidant such as ascorbic acid, or other known preservatives.

Aqueous suspensions may contain the active material in admixture with excipients suitable for the manufacture of aqueous suspensions. Such excipients include suspending agents, for example, sodium carboxymethylcellulose, methylcellulose, hydroxy-propylmethylcellulose, sodium alginate, polvinylpyrrolidone, gum tragacanth and gum acacia; dispersing or wetting agents include naturally-occurring phosphatide, for example lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide, with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents and/or bittering agents, such as those set forth above.

Dispersible powders and granules suitable for preparation of an aqueous suspension by the addition of water may provide the active ingredient in admixture with a dispersing or wetting agent, suspending agent and one or more preservatives. Suitable dispersing or wetting agents and suspending agents are exemplified by those already mentioned above. Additional excipients, for example, sweetening, bittering, flavoring and coloring agents, may also be present.

Syrups and elixirs may be formulated with sweetening agents, for example, glycerol, propylene glycol, sorbitol or sucrose. Such compositions may also contain a demulcent, a preservative, flavoring agent(S) and/or coloring agent(S).

In another embodiment of the invention, the composition may be in paste form. Examples of embodiments in a paste form include, but are not limited to, those described in U.S. Pat. Nos. 6,787,342 and 7,001,889 (each of which are incorporated herein by reference). In addition to the compounds of the invention, the paste may further contain fumed silica; a viscosity modifier; a carrier; optionally, an absorbent; and optionally, a colorant, stabilizer, surfactant, or preservative.

In one embodiment of the composition, the composition may be a paste containing the compounds of the invention, fumed silica, a viscosity modifier, an absorbent, a colorant; and a hydrophilic carrier which is triacetin, a monoglyceride, a diglyceride, or a triglyceride.

The paste may also include a viscosity modifier. Suitable viscosity modifiers include, but are not limited to, polyethylene glycols (PEG) including, but not limited to, PEG 200, PEG 300, PEG 400, PEG 600; monoethanolamine, triethanolamine, glycerol, propylene glycol, polyoxyethylene (20) sorbitan mono-oleate (polysorbate 80 or Tween 80), or poloxamers (e.g., Pluronic L 81); an absorbent such as magnesium carbonate, calcium carbonate, starch, and cellulose and its derivatives; and a colorant including, but not limited to, titanium dioxide iron oxide, or FD&C Blue #1 Aluminum Lake.

In some embodiments, the compositions may be in the form of a sterile injectable composition. The injectable composition may be a solution in organic solvents or an aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Co-solvents such as ethanol, propylene glycol, glycerol formal or polyethylene glycols may also be used. Preservatives, such as phenol or benzyl alcohol, may be used.

In addition, sterile, fixed oils may be conventionally employed as a solvent or suspending medium. For this purpose any bland fixed oil may be employed including synthetic mono- or diglycerides. In addition, fatty acids such as oleic acid find use in the preparation of injectables.

In another embodiment, the present invention provides for long-acting injectable compositions comprising an isoxazoline compound of formula (Id), a poloxamer and, optionally, a co-solvent. The long-acting compositions comprising an isoxazoline compound of formula (Id), a poloxamer and a co-solvent, have been surprisingly discovered to be stable and effective against a broad spectrum of ectoparasites, and possibly also endoparasites if another active is included, for an extended period of time; e.g., a period from three (3) to six (6) months or longer while exhibiting favorable properties with respect to the site of injection.

Poloxamers are a family of synthetic block copolymers of ethylene oxide and propylene oxide. Poloxamers may be liquid, a milky white paste or a powder and are represented by the following structure:

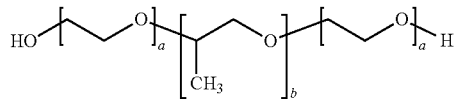

where a is an integer between 2 and 130 and b is an integer between 15 and 67 (see, U.S. Pat. No. 3,740,421). Poloxamer are available from commercial sources such as BASF and Croda. An example of a poloxamer is P-124 which is a solid at room temperature. In one embodiment, poloxamer P-124 has the values a=12 and b=20. Other poloxamers include P-128 (a=38 and b=29), P-181 (a=3 and b=30) P-188 (a=80 and b=27), P-237 (a=64 and b=37), P338 (a=141 and b=44) and P407 (a=101 and b=56).

The co-solvents used in the long-acting injectable compositions comprising a compound of formula (Id) and a poloxamer may be a single or a blend of co-solvents. In one embodiment, the co-solvents used in the long-acting injectable compositions of the present invention include polar solvents that are miscible in water. Non-limiting examples of these co-solvents include ethanol, isopropanol, benzyl alcohol, glycol ethers (e.g., including, but limited to, diethyleneglycol monoethyl ether (DGME, Transcutol®), butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), liquid polyethylene glycols (PEGs) (for example, PEG 400), propylene glycol, carbonates (e.g., propylene carbonate), 2-pyrrolidone, N-methylpyrrolidone, dimethyl isosorbide (DMI), dimethylacetamide, dimethylsulfoxide, glycerol formal or a mixture of at least two of these solvents.

In one embodiment, the long-acting compositions of the invention comprise a polar protic solvent including, but not limited to, an alcohol such as ethanol, isopropanol or a glycol or glycol ether. In another embodiment, the long-acting injectable compositions of the invention comprise a polar aprotic solvent such as N-methylpyrrolidone, dimethyl isosorbide, dimethylacetamide, dimethylsulfoxide or propylene carbonate.

In yet another embodiment of the invention, the long-acting injectable compositions of the invention include non-water miscible co-solvents. Non-limiting examples of these co-solvents include benzyl benzoate, ethyl acetate, triacetin, lipids, triglycerides including medium chain triglycerides such as $C_8$-$C_{10}$ triglycerides such as capric/caprilic triglycerides, propylene glycol derivatives (e.g. propylene glycol monolaurate), caprylocaproyl polyoxyl-8 glycerides (Labrasol) (non-ionic water dispersible surfactant, isopropyl myristate, or a mixture of at least two of these co-solvents. In one embodiment, the compositions include a protic solvent that is not completely miscible with water including, but not limited to, benzyl alcohol.

In another embodiment, the long-acting injectable composition of the invention may include neutral oils as a co-solvent. Neutral oils are triglycerides of fractionated plant fatty acids with chain lengths of $C_8$ to $C_{10}$. Two commercially available products are known as MIGLYOL® 810 and MIGLYOL®812. In another embodiment, the neutral oil is a triglyceride of fractionated plant fatty acids with chain lengths of $C_8$ and $C_{10}$ combined with linoleic acid (about 4-5%). A commercially available product is known as MIGLYOL® 818. In yet another embodiment, the neutral oil is a glycerin ester of fractionated plant fatty acids with chain lengths of $C_8$ and $C_{10}$ combined with succinic acid. A commercially available product is known as MIGLYOL® 829. In another embodiment, the neutral oil may be a propylene glycol diester of saturated plant fatty acids with chain lengths of $C_8$ and $C_{10}$. A commercially available product is known as MIGLYOL® 840 (propylene glycol dicaprylate/dicaprate). In yet another embodiment, the co-solvent may be a mixture of two or more neutral oils.

In another embodiment, the present invention provides extended release injectable compositions for the treatment or prevention of parasite infections or infestations in an animal comprising an antiparasitic effective amount of at least one isoxazoline compound of formula (Id), a pharmaceutically acceptable polymer and optionally a solvent or mixture of solvents. The pharmaceutically acceptable polymers in the extended release injectable compositions, include, but are not limited to, polylactides, polyglycolides, polycaprolactones, polyanhydrides, polyamides, polyurethanes, polyester amides, polyorthoesters, polydioxanones, polyacetals, polyketals, polycarbonates, polyorthocarbonates, polyphosphazenes, pseudo poly(amides), polyhydroxyalcanoates, polyhydroxybutyrates, polyhydroxyvalerates, polyalkylene oxalates, polyalkylene succinates, poly(malic acid), poly (amino acids), poly(methyl vinyl ether), poly(maleic anhydride), chitin, chitosan, and copolymers, terpolymers, or combinations or mixtures therein including copolymers of polylactides, polycaprolactones, polyglycolides (e.g., poly (lactide-co-glycolide) and copolymers of polyethylene glycol or methoxy polyethylene glycol with one or more of polycaprolactone, polylactide or any of the other polymers/polymer groups mentioned above. Also included are derivatives of pharmaceutically acceptable polymers such as hydroxylated derivatives including polycaprolactone diols and the like.

The solvents used in the extended release injectable compositions of the invention may be a single or a blend of solvents. Non-limiting examples of these solvents include alcohols such as ethanol, 1-propanol, isopropanol, glycol ethers (e.g., including, but limited to, diethyleneglycol monoethyl ether (DGME, Transcutol®), butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like), liquid polyethylene glycols (PEGs) including, but not limited to, PEG 200, PEG 300 and PEG 400; propylene glycol, glycerol, glycerol esters including glycerol triacetate (triacetin), benzyl benzoate, ethyl acetate, cyclic carbonates (e.g., ethylene carbonate and propylene carbonate), 2-pyrrolidone, N-methylpyrrolidone, dimethyl isosorbide (DMI), dimethylacetamide (DMA), dimethyl formamide (DMF), caprolactam, glycerol formal, acetone, dimethylsulfoxide (DMSO), ethyl acetate, ethyl lactate, benzyl benzoate, or a mixture of at least two of these solvents.

Topical, dermal and subdermal compositions may include, by way of non-limiting example, emulsions, creams, ointments, gels, pastes, powders, shampoos, pour-on compositions, ready-to-use compositions, spot-on solutions and suspensions, dips and sprays. Topical application of an inventive compound or of a composition including at least one inventive compound among active agent(S) therein, in the form of a spot-on, spray-on or pour-on composition, may allow for the inventive composition to be absorbed through the skin to achieve systemic levels, distributed through the sebaceous glands or on the surface of the skin achieving levels throughout the coat. When the compound is distributed through the sebaceous glands, they may act as a reservoir, whereby there may be a long-lasting effect (up to several months) effect. Spot-on compositions are typically applied in a localized region which refers to an area other than the entire animal. In one embodiment, the location may be between the shoulders. In another embodiment it may be a stripe, e.g. a stripe from head to tail of the animal.

Pour-on compositions are described in U.S. Pat. Nos. 6,010,710 and 9,180,121, both incorporated herein by reference. Pour-on compositions may be advantageously oily, and generally comprise a diluent or vehicle and also a solvent (e.g. an organic solvent) for the active ingredient if the latter is not soluble in the diluent.

Organic solvents that can be used in the invention include, but are not limited to, acetyltributyl citrate, fatty acid esters such as the dimethyl ester, diisobutyl adipate, acetone, acetonitrile, benzyl alcohol, ethyl alcohol, butyl diglycol, dimethylacetamide, dimethylformamide, dimethylsulfoxide, dimethyl isosorbide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, N-methylpyrrolidone, diethylene glycol monoethyl ether, ethylene glycol, benzyl benzoate, ethyl acetate, triacetin, $C_1$-$C_{10}$ esters of carboxylic acids such as butyl or octyl acetate, glycerol formal, dialkyl esters of dicarboxylic acids including diethyl sebacate, diisopropyl sebacate, diisopropyl adipate and the like, and diethyl phthalate, or a mixture of at least two of these solvents.

The solvent will be used in proportion with the concentration of the active agent compound and its solubility in this solvent. It will be sought to have the lowest possible volume. The vehicle makes up the difference to 100%.

A vehicle or diluent for the compositions may include dimethyl sulfoxide (DMSO), glycol derivatives such as, for example, propylene glycol, glycol ethers, polyethylene glycols or glycerol. As vehicle or diluent, mention may also be made of plant oils such as, but not limited to soybean oil, groundnut oil, castor oil, corn oil, cotton oil, olive oil, rape seed oil, sunflower oil, etc.; mineral oils such as, but not limited to, petrolatum, paraffin, silicone, etc.; aliphatic or cyclic hydrocarbons or alternatively, for example, medium-chain (such as $C_8$ to $C_{12}$) triglycerides.

In another embodiment of the invention, an emollient and/or spreading and/or film-forming agent may be added. In one embodiment, the emollient and/or spreading and/or film-forming agent may be:

(a) polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, silicone oils, polydiorganosiloxane oils (such as polydimethylsiloxane (PDMS) oils), for example those containing silanol functionalities, or a 45V2 oil, (b) anionic surfactants such as alkaline stearates, sodium, potassium or ammonium stearates; calcium stearate, triethanolamine stearate; sodium abietate; alkyl sulfates (e.g. sodium lauryl sulfate and sodium cetyl sulfate); sodium dodecylbenzenesulfonate, sodium dioctylsulphosuccinate; fatty acids (e.g. those derived from coconut oil), (c) cationic surfactants include water-soluble quaternary ammonium salts of formula N+R'R"R"'R"", Y⁻ in which the radicals R are optionally hydroxylated hydrocarbon radicals and Y⁻ is an anion of a strong acid such as the halide, sulfate and sulfonate anions; cetyltrimethylammonium bromide is among the cationic surfactants which can be used, (d) amine salts of formula N⁺HR'R"R'" in which the radicals R are optionally hydroxylated hydrocarbon radicals; octadecylamine hydrochloride is among the cationic surfactants which can be used, (e) nonionic surfactants such as sorbitan esters, which are optionally polyoxyethylenated (e.g. polysorbate 80), polyoxyethylenated alkyl ethers; polyoxypropylated fatty alcohols such as polyoxypropylene-styrol ether; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, (f) amphoteric surfactants such as the substituted lauryl compounds of betaine; or (g) a mixture of at least two of these agents.

In one embodiment of the amount of emollient, the emollient used may be in a proportion of from about 0.1 to 50% or 0.25 to 5%, by volume. In another embodiment, the emollient used may be in a proportion of from about 0.1% to about 30%, about 1% to about 30%, about 1% to about 20%, or about 5% to about 20% by volume.

In another embodiment of the invention, the composition may be in the form of a ready-to-use spot-on solution form as is described in U.S. Pat. Nos. 6,395,765 and 9,180,121, both incorporated herein by reference. In addition to the compounds of the invention, the ready-to-use solution may contain a crystallization inhibitor and an organic solvent or a mixture of organic solvents. In some embodiments, water may be included with the organic solvent.

In various embodiments of the invention, the compositions may include a crystallization inhibitor in an amount of about 1 to about 50% (w/v) or about 5 to about 40% (w/v) based on the total weight of the composition. In other embodiments, the amount of crystallization inhibitor in the inventive compositions may be about 1% to about 30%, about 5% to about 20%, about 1% to about 15%, or about 1% to about 10% (w/w). The type of crystallization inhibitor used in the inventive compositions is not limited as long as it functions to inhibit crystallization of the active or inactive agents from the composition. For example, in certain embodiments of the invention, a solvent or co-solvent of the composition may also function as a crystallization inhibitor if it sufficiently inhibits the formation of crystals from forming over time when the composition is administered.

Crystallization inhibitors which are useful for the invention include, but are not limited to:

(a) polyvinylpyrrolidone, polyvinyl alcohols, copolymers of vinyl acetate and vinylpyrrolidone, polyethylene glycols, benzyl alcohol, dimethylformamide, dimethylacetamide, dimethylsulfoxide, 2-pyrrolidone, N-methylpyrrolidone, mannitol, glycerol, sorbitol or polyoxyethylenated esters of sorbitan; lecithin or sodium carboxymethylcellulose; or acrylic derivatives, such as acrylates or methacrylates or polymers or copolymers thereof, polyethyleneglycols (PEG) or polymers containing polyethyleneglycols, such as glycofurol and the like, and others;

(b) anionic surfactants, such as alkaline stearates (e.g. sodium, potassium or ammonium stearate); calcium stearate or triethanolamine stearate; sodium abietate; alkyl sulfates, which include but are not limited to sodium lauryl sulfate and sodium cetyl sulfate; sodium dodecylbenzenesulfonate or sodium dioctyl sulphosuccinate; or fatty acids (e.g. coconut oil);

(c) cationic surfactants, such as water-soluble quaternary ammonium salts of formula $N^+R'R''R'R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used;

(d) amine salts of formula $N^+HR'R''R'''$, in which the R radicals are identical or different optionally hydroxylated hydrocarbon radicals; octadecylamine hydrochloride is one of the cationic surfactants which can be used;

(e) non-ionic surfactants, such as optionally polyoxyethylenated esters of sorbitan, e.g.

Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide;

(f) amphoteric surfactants, such as substituted lauryl compounds of betaine;

(g) a mixture of at least two of the compounds listed in (a)-(f) above; or (h) an organic solvent or mixture of solvents which inhibit the formation of crystals or amorphous solid after the composition is administered.

In one embodiment of the crystallization inhibitor, a crystallization inhibitor pair will be used. Such pairs include, for example, the combination of a film-forming agent of polymeric type and of a surface-active agent. These agents will be selected from the compounds mentioned above as crystallization inhibitor.

In some embodiments, the organic solvent(S) may have a dielectric constant of between about 10 and about 35 or between about 20 and about 30. In other embodiments, the organic solvent may have a dielectric constant of between about 10 and about 40 or between about 20 and about 30. The content of this organic solvent or mixture of solvents in the overall composition is not limited and will be present in an amount sufficient to dissolve the desired components to a desired concentration. As discussed above, the organic solvent may also function as a crystallization inhibitor in the composition.

In some embodiments, one or more of the organic solvent (S) may have a boiling point of below about 100° C., or below about 80° C. In other embodiments, the organic solvent(S) may have a boiling point of below about 300° C., below about 250° C., below about 230° C., below about 210° C. or below about 200° C.

In some embodiments where there is a mixture of solvents, i.e. a solvent and a co-solvent, the solvents may be present in the composition in a weight/weight (W/W) ratio of about 1/50 to about 1/1. Typically the solvents will be in a ratio of about 1/30 to about 1/1, about 1/20 to about 1/1, or about 1/15 to about 1/1 by weight. Preferably, the two solvents will be present in a weight/weight ratio of about 1/15 to about 1/2. In some embodiments, at least one of the solvents present may act as to improve solubility of the active agent or as a drying promoter. In particular embodiments, at least one of the solvents will be miscible with water.

The composition may also comprise an antioxidizing agent intended to inhibit oxidation in air, this agent may be present in a proportion of about 0.005 to about 1% (w/v), about 0.01 to about 0.1%, or about 0.01 to about 0.05%.

In one embodiment of the film-forming agent, the agents are of the polymeric type which include but are not limited to the various grades of polyvinylpyrrolidone, polyvinyl alcohols, and copolymers of vinyl acetate and of vinylpyrrolidone.

In one embodiment of the surface-active agents, the agents include but are not limited to those made of non-ionic surfactants; in another embodiment of the surface active agents, the agent is a polyoxyethylenated esters of sorbitan and in yet another embodiment of the surface-active agent, the agents include the various grades of polysorbate, for example Polysorbate 80.

In another embodiment of the invention, the film-forming agent and the surface-active agent may be incorporated in similar or identical amounts within the limit of the total amounts of crystallization inhibitor mentioned elsewhere.

In another embodiment, the topical compositions include the compound crotamiton which may inhibit the crystallization of active agents from solution.

The crystallization inhibitor inhibits the formation of crystals on the coat, and improves the maintenance of the cosmetic appearance of the skin or fur; that is to say without a tendency towards sticking or towards a sticky appearance, despite the high concentration of active material. Substances other than those mentioned herein may be used as crystallization inhibitors in the present invention. In one embodiment, the effectiveness of the crystallization inhibitor may be demonstrated by a test according to which 0.3 mL of a solution comprising 10% (w/v) of the active agent in an appropriate solvent as defined above, and 10% (w/v) of the compound acting as a crystallization inhibitor are placed on a glass slide at 20° C. for 24 hours, after which fewer than crystals, preferably 0 crystals, are seen with the naked eye on the glass slide.

In one embodiment of the antioxidizing agents, the agents are those conventional in the art and include but are not limited to butylated hydroxyanisole, butylated hydroxytoluene, ascorbic acid, sodium metabisulfite, propyl gallate, sodium thiosulfate or a mixture of at least two compounds with antioxidant properties.

The composition adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume of the composition applied will depend on the type of animal and the size of the animal as well as the strength of the composition and the potency of the active agents. In one embodiment, an amount of about 0.3 to about 20 ml of the composition may be applied to the animal. In other embodiment for the volume, the volume may be about 0.1 to about 10 ml, about 0.3 to about 5 ml, about 0.5 ml to about 10 ml, or about 0.3 to about 3 ml.

In another embodiment of the invention, application of a spot-on composition according to the present invention may also provide long-lasting and broad-spectrum efficacy when the solution is applied to the mammal or bird. The spot-on compositions provide for topical administration of a concentrated solution, suspension, microemulsion or emulsion for intermittent application to a spot on the animal, generally between the two shoulders (solution of spot-on type).

For spot-on compositions, the carrier may be a liquid carrier vehicle as described in U.S. Pat. Nos. 6,426,333; 6,395,765 (incorporated herein by reference), which in may comprise a solvent or mixture of solvents including, but not limited to, acetone, an aliphatic alcohol such as methanol, ethanol, propanol, butanol, isopropanol, pentanol, hexanol, heptanol, octanol, nonanol, cyclopentanol, cyclohexanol, ethylene glycol, propylene glycol and the like; an aromatic alcohol such as phenol, cresol, naphthol, benzyl alcohol and the like; acetonitrile, butyl diglycol, an organic amide such as dimethylacetamide, dimethylformamide, monomethylacetamide, 2-pyrrolidone, N-methylpyrrolidone, vinylpyrrolidone and the like; propylene or ethylene carbonate, dimethylsulfoxide (DMSO), a glycol polymer or an ether thereof, such as polyethylene glycol (PEG) of various grades, polypropylene glycols of various grades, dipropylene glycol n-butyl ether, ethylene glycol monoethyl ether, ethylene glycol monomethyl ether, dipropylene glycol monomethyl ether, diethylene glycol monoethyl ether, ethylene glycol, diethyl phthalate fatty acid esters, such as the diethyl ester or diisobutyl adipate, or a mixture of at least two of these solvents.

In another embodiment, the solvents used for the spot-on or pour-on compositions of the invention include those described in U.S. Pat. No. 9,180,121 (incorporated by reference). Solvents for the spot-on or pour-on compositions may include, but are not limited to, carboxylic acid esters, diesters of dicarboxylic acids, fatty acid esters or diesters of fatty diacids, or a combination thereof, including, but not limited to, isopropyl palmitate, isostearyl lactate, diisopropyl adipate, dibutyl adipate, diethyl sebacate, dibutyl sebacate, octyl palmitate, polyethylene glycol (PEG) stearate and cetearyl octanoate; oils including, but not limited to, mineral oil, diglycerides, triglycerides, jojoba oil, lecithin and castor oil, or a combination thereof; long chain aliphatic alcohols such as isostearyl alcohol and the like; fatty alcohols and their esters, including, for example, cetyl alcohol, cetearyl alcohol and the like, or a combination thereof; polyethylene glycols of different molecular weight ranges including, but not limited to, PEG 300, PEG 400, PEG 600 and PEG 1000, or a combination thereof; and glycol ethers including, but not limited to, diethyleneglycol monoethyl ether (Transcutol®), butyl diglycol, propylene glycol monomethyl ether, propylene glycol monoethyl ether, dipropylene glycol n-butyl ether, ethylene glycol monoethyl ether, ethylene glycol monomethyl ether and dipropylene glycol monomethyl ether, or a combination thereof; or a combination of two or more of these solvents.

Excipients that may promote the containment of the active agent in the skin for longer periods of time and may be included in the compositions of the invention include, but are not limited to, mixed esters of sucrose and carboxylic acids including sucrose acetate isobutyrate (SAIB) and the like; low temperature melting waxes, hydrogenated vegetable oils, caprylic/capric glycerides; glycerol esters, including for example, triacetin, glycerol monooleate, glycerol monolinoleate, glycerol stearate, glyceryl distearate and the like; triglycerides, including for example, caprylic, capric/myristic/stearic triglyceride; thermoreversible polymers, such as Pluronic and poloxamers, including for example, Lutrol F127 by itself or in mixture with other poloxamers; or a combination thereof.

In another embodiment of the invention the pharmaceutically acceptable carrier for the topical compositions comprise a mixture of a diester of a dicarboxylic acid alone or in combination with one or more of additional solvents listed above, and/or an "oily" lipophilic substance, including a liquid or low melting lipophilic active agent such as (S)-methoprene, pyriproxyfen and/or permethrin; and/or a mixed ester of sucrose and carboxylic acids including a mixed ester of sucrose and acetic and isobutyric acids such as sucrose acetate isobutyrate (SAIB), and/or low melting waxes and/or hard fats.

In one embodiment, the diester of a dicarboxylic acid in the topical compositions is diethyl sebacate or diisopropyl adipate. In another embodiment, the blend of solvents comprising a dicarboxylic acid ester comprises a glycol or polyglycol, or a glycol or polyglycol ether or ester including, but not limited to, ethylene glycol (EG), propylene glycol (PG), liquid polyoxyethylene glycols (PEGs) of various grades including PEG 400, EG or PG monocaprylate, EG or PG caprylate, EG or PG monolaurate, EG or PG dicaprylate/dicaprate, diethyleneglycol monoethyl ether (DGME, Transcutol®), butyl diglycol, dipropylene glycol n-butyl ether, ethyleneglycol monoethyl ether, ethyleneglycol monomethyl ether, dipropylene glycol monomethyl ether, propylene glycol monomethyl ether, propylene glycol monoethyl ether, and the like, or a combination thereof; an ether including, but not limited to, dimethyl isosorbide; an ester or di-ester including, but not limited to, triacetin, lauryl lactate; and other solvents including glycerol formal, or mixtures thereof.

In preferred embodiments, the carrier for the topical compositions comprises a dialkyl ester of a dicarboxylic acid such as diethyl sebacate, diisopropyl sebacate, diisopropyl adipate, dibutyl adipate, or a combination thereof, alone or in combination with solvents selected from:
  a) a propylene glycol (PG) ester including PG monocaprylate, PG caprylate, PG monolaurate, PG dicaprylate/dicaprate, or a combination thereof;
  b) an ether solvent including dimethyl isosorbide, diethylene glycol monoethyl ether (also known as DGME or Transcutol®), or a combination thereof;
  c) a carboxylic acid ester including, but not limited to, triacetin, lauryl lactate, isopropyl palmitate, diisopropyl sebacate, or a combination thereof; and
  d) other "oily" or lipophilic organic solvents including glycerol formal and the like.

In some embodiments, the amount the additional solvents combined with the carboxylic acid ester or diester of a dicarboxylic acid are present in an amount of at least about 1% (v/v), at least about 5% (v/v), at least about 9.0% (v/v), at least about 13% (v/v), at least about 17% (v/v) or at least about 20% (v/v). Preferably the additional solvents will be in an amount of at least about 9% (v/v).

In other embodiments, the additional solvents will be present in an amount of about 5-70% (v/v), about 10-60% (v/v), about 10-50% (v/v), about 15-60% (v/v) or about 15-50% (v/v). In preferred embodiments, the additional solvents will be present in an amount of about 20-70% (v/v), about 20-60% (v/v), about 20-50% (v/v) or about 25-50% (v/v).

In some embodiments, the liquid carrier vehicle may optionally contain a crystallization inhibitor including, but not limited to, those described in (a) to (h) above, or a compound that may act both as a solvent and a crystallization inhibitor (as defined above), or a mixture of these crystallization inhibitors.

Spot-on compositions may be prepared by dissolving the active ingredients into the pharmaceutically or veterinary acceptable vehicle. Alternatively, the spot-on composition may be prepared by encapsulation of the active ingredient to leave a residue of the therapeutic agent on the surface of the animal. These compositions will vary with regard to the weight of the therapeutic agent in the combination depending on the species of host animal to be treated, the severity and type of infection and the body weight of the host.

Dosage forms may typically contain from about 0.1 mg to about 5 g. In other embodiments, the dosage form may contain about 0.5 mg to about 5 g of an active agent. In one embodiment of the dosage form, the dosage may contain from about 1 mg to about 500 mg of an active agent, typically about 25 mg, about 50 mg, about 100 mg, about 200 mg, about 300 mg, about 400 mg, about 500 mg, about 600 mg, about 800 mg, or about 1000 mg.

In one embodiment of the invention, the active agent may be present in the composition at a concentration of about 0.05 to about 10% weight/volume. In another embodiment of the invention, the active agent may be present in the composition as a concentration from about 0.1 to about 2% weight/volume. In yet another embodiment of the invention, the active agent may be present in the composition as a concentration from about 0.25 to about 1.5% weight/volume. In still another embodiment of the invention, the active agent may be present in the composition as a concentration about 1% weight/volume.

II. Methods of Treatment:

As discussed above, the compounds of formula (Id) are effective against ectoparasites and may be used to treat and prevent parasitic infestations in or on animals. In one embodiment, the present invention provides a method of treating or preventing an ectoparasite infestation in or on an animal (e.g. a mammal or bird) comprising administering an ectoparasiticidally effective amount of a compound of formula (Id), or pharmaceutically acceptable salts thereof, or a composition comprising the compound, to the animal. In another embodiment, the methods of the invention comprise administering an effective amount of a compound of formula (Ie) or (S)-Ie, or a pharmaceutically acceptable salt thereof, to the animal.

In another embodiment when the compounds of formula (Id) are administered in combination with compounds that are active against endoparasites, the invention provides a method for treating or preventing an endoparasitic infection and an ectoparasitic infestation in and on an animal, comprising administering a composition comprising an effective amount of a compound of formula (Id) in combination with an effective amount of at least a second active agent, or pharmaceutically acceptable salts thereof, to the animal.

Mammals which can be treated include but are not limited to humans, cats, dogs, cattle, chickens, cows, bison, deer, goats, horses, llamas, camels, pigs, sheep and yaks. In one embodiment of the invention, the mammals treated are humans, cats or dogs.

In one embodiment of the invention, the compositions of the invention comprising a compound of formula (Id) in combination with an additional compound that is active against endoparasites are effective against endoparasites that are resistant to active agents of the macrocyclic lactone class. In one embodiment, the compounds and compositions of the invention are effective for controlling *Haemonchus contortus*, *Ostertagia circumcincta* and *Trichostrongylus colubriformis* in mammals or birds.

In another embodiment, the invention provides a method for treating an parasitic infestation and/or infection in an animal, comprising administering an effective amount of a compound of formula (Id) in combination with an effective amount of activators of invertebrate GABA receptors, including an avermectin or milbemycin, to the animal in need thereof. Avermectins that may be used in combination with the compounds of the invention include, but are not limited to abamectin, dimadectin, doramectin, emamectin, eprinomectin, ivermectin, latidectin, lepimectin, and selamectin. Milbemycins compounds that may be used in combination with the compounds of the invention include, but are not limited to, milbemectin, milbemycin D, milbemycin oxime, moxidectin and nemadectin. Also included are the 5-oxo and 5-oxime derivatives of said avermectins and milbemycins.

In one embodiment for the treatment against ectoparasites, the ectoparasite is from the genera *Ctenocephalides*, *Rhipicephalus*, *Dermacentor*, *Ixodes*, *Amblyomma*, *Haemaphysalis*, *Hyalomma*, *Sarcoptes*, *Psoroptes*, Otodectes, Chorioptes, *Hypoderma*, *Damalinia*, *Linognathus*, *Haematopinus*, *Solenoptes*, *Trichodectes*, and *Felicola*. The ectoparasites treated include but are not limited to fleas, ticks, mites, mosquitoes, flies, lice, blowfly and combinations thereof. Specific examples include but are not limited to cat and dog fleas (*Ctenocephalides felis*, *Ctenocephalides* spp. and the like), ticks (*Rhipicephalus* spp., *Ixodes* spp., *Dermacentor* spp., *Amblyomma* spp. and the like), and mites (*Demodex* spp., *Sarcoptes* spp., Otodectes spp. and the like), lice (*Trichodectes* spp., *Cheyletiella* spp., *Linognathus* spp., and the like), mosquitoes (*Aedes* spp., *Culex* spp., *Anopheles* spp., and the like) and flies (*Haematobia* spp., *Musca* spp., *Stomoxys* spp., *Dermatobia* spp., *Cochliomyia* spp., and the like). In yet another embodiment for the treatment against ectoparasites, the ectoparasite is a flea and/or tick.

Additional examples of ectoparasites that may be controlled with the compounds of formula (Id) include, but are not limited, to the tick *Rhipicephalus microplus* (cattle tick), *Rhipicephalus decoloratus* and *Rhipicephalus annulatus*; myiasis such as *Dermatobia hominis* (known as Berne in Brazil) and *Cochliomyia hominivorax* (greenbottle); sheep myiasis such as *Lucilia sericata*, *Lucilia cuprina* (known as blowfly strike in Australia, New Zealand and South Africa). Flies proper, namely those whose adult constitutes the parasite, such as *Haematobia irritans* (horn fly); lice such as *Linognathus vitulorum*, etc.; and mites such as *Sarcoptes scabiei* and *Psoroptes ovis*. The above list is not exhaustive and other ectoparasites are well known in the art to be harmful to animals and humans. These include, for example migrating dipterous larvae.

In one embodiment, when administered with another compound that is active against endoparasites, the compounds and compositions of the invention may be used for treating or preventing an endoparasitic infection of the following parasite: Anaplocephala (*Anoplocephala*), Ancylostoma, Necator, Ascaris, Brugia, Bunostomum, Capillaria, Chabertia, Cooperia, cyathostomum, Cylicocyclus, Cylicodontophorus, Cylicostephanus, Craterostomum, Dictyocaulus, Dipetalonema, *Dipylidium, Dirofilaria, Dracunculus, Echinococcus, Enterobius, Fasciola*, Filaroides, Habronema, *Haemonchus, Metastrongylus, Moniezia, Necator, Nematodirus*, Nippostrongylus, *Oesophagostomum, Onchocerca, Ostertagia, Oxyuris, Parascaris, Schistosoma, Strongylus, Taenia, Toxocara, Strongyloides, Toxascaris, Trichinella, Trichuris, Trichostrongylus, Triodontophorus, Uncinaria, Wuchereria*, and combinations thereof.

In another embodiment of the invention, the parasite is *Haemonchus contortus, Ostertagia circumcincta, Trichostrongylus axei, Trichostrongylus colubriformis, Cooperia curticei, Nematodirus battus, Dirofilaria immitis*, and combinations thereof.

In another embodiment of the invention, the compounds and compositions of the invention are suitable for controlling pests such as insects selected from the group consisting of Blatella *germanica, Heliothis virescens, Leptinotarsa decemlineata, Tetramorium caespitum* and combinations thereof.

The phytoparasitic nematodes include, for example, *Anguina* spp., *Aphelenchoides* spp., *Belonolaimus* spp., *Bursaphelenchus* spp., *Ditylenchus dipsaci, Globodera* spp., *Helicotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

In addition, with or without the other pesticidal agents added to the composition, the invention can also be used to treat other pests which include but are not limited to pests:

(1) from the order of Isopoda, for example *Oniscus asellus, Armadillidium vulgare* and *Porcellio scaber;*
(2) from the order of *diplopoda*, for example *Blaniulus guttulatus;*
(3) from the order of Chilopoda, for example *Geophilus carpophagus* and *Scutigera* spp.;
(4) from the order of *symphyla*, for example *Scutigerella immaculata;*
(5) from the order of *thysanura*, for example *Lepisma saccharina;*
(6) from the order of Collembola, for example Onychiurus *armatus;*
(7) from the order of *Blattaria*, for example *Blatta orientalis, Periplaneta americana, Leucophaea maderae* and *Blattella germanica;*
(8) from the order of Hymenoptera, for example *diprion* spp., *Hoplocampa* spp., *Lasius* spp., *Monomorium pharaonis* and *Vespa* spp.;
(9) from the order of Siphonaptera, for example *Xenopsylla cheopis* and *Ceratophyllus* spp.;
(10) from the order of *anoplura* (Phthiraptera), for example, *Damalinia* spp., *Haematopinus* spp., *Linognathus* spp., *Pediculus* spp., *Trichodectes* spp.;
(11) from the class of Arachnida, for example, *Acarus siro*, Aceria *sheldoni*, Aculops spp., *Aculus* spp., *Amblyomma* spp., *Argas* spp., *Boophilus* spp., *Brevipalpus* spp., *Bryobia praetiosa*, Chorioptes spp., *Dermanyssus gallinae, Eotetranychus* spp., Epitrimerus *pyri, Eutetranychus* spp., *Eriophyes* spp., Hemitarsonemus spp., *Hyalomma* spp., *Ixodes* spp., *Latrodectus mactans, Metatetranychus* spp., *Oligonychus* spp., *Ornithodoros* spp., *Panonychus* spp., Phyllocoptruta *oleivora, Polyphagotarsonemus latus, Psoroptes* spp., *Rhipicephalus* spp., Rhizoglyphus spp., *Sarcoptes* spp., *Scorpio maurus*, Steneotarsonemus spp., Tarsonemus spp., *Tetranychus* spp., Vasates *lycopersici.;*

(12) from the class of Bivalva, for example, *Dreissena* spp.;

(13) from the order of Coleoptera, for example, *Acanthoscelides obtectus, Adoretus* spp., Agelastica *alni, Agriotes* spp., *Amphimallon solstitialis, Anobium punctatum, Anoplophora* spp., *Anthonomus* spp., *anthrenus* spp., *Apogonia* spp., *Atomaria* spp., Attagenus spp., Bruchidius *obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae*, Gibbium *psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus*, Niptus *hololeucus, Oryctes rhinoceros*, Oryzaephilus *surinamensis, Otiorrhynchus sulcatus, Oxycetonia jucunda, Phaedon cochleariae, Phyllophaga* spp., *Popillia japonica, Premnotrypes* spp., *psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., Trogoderma spp., *Tychius* spp., *Xylotrechus* spp., *Zabrus* spp.;

(14) from the order of Diptera, for example, *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *tannia* spp., *Tipula paludosa, Wohlfahrtia* spp.;

(15) from the class of Gastropoda, for example, Arion spp., *Biomphalaria* spp., *Bulinus* spp., *Deroceras* spp., *Galba* spp., *Lymnaea* spp., *Oncomelania* spp., *Succinea* spp.;

(16) from the class of helminths, for example, *Ancylostoma duodenale, Ancylostoma ceylanicum, Ancylostoma braziliensis, Ancylostoma* spp., *Ascaris lumbricoides, Ascaris* spp., *Brugia malayi, Brugia timori, Bunostomum* spp., *Chabertia* spp., *Clonorchis* spp., *Cooperia* spp., *Dicrocoelium* spp, Dictyocaulus *filaria, Diphyllobothrium latum, Dracunculus medinensis, Echinococcus granulosus, Echinococcus multilocularis, Enterobius vermicularis*, Faciola spp., *Haemonchus* spp., *Heterakis* spp., *Hymenolepis nana*, Hyostrongulus spp., *Loa Loa, Nematodirus* spp., *Oesophagostomum* spp., *Opisthorchis* spp., *Onchocerca volvulus, Ostertagia* spp., *Paragonimus* spp., Schistosomen spp., *Strongyloides fuelleborni, Strongyloides stercoralis, Strongyloides* spp., *Taenia saginata, Taenia solium, Trichinella spiralis, Trichinella nativa, Trichinella britovi, Trichinella nelsoni, Trichinella* pseudopsiralis, Trichostrongulus spp., *Trichuris trichiura, Wuchereria bancrofti.;*

(17) from the order of *heteroptera*, for example, *Anasa tristis, Antestiopsis* spp., *Blissus* spp., *Calocoris* spp.,

*Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., Heliopeltis spp., *Horcias nobilellus, Leptocorisa* spp., *Leptoglossus phyllopus, Lygus* spp., *Macropes excavatus,* Miridae, *Nezara* spp., *Oebalus* spp., Pentomidae, *Piesma quadrata, Piezodorus* spp., *Psallus seriatus, Pseudacysta persea, Rhodnius* spp., *Sahlbergella singularis,* Scotinophora spp., *Stephanitis nashi,* Tibraca spp., *Triatoma* spp.;
(18) from the order of *homoptera,* for example, Acyrthosipon spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera,* Cercopidae, *Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina,* Tenalaphara *malayensis, Tinocallis caryaefoliae, Tomaspis* spp., *Toxoptera* spp., *Trialeurodes vaporariorum, Trioza* spp., *Typhlocyba* spp., Unaspis spp., *Viteus vitifolii.;*
(19) from the order of Isoptera, for example, *Reticulitermes* spp., *Odontotermes* spp.;
(20) from the order of Lepidoptera, for example, *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Cheimatobia brumata, Chilo* spp., *Choristoneura fumiferana, Clysia ambiguella,* Cnaphalocerus spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta* padella, *Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella,* Prodenia spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.;
(21) from the order of Orthoptera, for example, *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.;*
(22) from the order of Thysanoptera, for example, *Baliothrips biformis, Enneothrips flavens, Frankliniella* spp., *Heliothrips* spp., *Hercinothrips femoralis,* Kakothrips spp., *Rhipiphorothrips cruentatus, Scirtothrips* spp., *Taeniothrips cardamoni, Thrips* spp.;
(23) from the class of Protozoa, for example, *Eimeria* spp.

In each aspect of the invention, the compounds and compositions of the invention can be applied against a single pest or combinations thereof.

Non-Veterinary Applications

For use in a method for combating pests that damage plants, plant propagation material and crops, or material derived from wood, according to the present invention, the compounds of formula (Id) can be converted into the customary compositions, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula (Id) according to the present invention.

I. Agricultural Compositions

The compositions are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8, all of which are hereby incorporated by reference in their entirety), for example by extending the active compound with auxiliaries suitable for the composition of agrochemicals, such as solvents and/or carriers, if desired emulsifiers, surfactants and dispersants, preservatives, antifoaming agents, anti-freezing agents, for seed treatment composition also optionally colorants and/or binders and/or gelling agents.

The following solvents/carriers are suitable for compositions of the invention:
  solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-methylpyrrolidone (NMP),N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.

carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers include non-ionic and anionic emulsifiers (for example polyoxyethylene fatty alcohol ethers, alkylsulfonates and arylsulfonates).

Examples of suitable dispersants include lignin-sulfite waste liquors and methylcellulose.

Suitable surfactants include alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ ethylene oxide condensates, ethoxylated castor oil, polyoxyethylene alkyl ethers, ethoxylated polyoxypropylene, lauryl alcohol polyglycol ether acetal, sorbitol esters, In some embodiments, anti-freezing agents such as glycerin, ethylene glycol, propylene glycol and bactericides such as can be added to the composition.

In other embodiments, antifoaming agents may be included in the compositions. Suitable antifoaming agents include antifoaming agents based on silicon or magnesium stearate.

The compositions of the invention may comprise preservatives. Suitable preservatives include, for example, dichlorophenyl and benzyl alcohol hemiformal In other embodiments, the compositions of the invention may include thickeners known in the art. Suitable thickeners include compounds which confer a pseudoplastic flow behavior to the composition, i.e. high viscosity at rest and low viscosity in the agitated stage. These thickeners include, for example, of commercial thickeners based on polysaccharides, such as Xanthan Gum® (Kelzan® from Kelco), Rhodopol®23 (Rhone Poulenc) or Veegum® (from R. T. Vanderbilt), or organic phyllosilicates, such as Attaclay® (from Engelhardt). Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms. Suitable biocides are, for example, based on isothiazolones such as the compounds marketed under the trademarks Proxel® from Avecia (or Arch) or Acticide® RS from Thor Chemie and Kathon® MK from Rohm & Haas. Suitable antifreeze agents are organic polyols, for example ethylene glycol, propylene glycol or glycerol. These are usually employed in amounts of not more than 10% by weight, based on the total weight of the active compound composition. If appropriate, the active compound compositions according to the invention may comprise 1 to 5% by weight of buffer, based on the total amount of the composition prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the compositions typically comprise from about 0.01 to about 95% by weight, preferably from about 0.1 to about 90% by weight, of the active ingredient. The active ingredients are employed typically have a purity of from about 90% to about 100%, preferably about 95% to about 100% (according to NMR spectrum).

For seed treatment purposes, respective compositions can be diluted 2-10 fold leading to concentrations in the ready to use preparations of about 0.01 to about 60% by weight active compound by weight, preferably about 0.1 to about 40% by weight.

The compound of formula (Id) can be used as such, in the form of their compositions or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

The following are examples of compositions:
1. Products for dilution with water. For seed treatment purposes, such products may be applied to the seed diluted or undiluted.
A) Water-Soluble Concentrates (SL, LS)
10 parts by weight of the active compound is dissolved in 90 parts by weight of water or a water-soluble solvent. As an alternative, wetters or other auxiliaries are added. The active compound dissolves upon dilution with water, whereby a composition with 10% (w/w) of active compound is obtained.

B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a composition with 20% (w/w) of active compounds is obtained.

C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a composition with 15% (w/w) of active compounds is obtained.

D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a composition with 25% (w/w) of active compound is obtained.

E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a composition with 20% (w/w) of active compound is obtained.

F) Water-Dispersible Granules and Water-Soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a composition with 50% (w/w) of active compound is obtained.

G) Water-Dispersible Powders and Water-Soluble Powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a composition with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a composition with 20% (w/w) of active compound is obtained.

2. Products to be applied undiluted for foliar applications. For seed treatment purposes, such products may be applied to the seed diluted or undiluted.

I) Dustable Powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a composition with 0.5% (w/w) of active compound is obtained. Current methods are extrusion, spray-drying or the fluidized bed. This gives granules to be applied undiluted for foliar use.

K) ULV Solutions (UL)

10 parts by weight of the active compound is dissolved in 90 parts by weight of an organic solvent, for example xylene. This gives a product having 10% (w/w) of active compound, which is applied undiluted for foliar use.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from about 0.0001 to about 10%, preferably from about 0.01 to about 1%.

The active ingredients may also be used successfully in the ultra-low-volume process (ULV), it being possible to apply compositions comprising over 95% by weight of active ingredient, or even to apply the active ingredient without additives.

II. Mixtures with Other Actives

In the method of this invention compounds of formula (Id), including in particular (Ie) and (S)-Ie, may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(S) may be sprayed with a composition of this invention either before or after being treated with other active ingredients.

The following list M of pesticides together with which the compounds according to the invention can be used and with which potential synergistic effects might be produced, is intended to illustrate the possible combinations, but not to impose any limitation:

M.1. Organo(thio)phosphate compounds: acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cis-trans allethrin, d-trans allethrin, bifenthrin, bioallethrin, bioallethrin S-cylclopentenyl, bioresmethrin, cyclopro-thrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empen-thrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5. Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. Ryanodine receptor modulators: flubendiamide and the phtalamid compound (R)-, (S)-3-Chlor-N1-{2-methyl-4-[1,2,2,2-tetrafluor-1-(trifluormethyl)ethyl]phenyl}-N2-(1-methyl-2-methylsulfonylethyl)phthalamid (M21.1)

M.22. Isoxazoline compounds: 4-[5-(3,5-Dichloro-phenyl)-5-trifluoromethyl-4,5-dihydro-isoxazol-3-yl]-2-methyl-N-pyridin-2-ylmethyl-benzamide (M22.1), 4-[5-(3,5-Dichloro-phenyl)-5-trifluoromethyl-4,5-dihydro-isoxazol-3-yl]-2-methyl-N-(2,2,2-trifluoroethyl)-benzamide (M22.2), 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide (M22.3), 4-[5-(3,5-Dichloro-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.4)4-[5-(3,5-Dichlorophenyl)-5-trifluoromethyl-4,5-dihydro-isoxazol-3-yl]-N-[(methoxyimino)methyl]-2-methylbenzamide (M22.5), 4-[5-(3-Chloro-5-trifluoromethyl-phenyl)-5-trifluoromethyl-4,5-dihydro-isoxazol-3-yl]-2-methyl-N-[(2,2,2-trifluoro-ethylcarbamoyl)-methyl]-benzamide (M22.6), 4-[5-(3-Chloro-5-trifluoromethyl-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.7) and 5-[5-(3,5-Dichloro-4-fluoro-phenyl)-5-trifluoromethyl-4,5-dihydro-isoxazol-3-yl]-2-[1,2,4]triazol-1-yl-benzonitrile (M22.8);

M.23. Anthranilamide compounds: chloranthraniliprole, cyantraniliprole,

5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M23.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M23.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds: 2-(2,2,3,3,4,4,5,5-octafluoropentyl)-2-(3,3,3-trifluoro-propyl)malononitrile (CF$_2$H—CF$_2$—CF$_2$—CF$_2$—CH$_2$—C(CN)$_2$—CH$_2$—CH$_2$—CF$_3$) (M24.1) and 2-(2,2,3,3,4,4,5,5-octafluoropentyl)-2-(3,3,4,4,4-pentafluorobutyl)-malonodinitrile (CF$_2$H—CF$_2$—CF$_2$—CF$_2$—CH$_2$—C(CN)$_2$—CH$_2$—CH$_2$—CF$_2$—CF$_3$) (M24.2);

M.25. Microbial disruptors: *Bacillus thuringiensis* subsp. Israelensi, *Bacillus sphaericus*, *Bacillus thuringiensis* subsp. *aizawai*, *Bacillus thuringiensis* subsp. Kurstaki, *Bacillus thuringiensis* subsp. *tenebrionis*;

M.26. Aminofuranone compounds:
4-{1[(6-Bromopyrid-3-yl)methyl](2-fluoroethyl)amino}furan-2(5H)-on (M26.1),
4-{[(6-Fluoropyrid-3-yl)methyl](2,2-difluoroethyl)amino}furan-2(5H)-on (M26.2),
4-{[(2-Chloro1,3-thiazolo-5-yl)methyl](2-fluoroethyl)amino}furan-2(5H)-on (M26.3),
4-{1[(6-Chloropyrid-3-yl)methyl](2-fluoroethyl)amino}furan-2(5H)-on (M26.4),
4-{[(6-Chloropyrid-3-yl)methyl](2,2-difluoroethyl)amino}furan-2(5H)-on (M26.5),
4-{[(6-Chloro-5-fluoropyrid-3-yl)methyl](methyl)amino}furan-2(5H)-on (M26.6),
4-{[(5,6-Dichloropyrid-3-yl)methyl](2-fluoroethyl)amino}furan-2(5H)-on (M26.7),
4-{[(6-Chloro-5-fluoropyrid-3-yl)methyl](cyclopropyl)amino}furan-2(5H)-on (M26.8),
4-{[(6-Chloropyrid-3-yl)methyl](cyclopropyl)amino}furan-2(5H)-on (M26.9) and
4-{[(6-Chloropyrid-3-yl)methyl](methyl)amino}furan-2(5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N—R'-2,2-dihalo-1-R"cyclo-propanecarboxamide-2-(2,6-dichloro-α,α,α-trifluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester (M27.2) and 8-(2-Cyclopropylmethoxy-4-trifluoromethyl-phenoxy)-3-(6-trifluoromethyl-pyridazin-3-yl)-3-aza-bicyclo[3.2.1]octane (M27.3).

The commercially available compounds of the group M may be found in The Pesticide Manual, 13th Edition, British Crop Protection Council (2003) among other publications.

Paraoxon and their preparation have been described in Farm Chemicals Handbook, Volume 88, Meister Publishing Company, 2001. Flupyrazofos has been described in Pesticide Science 54, 1988, p.237-243 and in U.S. Pat. No. 4,822,779. AKD 1022 and its preparation have been described in U.S. Pat. No. 6,300,348. The anthranilamides M23.1 to M23.6 have been described in WO 2008/72743 and WO 200872783, those M23.7 to M23.12 in WO2007/043677. The phthalamide M 21.1 is known from WO 2007/101540. The alkynylether compound M27.1 is described e.g. in JP 2006131529. Organic sulfur compounds have been described in WO 2007060839. The isoxazoline compounds M 22.1 to M 22.8 have been described in e.g. WO2005/085216, WO 2007/079162, WO 2007/026965, WO 2009/126668 and WO2009/051956. The aminofuranone compounds M 26.1 to M 26.10 have been described eg. in WO 2007/115644. The pyripyropene derivative M 27.2 has been described in WO 2008/66153 and WO 2008/108491. The pyridazin compound M 27.3 has been described in JP 2008/115155. Malononitrile compounds as those (M24.1) and (M24.2) have been described in WO 02/089579, WO 02/090320, WO 02/090321, WO 04/006677, WO 05/068423, WO 05/068432 and WO 05/063694. All of the documents referred to above are hereby incorporated by reference in their entirety.

Fungicides that may be mixed with the compounds of the invention include, but are not limited to, acylalanines such as benalaxyl, metalaxyl, ofurace, oxadixyl; amine derivatives such as aldimorph, dodine, dodemorph, fenpropimorph, fenpropidin, guazatine, iminoctadine, spiroxamin, tridemorph; anilinopyrimidines such as pyrimethanil, mepanipyrim or cyrodinyl; antibiotics such as cycloheximid, griseofulvin, kasugamycin, natamycin, polyoxin or streptomycin; azoles such as bitertanol, bromoconazole, cyproconazole, difenoconazole, dinicona-zole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol; dicarboximides such as iprodion, myclozolin, procymidon, vinclozolin; dithiocarbamates such as ferbam, nabam, maneb, mancozeb, metam, metiram, propineb, polycarbamate, thiram, ziram, zineb; heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine; copper fungicides such as Bordeaux mixture, copper acetate, copper oxychloride, basic copper sulfate; nitrophenyl derivatives such as binapacryl, dinocap, dinobuton, nitrophthalisopropyl; phenylpyrroles such as fenpiclonil or fludioxonil, Sulfur; other fungicides such as acibenzolar-S-methyl, benthiavalicarb, carpropamid, chlorothalonil, cyflufenamid, cymoxanil, diclomezin, diclocymet, diethofencarb, edifen-phos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid; strobilurins such as azoxystrobin, dimoxystrobin, fluoxastrobin, kresoximmethyl, me-tominostrobin, orysastrobin, picoxystrobin or trifloxystrobin; sulfenic acid derivatives such as captafol, captan, dichlofluanid, folpet, tolylfluanid; cinnemamides and analogs such as dimethomorph, flumetover or flumorph.

III. Uses and Methods

Due to their excellent activity, the compounds of formula (Id), and in particular compounds of formula (Ie) and (S)-Ie, may be used for controlling pests. Accordingly, the present invention also provides a method for controlling animal pests, which method comprises treating the pests, their food supply, their habitat or their breeding ground or a cultivated plant, plant propagation materials (such as seed), soil, area, material or environment in which the pests are growing or may grow, or the materials, cultivated plants, plant propagation materials (such as seed), soils, surfaces or spaces to be protected from pest attack or infestation with a pesticidally effective amount of a compound of formula (Id), or a salt thereof, or a composition as defined above.

In one embodiment, the method of the invention serves for protecting plant propagation material (such as seed) and the plant which grows therefrom from animal pest attack or infestation and comprises treating the plant propagation material (such as seed) with a pesticidally effective amount of a compound of formula (Id) or an agriculturally acceptable salt thereof as defined above or with a pesticidally effective amount of an agricultural composition as defined above and below. The method of the invention is not limited to the protection of the "substrate" (plant, plant propagation materials, soil material etc.) which has been treated according to the invention, but also has a preventive effect, thus, for example, according protection to a plant which grows from a treated plant propagation materials (such as seed), the plant itself not having been treated.

In one embodiment of the present invention related to agricultural applications, "animal pests" are preferably selected from arthropods and nematodes, more preferably from harmful insects, arachnids and nematodes, and even more preferably from insects, acarids and nematodes.

The invention further provides an agricultural composition for combating such animal pests, which comprises such an amount of at least one compound of formula (Id) or at least one agriculturally useful salt thereof, and at least one inert liquid and/or solid agriculturally acceptable carrier that has a pesticidal action and, if desired, at least one surfactant. Such a composition may contain a single active compound of formula (Id), or a salt thereof, or a mixture of several active compounds of formula (Id), or their salts, according to the present invention. The composition according to the present invention may comprise an individual isomer or mixtures of isomers as well as individual tautomers or mixtures of tautomers.

The animal pest, i.e. the insects, arachnids and nematodes, the plant, soil or water in which the plant is growing can be contacted with the present compounds of formula (Id) or composition(S) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula (Id) or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with an insecticidally effective amount of the active compounds. The application can be carried out both before and after the infection of the plants, plant propagation materials, such as seeds, soil, surfaces, materials or rooms by the insects.

The present invention also includes a method of combating animal pests which comprises contacting the animal pests, their habitat, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture of at least one active compound of formula (Id). Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

In one embodiment, the compounds of the invention can also be applied preventively to places at which occurrence of the pests is expected.

The compounds of formula (Id) may be also used to protect growing plants from attack or infestation by pests by contacting the plant with a pesticidally effective amount of compounds of formula (Id). As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow, excluding the body of an animal.

The term "plant propagation material" refers to any parts of a plant which are propagable. In general, a plant propagation material includes the product of the ripened ovule of gymnosperm and angiosperm plants which occurs after fertilization and some growth within the mother plant and includes seed, fruits, spurious fruits, infructescences and also rhizomes (rootstocks), corms, tubers, bulbs and scions.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transitional modification of protein(S) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8, Protein Eng Des Sel. 2004 January; 17(1):57-66, Nat Protoc. 2007; 2(5):1225-35, Curr Opin Chem Biol. 2006 October; 10(5):487-91. Epub 2006 Aug. 28, Biomaterials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus Bacillus, particularly from Bacillus thuringiensis, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example Photorhabdus spp. or Xenorhabdus spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are disclosed, for example, in EP-A 374 753, WO 93/007278, WO 95/34656, EP-A 427 529, EP-A 451 878, WO 03/018810 und WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against Phytophthora infestans derived from the Mexican wild potato Solanum bulbocastanum) or T4-lysozym (e.g. potato cultivars capable of synthesizing these proteins with increased resistance against bacteria such as Erwinia amylvora). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from about 0.0001 to about 500 g per 100 m$^2$, preferably from about 0.001 to about 20 g per 100 m$^2$.

Customary application rates in the protection of materials are, for example, from about 0.01 g to about 1000 g of active compound per m² treated material, desirably from about 0.1 g to about 50 g per m².

Insecticidal compositions for use in the impregnation of materials typically contain from about 0.001 to about 95 weight %, preferably from about 0.1 to about 45 weight %, and more preferably from about 1 to about 25 weight % of at least one repellent and/or insecticide.

For use in treating crop plants, the rate of application of the active ingredients of this invention may be in the range of about 0.1 g to about 4000 g per hectare, desirably from about 25 g to about 600 g per hectare, more desirably from about 50 g to about 500 g per hectare.

The compounds of formula (Id) are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitos, crickets, or cockroaches. For use against said non-crop pests, compounds of formula (Id) are preferably used in a bait composition. The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickiness, moisture retention or aging characteristics.

The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from about 0.001 weight % to about 15 weight %, desirably from about 0.001 weight % to about 5% weight % of active compound.

Formulations of compounds of formula (Id) as aerosols (e.g. in spray cans), oil sprays or pump sprays are highly suitable for the non-professional user for controlling pests such as flies, fleas, ticks, mosquitos or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide (e.g. Labrafil® M 1944 CS), fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray compositions differ from the aerosol recipes in that no propellants are used. For use in spray compositions, the content of active ingredient is from about 0.001 to about 80 weights %, preferably from about 0.01 to about 50 weight % and most preferably from about 0.01 to about 15 weight %.

The compounds of formula (Id), or salts thereof, and their respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filiariasis, and leishmaniasis) with compounds of formula (Id), or salts thereof, and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, non-wovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl) acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant extracts like limonene, eugenol, (+)-Eucamalol (1), (−)-1-epi-eucamalol or crude plant extracts from plants like Eucalyptus maculata, Vitex rotundifolia, Cymbopogan martinii, Cymbopogan citratus (lemon grass), Cymopogan nartdus (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexyacrylate, and methyl acrylate, mono- and di-ethylenically unsaturated hydrocarbons, such as styrene, and aliphatic dienes, such as butadiene. The impregnation of curtains and bednets is done in general by dipping the textile material into emulsions or dispersions of the insecticide or spraying them onto the nets.

The compounds of formula (Id) and their compositions can also be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula (Id) are applied not only to the surrounding soil surface or into the under-floor soil in order to protect wooden materials but can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

IV. Seed Treatment

In some embodiments of the invention, the compounds of formula (Id) are also suitable for the treatment of seeds in order to protect the seed from insect pest, in particular from soil-living insect pests and the resulting plant's roots and shoots against soil pests and foliar insects.

The compounds of formula (Id) are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the general formula (Id), or a salt thereof. Particularly preferred is a method, wherein the plant's roots and shoots are protected, more preferably a method, wherein the plants shoots are protected from piercing and sucking insects, most preferably a method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting. The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed includes, but is not limited to, seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and *impatiens*.

In addition, the active compounds may also be used for the treatment seeds from plants, which tolerate the action of herbicides or fungicides or insecticides owing to breeding, including genetic engineering methods. For example, the active compounds can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259).

Furthermore, the active compounds of the invention can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is typically carried out by spraying or by dusting the seeds before sowing of the plants and before emergence of the plants.

Compositions which are especially useful for seed treatment include:

A Soluble concentrates (SL, LS)

D Emulsions (EW, EO, ES)

E Suspensions (SC, OD, FS)

F Water-dispersible granules and water-soluble granules (WG, SG)

G Water-dispersible powders and water-soluble powders (WP, SP, WS)

H Gel-Formulations (GF)

I Dustable powders (DP, DS)

Conventional seed treatment compositions include, for example, flowable concentrates FS, solutions LS, powders for dry treatment DS, water dispersible powders for slurry treatment WS, water-soluble powders SS and emulsion ES and EC and gel composition GF. These compositions can be applied to the seed diluted or undiluted. Application to the seeds is carried out before sowing, either directly on the seeds or after having pregerminated the latter.

In a preferred embodiment a FS composition is used for seed treatment. Typically, a FS composition may comprise about 1-800 g/l of active ingredient, about 1-200 g/l Surfactant, about 0 to 200 g/l antifreezing agent, about 0 to 400 g/l of binder, about 0 to 200 g/l of a pigment and up to about 1 liter of a solvent, preferably water.

Especially preferred FS compositions of compounds of formula I for seed treatment usually comprise from about 0.1 to about 80% by weight (1 to 800 g/l) of the active ingredient, from about 0.1 to about 20% by weight (1 to 200 g/l) of at least one surfactant, e.g. about 0.05 to about 5% by weight of a wetter and from about 0.5 to about 15% by weight of a dispersing agent, up to about 20% by weight, e.g. from about 5 to about 20% of an anti-freeze agent, from about 0 to about 15% by weight, e.g. about 1 to about 15% by weight of a pigment and/or a dye, from about 0 to about 40% by weight, e.g. about 1 to about 40% by weight of a binder (sticker/adhesion agent), optionally up to about 5% by weight, e.g. from about 0.1 to about 5% by weight of a thickener, optionally from about 0.1 to about 2% of an anti-foam agent, and optionally a preservative such as a biocide, antioxidant or the like, e.g. in an amount from about 0.01 to about 1% by weight and a filler/vehicle up to 100% by weight.

Seed Treatment compositions may additionally also comprise binders and optionally colorants. Binders can be added to improve the adhesion of the active materials on the seeds after treatment. Suitable binders include, but are not limited to, homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethylene amides and polyethyleneimines, polysaccharides like celluloses, tylose and starch, polyolefin homo- and copolymers like olefin/maleic anhydride copolymers, polyurethanes, polyesters, polystyrene homo and copolymers Optionally, colorants or dyes may also be included in the composition. Suitable colorants or dyes for seed treatment compositions include, but are not limited to, Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

A gelling agent may also be used in some compositions of the invention. One non-limiting example of a gelling agent is carrageen (Satiagel®)

In the treatment of seed, the application rates of the compounds of formula (Id) are generally from about 0.1 g to about 10 kg per 100 kg of seed, preferably from about 1 g to about kg per 100 kg of seed, more preferably from about 1 g to about 1000 g per 100 kg of seed and in particular from about 1 g to about 200 g per 100 kg of seed.

The invention therefore also relates to seed comprising a compound of formula (Id), or an agriculturally useful salt thereof, as defined herein. The amount of the compound of formula (Id), or the agriculturally useful salt thereof, will in general vary from about 0.1 g to about 10 kg per 100 kg of seed, preferably from about 1 g to about 5 kg per 100 kg of seed, in particular from about 1 g to about 1000 g per 100 kg of seed. The application rate will vary depending on the specific crop, as known to those in skill in the art. For specific crops such as lettuce the rate may be higher than specified above.

The invention will now be further described by way of the following non-limiting examples.

EXAMPLES

The invention is further described by the following non-limiting examples which further illustrate the invention, and are not intended, nor should they be interpreted to, limit the scope of the invention.

Synthesis Examples

Synthesis Example 1: Synthesis of (S)-Ie

The compound of formula (S)-Ie of the invention was prepared according to Scheme 2 below. Compound 2-1 is described in U.S. Pat. No. 7,951,828 B1, incorporated herein by reference. Preparation of the compound 2-4 is described in U.S. Pat. No. 8,217,180 B2 and U.S. Pat. No. 8,546,618 B2, both incorporated herein by reference in their entirety. Cinchona alkaloid-based chiral phase transfer catalyst similar to 2-6 are prepared according to the procedures described in, for example, U.S. Pat. No. 9,126,995 B2, WO 2011/104089 and US 2014/0206633, all incorporated herein by reference. Further, Matoba et al., Angew. Chem. 2010, 122, 5898-5902 describes the use of these catalysts to prepare enantiomerically pure isoxazoline compounds.

Scheme 2

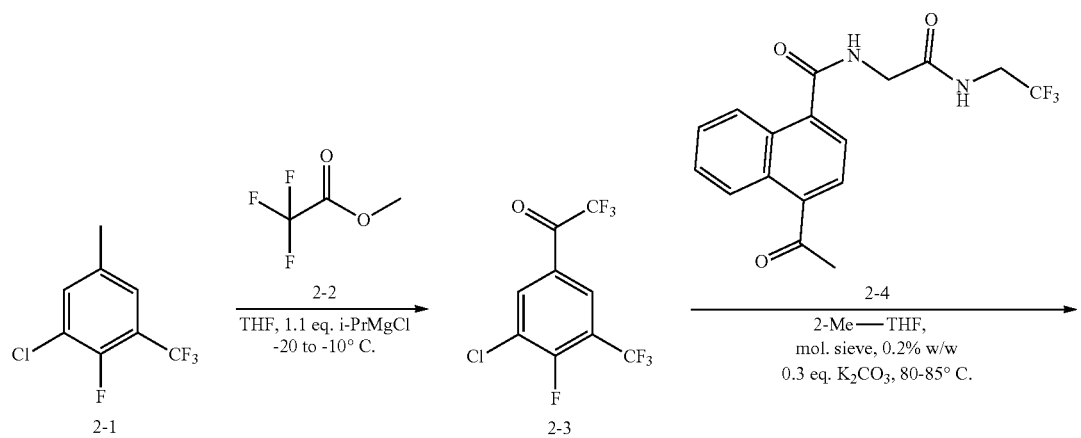

-continued

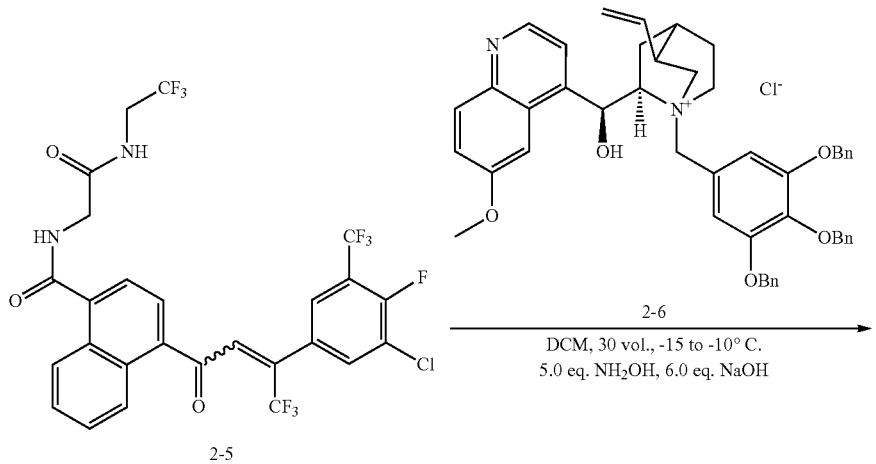

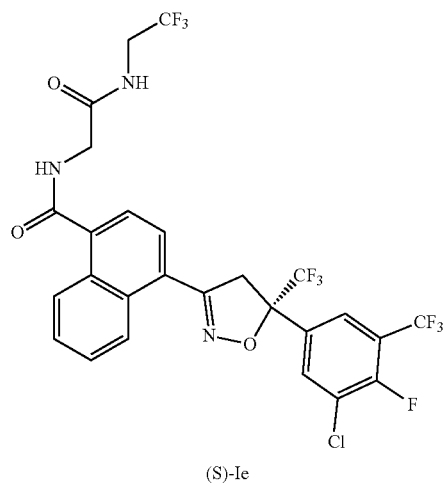

(S)-Ie

Step 1

1-Chloro-2-fluoro-5-iodo-3-(trifluoromethyl)benzene (2-1, 100 g, 0.31 mol) and tetrahydrofuran (THF, 200 ml, 2 volumes) were charged into a 500 ml reactor under an atmosphere of nitrogen. The mixture was cooled to −15 to −20° C. and a solution of i-PrMgCl in THF (2M, 170 ml, 0.34 mol, 1.1 eq.) was added to the reactor slowly (over 30 min.) at −20 to −5° C. The resulting mixture was stirred for an additional 0.5-1 hour and checked for reaction completion by GCMS, which showed that the starting material was consumed. Methyl 2,2,2-trifluoroacetate was added to the reaction mixture over 0.5-1 hour at −20 to −5° C. The resulting mixture was stirred overnight at −20 to −10° C. and checked for reaction conversion. When the reaction was complete, aqueous HCl (1 M, 500 ml) was added and the mixture was stirred for 1-2 hours at −5 to 5° C. The quenched reaction mixture was extracted with cyclohexane twice (500 ml, 200 ml) and the combined organic layers were concentrated under vacuum to provide intermediate 2-3 as a crude product (62.0 g, purity 98.4%, 77.7%).

Step 2

2-methyltetrahydrofuran (2-Me-THF, 25 ml, 5 vol.), intermediate 2-4 (5.0 g, 17 mmol, 1 eq.), molecular sieves (1.0 g, 20% w/w) and potassium carbonate (0.7 g, 5.1 mmol, 0.3 eq.) were charged into a 100 ml, 3-neck flask. The resulting mixture was warmed to 75-85° C. and compound 2-3 was added drop-wise to the mixture at 75-85° C. over 0.5-1 hour. The mixture was then stirred for an additional 4 hours at the same temperature and tested by HPLC for reaction progression. Additional $K_2CO_3$ (0.2 g, 1.7 mmol) and 2-3 (0.1 g, 0.34 mmol, 0.2 eq.) were added and the mixture was stirred for a further 16 hours. The mixture was cooled to 30-40° C. and filtered. The filtrate was concentrated to a brown solid. The product was purified by chromatography (silica gel, petroleum ether/ethyl acetate) to yield the product as a yellow solid (6.6 grams, 79.7% purity). The product was then recrystallized from acetonitrile to yield compound 2-5 in 44.9% yield (4.0 grams) and 91.6% purity.

Step 3

Dichloromethane (DCM, 150 ml, 30 vol.) and 2-5 (5.0 g, 7.95 mmol, 1.0 eq.) were charged into a 500 ml 3-neck flask. The mixture was stirred for 10-30 min. until the compound was dissolved and then cooled to −10 to 15° C. The chiral phase transfer catalyst 2-6 was added (0.18 g, 0.024 mmol, 0.03 eq.) to the solution and then a solution of $NH_2OH$ (50% w/w)/$NaOH/H_2O$ (20 ml, 5 vol.) was added dropwise at −10 to 15° C. over 0.5-1 hour. The resulting mixture was stirred for 16 hours at −10 to 15° C. and sampled for analysis by HPLC to check the reaction completion, at which time there was less than 3.0% of the starting material. The organic layer was separated and washed with a saturated solution of $KH_2PO_4$ (20 ml, 4 vol.) twice. The resulting organic layer was further washed with brine (20 ml) twice and then concentrated under vacuum at 30-40° C. with the concomitant addition of toluene (20 ml, 4 vol.) and then concentrated to dryness.

To 4.9 grams of the isolated crude product was charged 15 ml of toluene in a 3-neck flask and the mixture was heated to 60-70° C. to dissolve the solid. The resulting solution was cooled slowly to 45-50° over 1 hour and seed (0.025 g, 0.05% w/w) was added. The seeded mixture was stirred for 1 hour at 45-50° C. and then cooled further to 37-42° C. over 1 hour and then stirred for a further 6 hours. During this time the product was observed to crystallize from solution. The mixture was cooled to 30-35° C. over 1 hour and stirred for 3 hours. The solid was filtered and the cake washed with toluene (10 ml, 2 vol.). The cake was then dried in an oven at 40-45° under vacuum for 6 hours to yield 2.3 grams (45.1% yield) of (S)-Ie in 99.4% purity and 99.3% chiral purity.

Using the same approach but an alternative chiral phase transfer catalyst (e.g. isomer of 2-6), the compound (R)-Ie may be made. Alternatively, a racemic compound of formula (Ie) may be prepared without the use of a chiral phase transfer catalyst. The final step in these processes are described in the examples below.

Synthesis Example 2: Racemic Compound (Ie)

Step 3

Into a 5 liter reactor was charged 2 liters (10 volumes) of DCM and 200.0 grams (0.32 mol, 1.0 eq.) and the mixture was stirred for 10-30 minutes to dissolve the solid. The solution was cooled to 0-5° C. and $NH_2OH$ (50% w/w)/$NaOH/H_2O$ (104.9 g/76.3 g/1.0 L) was added dropwise at 0-25° C. over 30-60 min. The resulting mixture was stirred at 10-25° C. for 3 hours and then sampled to check the reaction conversion by HPLC, which showed that the starting material was present at less than 3.5%. The mixture was allowed to settle and the DCM layer was washed with a saturated solution of $KH_2PO_4$ (0.8 L, 4 vol.) twice. The resulting organic layer was further washed with brine (0.8 L, 4 vol.) twice. The combined organic layers were concentrated under vacuum at 30-40° C. to dryness and to provide the crude product as a yellow solid (196.0 g, purity: 94%, chiral purity: 49.7%). The crude product was purified by chromatography over silica gel using DCM:ethanol (100:1 to 20:1) to get 138.0 grams of the pure product (purity: 99.5%, chiral purity: 49.7%). The product was further dried to remove toluene to yield 125.0 grams as a light yellow solid (yield, 61.2%, purity: 99.5%, chiral purity: 49.7%).

Synthesis Example 3: Preparation of Compound (S)-if

The compound of formula (S)—If was prepared using a process very similar to that shown above for (S)-Ie with the key difference that 1-iodo-3,5-dichlorobenzene was used as starting material instead of 1-Chloro-2-fluoro-5-iodo-3-(trifluoromethyl)benzene. The process for the preparation of (S)-If is shown in Scheme 3 below and the detailed procedure for Step 3 is provided.

Scheme 3

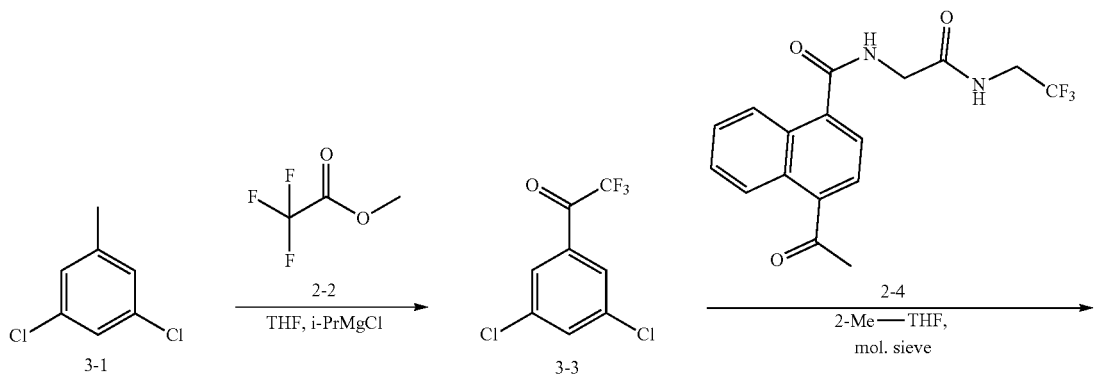

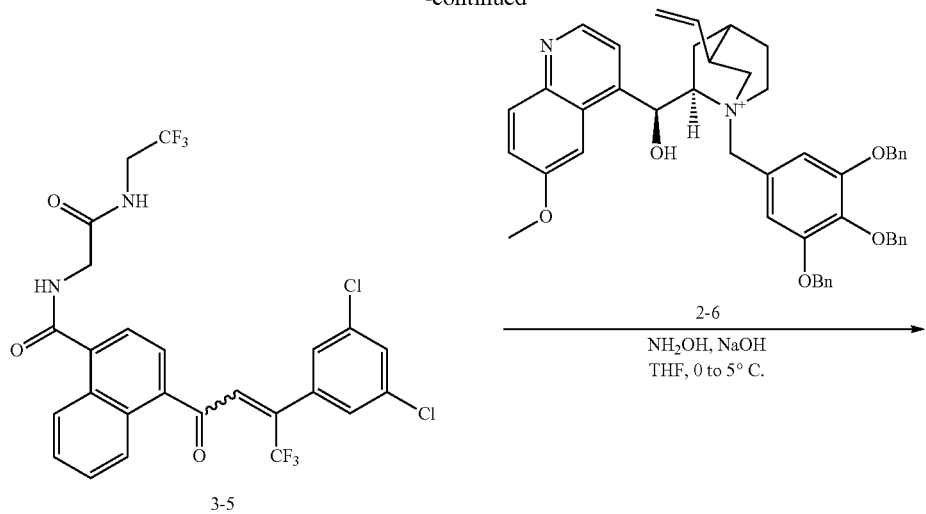

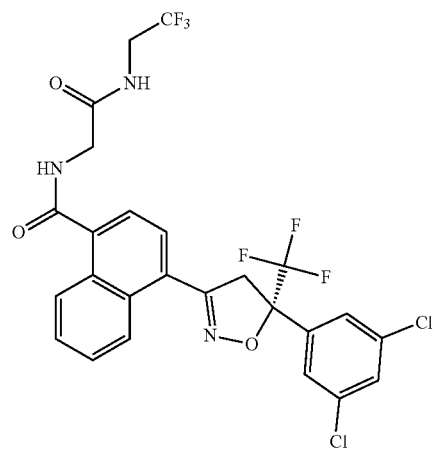

Step 3

Dichloromethane (150 ml, 30 vol.) and intermediate 3-5 (5.0 g, 8.66 mmol, 1.0 eq.) were charged into a 3-neck 500 ml flask and stirred for 10-30 minutes to dissolve the solid. The solution was then cooled to 0-5° C. and chiral phase transfer catalyst 2-6 was added (0.20 g, 0.026 mmol, 0.03 eq.). To the resulting solution was added a solution of $NH_2OH$ (50% w/w)/$NaOH$/$H_2O$ (20 ml, 5 vol.) drop-wise at 0 to 5° C. over 0.5-1 hour. The resulting reaction mixture was stirred for 2 hours at 0-5° C. and then sampled to check the reaction completion by HPLC, which showed less than 1% starting material. The layers were allowed to settle and the DCM layer was washed with saturated $KH_2PO_4$ (20 ml, 4 vol.) twice. The organic layer was then washed with brine (20 ml, 4 vol.) twice. The combined organic layers were concentrated under vacuum at 30-40° C. with concomitant addition of toluene (20 ml, 4 vol., twice) and then concentrated to dryness. Toluene (15 ml, 3 vol.) and the crude product (5.0 g) were charged into a 50 ml, 3-neck flask and the mixture was heated to 60-70° C. to dissolve the solid. The resulting mixture was cooled slowly to 45-50° C. over 2 hours and filtered. The filter cake was washed with toluene (10 ml, 2 vol.) and the filtrate was dried in an oven under vacuum at 40-50° C. for 6 hours to yield the product (2.5 g, yield: 49.0%, purity 99.4%, chiral purity: 99.3%).

Synthesis Example 4: Preparation of Compound (Ic) where $X^1$ and $X^2$=Cl and $X^3$=F The compound of formula (Ic), where $X^1$ and $X^2$=Cl and $X^3$=F, was prepared according to a process very similar to that shown in Schemes 2 and 3 above with the key difference that 1,3-dichloro-2-fluoro-5-iodobenzene was used as starting material instead of 1-chloro-2-fluoro-5-iodo-3-(trifluoromethyl)benzene. Step 3 of the process is described in detail below.

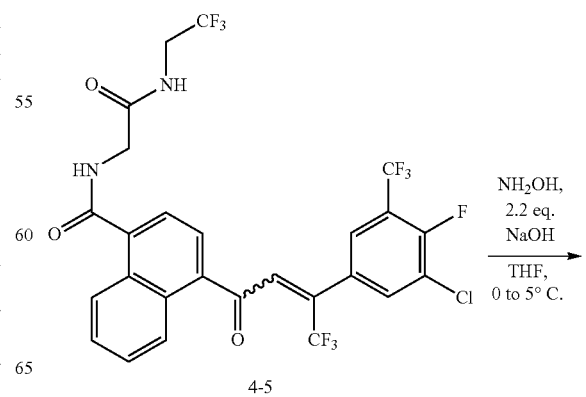

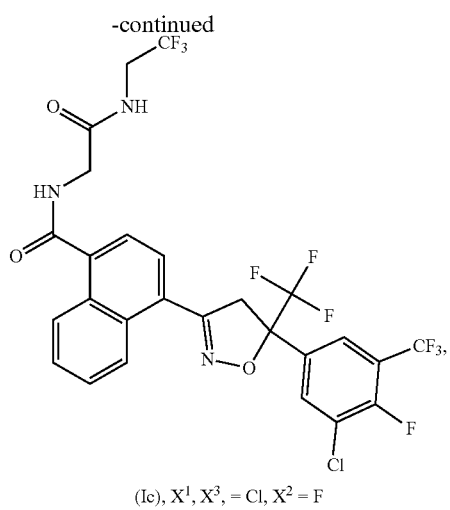

(Ic), $X^1, X^3 = Cl, X^2 = F$

Compound 4-5 (5, 8.4 mmol, 1.0 eq.) and THF (30 ml, 6 vol.) were charged into a 100 ml 3-neck flask. The solid was dissolved and NaOH (1.5 g, 50%, 18.5 mmol, 2.2 eq.) and hydroxylamine sulfate (0.6 g, 4.62 mmol, 0.55 eq.) were added to the mixture at 0-5° C. The reaction mixture was stirred for 90 minutes and sampled for analysis by HPLC, which indicated that less than 1.0% of the starting material was left. To the resulting mixture was added $KH_2PO_4$ (1.3 g, 10.9 mmol, 1.3 eq.) and the mixture was warmed to 20-25° C. The layers were allowed to separate and the organic layer isolated. The THF was removed by distillation with concomitant addition of acetonitrile (20 ml, 4 vol.) twice and then concentrated to dryness. Acetonitrile (20 ml, 4 vol.) was added to dissolve the residue and the solution was cooled to 25-30° C. slowly and stirred at this temperature for 180 min. The solid was filtered and the cake washed with acetonitrile (10 ml, 2 vol.). The solid was dried under vacuum at 30-35° C. for 6 hours to obtain the product (2.1 g, 98.9% purity, yield, 41.2%).

Veterinary Long-Acting Injectable Formulation Examples

The following long-acting injectable compositions are prepared by mixing the following ingredients:

Formulation Example 5

| | |
|---|---|
| Compound of formula (Ia) | 30% (w/v) |
| Ethanol | 9% (w/v) |
| PEG 400 | QS. |

Formulation Example 6

| | |
|---|---|
| Compound of formula (Ia) | 15% (w/w) |
| PEG 400 | 85% (w/w) |

Formulation Example 7

| | |
|---|---|
| Compound of formula (Ia) | 26% (w/w) |
| PEG 400 | 74% (w/w) |

Formulation Example 8

| | |
|---|---|
| Compound of formula (Ia) | 26% (w/w) |
| PEG 400 | 66% (w/w) |
| Ethanol | 8% (w/w) |

Formulation Example 9

| | |
|---|---|
| Compound of formula (Ia) | 26% (w/w) |
| PEG 400 | 66% (w/w) |
| Isopropanol | 8% (w/w) |

Formulation Example 10

| | |
|---|---|
| Compound of formula (Ia) | 26% (w/w) |
| PEG 400 | 64% (w/w) |
| Capryol 90 | 10% (w/w) |

Formulation Example 11

| | |
|---|---|
| Compound of formula (Ia) | 26% (w/w) |
| PEG | 66% (w/w) |
| Benzyl alcohol | 8% (w/w) |

Formulation Example 12

| | |
|---|---|
| Compound of formula (S)-Ia | 13% (w/w) |
| PEG 400 | 79% (w/w) |
| Ethanol | 8% (w/w) |

Formulation Example 13

| | |
|---|---|
| Compound of formula Ic where $X^1, X^3 = Cl, X^2$ is F | 30% (w/v) |
| Ethanol | 9% (w/v) |
| PEG 400 | QS. |

Formulation Example 14

| | |
|---|---|
| Compound of formula (Ic), where $X^1 = Cl, X^2 = F, X^3 = CF_3$ | 30% (w/v) |
| Ethanol | 9% (w/v) |
| PEG 400 | QS. |

Formulation Example 15

| | |
|---|---|
| Compound of formula (S)-Ic, where $X^1$, $X^3$ = Cl, $X^2$ is F | 13% (w/w) |
| PEG 400 | 79% (w/w) |
| Ethanol | 8% (w/w). |

Formulation Example 16

| | |
|---|---|
| Compound of formula (S)-Ic, where $X^1$ = Cl, $X^2$ = F, $X^3$ = $CF_3$ | 13% (w/w) |
| PEG 400 | 79% (w/w) |
| Ethanol | 8% (w/w). |

Formulation Example 17

| | |
|---|---|
| Compound of formula (S)-Ic, where $X^1$, $X^3$ = Cl, $X^2$ is H | 13% (w/w) |
| PEG 400 | 79% (w/w) |
| Ethanol | 8% (w/w). |

Formulation Example 18

| | |
|---|---|
| Compound of formula (S)-Ic, where $X^1$, $X^2$, $X^3$ = chloro | 13% (w/w) |
| PEG 400 | 79% (w/w) |
| Ethanol | 8% (w/w). |

Formulation Example 19

| | |
|---|---|
| Compound of formula (S)-Ic, $X^1$ = Cl, $X^2$ = F, $X^3$ = $CF_3$ | 10% (w/w) |
| Ethanol | 8% (w/w) |
| PEG 400 | QS. |

Formulation Example 20

| | |
|---|---|
| Compound of formula (S)-Ic, $X^1$ = Cl, $X^2$ = F, $X^3$ = $CF_3$ | 10% (w/v) |
| PEG 400 | QS. |

Formulation Example 21

| | |
|---|---|
| Compound of formula (S)-Ic, $X^1$ = Cl, $X^2$ = F, $X^3$ = $CF_3$ | 5% (w/v) |
| PEG 400 | QS. |

Formulation Example 22

| | |
|---|---|
| Compound of formula (S)-Ic, $X^1$ = Cl, $X^2$ = F, $X^3$ = $CF_3$ | 10% (w/v) |
| Ethanol | 3% (w/v) |
| PEG 400 | QS. |

Formulation Example 23

| | |
|---|---|
| Compound of formula (S)-Ic, $X^1$ = Cl, $X^2$ = F, $X^3$ = $CF_3$ | 5% (w/v) |
| Ethanol | 8% (w/v) |
| PEG 400 | QS. |

Formulation Example 24

| | |
|---|---|
| Compound of formula (S)-Ic, $X^1$ = Cl, $X^2$ = F, $X^3$ = $CF_3$ | 2.5% (w/v) |
| PEG 400 | QS. |

Formulation Example 25

| | |
|---|---|
| Compound of formula (S)-Ic, $X^1$ = Cl, $X^2$ = F, $X^3$ = $CF_3$ | 2.5% (w/v) |
| Ethanol | 8% (w/v) |
| PEG 400 | QS. |

Formulation Example 26

| | |
|---|---|
| Compound of formula (S)-Ie | 20% (w/v) |
| Medium chain triglycerides (e.g. Miglyol ® 812) | QS |
| Sorbitan monooleate | 0.5% (w/v) |
| Benzyl alcohol | 8% (w/v). |

Formulation Example 27

| | |
|---|---|
| Compound of formula (S)-Ie | 10% (w/v) |
| Medium chain triglycerides (e.g. Miglyol ® 812) | QS |
| Sorbitan monooleate | 0.5% (w/v) |
| Benzyl alcohol | 8% (w/v). |

Formulation Example 28

| | |
|---|---|
| Compound of formula (S)-Ie | 5% (w/v) |
| Medium chain triglycerides (e.g. Miglyol ® 812) | QS |
| Sorbitan monooleate | 0.5% (w/v) |
| Benzyl alcohol | 8% (w/v). |

Formulation Example 29

| | |
|---|---|
| Compound of formula (S)-Ie | 2.5% (w/v) |
| Medium chain triglycerides (e.g. Miglyol ® 812) | QS |
| Sorbitan monooleate | 0.5% (w/v) |
| Benzyl alcohol | 8% (w/v). |

Formulation Example 30

| | |
|---|---|
| Compound of formula (S)-Ie | 20% (w/v) |
| PEG 400 | QS |
| Medium chain triglycerides (e.g. Miglyol ® 812) | 30% (w/v) |
| Sorbitan monooleate | 0.5% (w/v) |
| Benzyl alcohol | 8% (w/v). |

Formulation Example 31

| | |
|---|---|
| Compound of formula (S)-Ie | 10% (w/v) |
| PEG 400 | QS |
| Medium chain triglycerides (e.g. Miglyol ® 812) | 30% (w/v) |
| Sorbitan monooleate | 0.5% (w/v) |
| Benzyl alcohol | 8% (w/v). |

Formulation Example 32

| | |
|---|---|
| Compound of formula (S)-Ie | 5% (w/v) |
| PEG 400 | QS |
| Medium chain triglycerides (e.g. Miglyol ® 812) | 30% (w/v) |
| Sorbitan monooleate | 0.5% (w/v) |
| Benzyl alcohol | 8% (w/v). |

Formulation Example 33

| | |
|---|---|
| Compound of formula (S)-Ie | 2.5% (w/v) |
| PEG 400 | QS |
| Medium chain triglycerides (e.g. Miglyol ® 812) | 30% (w/v) |
| Sorbitan monooleate | 0.5% (w/v) |
| Benzyl alcohol | 8% (w/v). |

Formulation Example 34

| | |
|---|---|
| Compound of formula (S)-Ie | 20% (w/v) |
| Propylene glycol dicaprylate/dicaprate (e.g. Miglyol ® 840) | QS |
| Sorbitan monooleate | 0.5% (w/v) |
| Benzyl alcohol | 8% (w/v). |

Formulation Example 35

| | |
|---|---|
| Compound of formula (S)-Ie | 10% (w/v) |
| Propylene glycol dicaprylate/dicaprate (e.g. Miglyol ® 840) | QS |
| Sorbitan monooleate | 0.5% (w/v) |
| Benzyl alcohol | 8% (w/v). |

Formulation Example 36

| | |
|---|---|
| Compound of formula (S)-Ie | 5% (w/v) |
| Propylene glycol dicaprylate/dicaprate (e.g. Miglyol ® 840) | QS |
| Sorbitan monooleate | 0.5% (w/v) |
| Benzyl alcohol | 8% (w/v). |

Formulation Example 37

| | |
|---|---|
| Compound of formula (S)-Ie | 2.5% (w/v) |
| Propylene glycol dicaprylate/dicaprate (e.g. Miglyol ® 840) | QS |
| Sorbitan monooleate | 0.5% (w/v) |
| Benzyl alcohol | 8% (w/v). |

Formulation Example 38

| | |
|---|---|
| Compound of formula (S)-Ie | 20% (w/v) |
| PEG 400 | QS |
| Propylene glycol dicaprylate/dicaprate (e.g. Miglyol ® 840) | 30% (w/v) |
| Sorbitan monooleate | 0.5% (w/v) |
| Benzyl alcohol | 8% (w/v). |

Formulation Example 39

| | |
|---|---|
| Compound of formula (S)-Ie | 10% (w/v) |
| PEG 400 | QS |
| Propylene glycol dicaprylate/dicaprate (e.g. Miglyol ® 840) | 30% (w/v) |
| Sorbitan monooleate | 0.5% (w/v) |
| Benzyl alcohol | 8% (w/v). |

Formulation Example 40

| | |
|---|---|
| Compound of formula (S)-Ie | 5% (w/v) |
| PEG 400 | QS |
| Propylene glycol dicaprylate/dicaprate (e.g. Miglyol ® 840) | 30% (w/v) |
| Sorbitan monooleate | 0.5% (w/v) |
| Benzyl alcohol | 8% (w/v). |

Formulation Example 41

| | |
|---|---|
| Compound of formula (S)-Ie | 2.5% (w/v) |
| PEG 400 | QS |
| Propylene glycol dicaprylate/dicaprate (e.g. Miglyol ® 840) | 30% (w/v) |
| Sorbitan monooleate | 0.5% (w/v) |
| Benzyl alcohol | 8% (w/v). |

Formulation Example 42

| | |
|---|---|
| Compound of formula (S)-Ie | 20% (w/v) |
| PEG 400 | QS |
| Propylene glycol dicaprylate/dicaprate (e.g. Miglyol ® 840) | 30% (w/v) |
| Sorbitan monooleate | 0.5% (w/v). |

Formulation Example 43

| | |
|---|---|
| Compound of formula (S)-Ie | 10% (w/v) |
| PEG 400 | QS |
| Propylene glycol dicaprylate/dicaprate (e.g. Miglyol ® 840) | 30% (w/v) |
| Sorbitan monooleate | 0.5% (w/v). |

Formulation Example 44

| | |
|---|---|
| Compound of formula (S)-Ie | 5% (w/v) |
| PEG 400 | QS |
| Propylene glycol dicaprylate/dicaprate (e.g. Miglyol ® 840) | 30% (w/v) |
| Sorbitan monooleate | 0.5% (w/v). |

Formulation Example 45

| | |
|---|---|
| Compound of formula (S)-Ie | 2.5% (w/v) |
| PEG 400 | QS |
| Propylene glycol dicaprylate/dicaprate (e.g. Miglyol ® 840) | 30% (w/v) |
| Sorbitan monooleate | 0.5% (w/v). |

Formulation Example 46

| | |
|---|---|
| Compound of formula (S)-Ie | 20% (w/v) |
| PEG 400 | QS |
| Medium chain triglycerides (e.g. Miglyol ® 812) | 30% (w/v) |
| Sorbitan monooleate | 0.5% (w/v). |

Formulation Example 47

| | |
|---|---|
| Compound of formula (S)-Ie | 10% (w/v) |
| PEG 400 | QS |
| Medium chain triglycerides (e.g. Miglyol ® 812) | 30% (w/v) |
| Sorbitan monooleate | 0.5% (w/v). |

Formulation Example 48

| | |
|---|---|
| Compound of formula (S)-Ie | 5% (w/v) |
| PEG 400 | QS |
| Medium chain triglycerides (e.g. Miglyol ® 812) | 30% (w/v) |
| Sorbitan monooleate | 0.5% (w/v). |

Formulation Example 49

| | |
|---|---|
| Compound of formula (S)-Ie | 2.5% (w/v) |
| PEG 400 | QS |
| Medium chain triglycerides (e.g. Miglyol ® 812) | 30% (w/v) |
| Sorbitan monooleate | 0.5% (w/v). |

Example 50: Viscosity of Long-Acting Formulations

The viscosity of the formulations in Examples 19-25 was measured to determine their suitability for injection. Polyethylene glycol 400 (PEG 400) was used as a reference. The conditions below were used for the measurement:

Instrument: LVDV-E Brookfield viscometer

Spindle: S31

Speed: 60 revolutions per minute (rpm)

Temperature: 25° C.

Sample volume: 9.0 mL

Measurement time: 2 to 3 minutes

| Formulation | Measured viscosity in cPs | Calculated Total Allowable Error |
|---|---|---|
| Example 19 | 75.5 | ±5.75 |
| Example 20 | 134.5 | ±6.344 |
| Example 21 | 109.5 | ±6.093 |
| Example 22 | 102.5 | ±6.023 |
| Example 23 | 60.0 | ±5.598 |
| Example 24 | 95.5 | ±5.953 |
| Example 25 | 55.5 | ±5.553 |
| PEG 400 | 93.0 | ±5.929 |

The viscosity of each of the compositions from Examples 18 to 24 was found to be suitable for administration by injection.

Efficacy Examples

Example 51: Efficacy of Injectable Formulation Against Rhipicephalus (Boophilus) microplus Ticks The efficacy of long-acting injectable compositions of the invention comprising the compounds of formula (Ie) and (S)-Ie, against Rhipicephalus microplus ticks on cattle was determined against an untreated control group. The efficacy of compositions comprising the compounds (Ie) and (S)-e were also compared with injectable compositions comprising afoxolaner (formula Ia, 4-[5-[3-chloro-5-(trifluoromethyl)phenyl]-4,5-dihydro-5-(trifluoromethyl)-3-isoxazolyl]-N-[2-oxo-2-[(2,2,2-trifluoroethyl)amino]ethyl]-1-naphthalanecarboxamide), and comparative compounds of formulae (If) and (S)-If shown below.

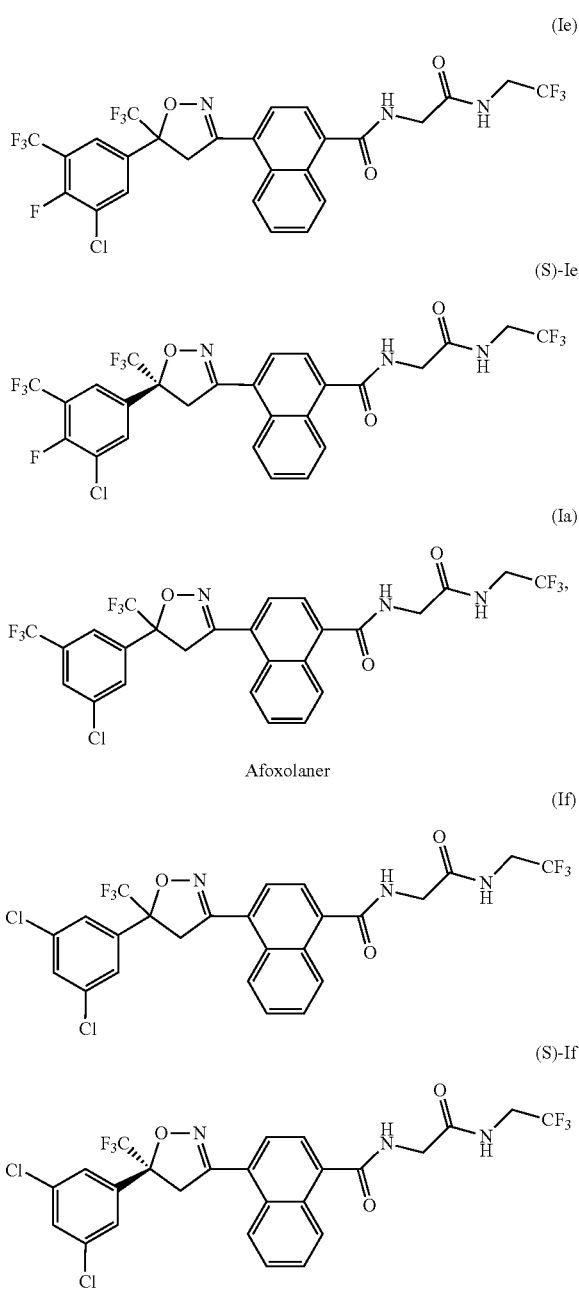

Afoxolaner

Each compound was formulated in an injectable composition at a concentration of 10% (w/v) in a carrier comprising 8% (w/v) ethanol and Q.S. with polyethylene glycol 400. The racemic compounds afoxolaner and (If) were dosed at 1.0 mg/kg body weight and the (S)-enantiomers ((S)-Ie and (S)-If) were dosed at 0.5 mg/kg body weight. Six healthy head of cattle were used in each study group. Cattle in Group 1 were untreated (control). Cattle in Groups 2, 3, 4, 5 and 6 were treated on Day 0 subcutaneously with injectable compositions comprising the compounds of formula Ie, (S)-If, (S)-Ie, afoxolaner (Ia) and (If), respectively. Several weeks before treatment, cattle were infested three times a week with approximately 2500 *Rhipicephalus microplus* larvae to establish ongoing infestations. Each animal was challenged by infestation with approximately 5000 *R. microplus* larvae on Days 7 and 21 and every 14 days thereafter. Ticks dropping from each animal in the previous 24 hours were collected daily and counted from Day 1 until the end of the study. The cattle in study Groups 3, 5 and 6 were not infested further when the efficacy of the treatment dropped significantly.

Tables 1A, 1B and 1C below show the total tick count % efficacy of injectable compositions comprising compounds of the invention ((Ie) and (S)-Ie) against *R. microplus* for selected days through Day 110 post treatment compared with the untreated control group and the comparison isoxazoline compounds. As evidenced from the data in Tables 1A, 1B and 1C below, the compositions comprising the compounds (Ie) and (S)-Ie of the invention dosed at 1.0 mg/kg and 0.5 mg/kg, respectively, provide surprising and unexpected efficacy against *Rhipicephalus microplus* ticks for an extended period of time compared with compositions comprising afoxolaner, (If) or (S)-If. Further, the efficacy of compounds (Je) and (S)-Ie is also faster-acting than compositions comprising the other isoxazoline compounds. The superior efficacy of compounds (Je) (racemic) and (S)-Ie against *R. microplus* ticks is unexpected and unpredictable.

TABLE 1A

Tick Count Efficacy Against *Rhipicephalus microplus*

| Treatment Group | Average % Efficacy (Tick Count) | | | | | | |
|---|---|---|---|---|---|---|---|
| | Day 5 | Day 10 | Day 20 | Day 30 | Day 40 | Day 49 | Day 55 |
| Group 2 (Ie) | 69 | 100 | 100 | 100 | 100 | 100 | 100 |
| Group 3 ((S)-If) | 39 | 27 | 33 | 86 | 100 | 36 | 0 |
| Group 4 ((S)-Ie) | 66 | 93 | 100 | 100 | 100 | 100 | 100 |
| Group 5 afoxolaner | 38 | 48 | 77 | 99 | 100 | 94 | 73 |
| Group 6 (If) | 70 | 62 | 57 | 84 | 100 | 70 | 14 |

TABLE 1B

Tick Count Efficacy Against *Rhipicephalus microplus*

| Treatment Group | Average % Efficacy (Tick Count) | | | | | | |
|---|---|---|---|---|---|---|---|
| | Day 60 | Day 65 | Day 70 | Day 75 | Day 80 | Day 85 | Day 88 |
| Group 2 (Ie) | 100 | 100 | 100 | 100 | 100 | 100 | 100 |
| Group 3 ((S)-If) | — | — | — | — | — | — | — |
| Group 4 ((S)-Ie) | 100 | 100 | 100 | 100 | 100 | 90 | 88 |
| Group 5 afoxolaner | 71 | 48 | 3 | 0 | — | — | — |
| Group 6 (If) | — | — | — | — | — | — | — |

TABLE 1C

Tick Count Efficacy against *Rhipicephalus microplus*

| Treatment Group | Average % Efficacy (Tick Count) | | | |
|---|---|---|---|---|
| | Day 95 | Day 100 | Day 105 | Day 110 |
| Group 2 (Ie) | 100 | 100 | 93 | 82 |
| Group 3 ((S)-If) | — | — | — | — |
| Group 4 ((S)-Ie) | 92 | 88 | 76 | 65 |
| Group 5 afoxolaner | — | — | — | — |
| Group 6 (If) | — | — | — | — |

Example 52: Efficacy of Long-Acting Injectable Compositions Against *Haematobia irritans* (Horn Fly) on Cattle The efficacy of a long-acting injectable composition comprising the compound of formula (S)-Ie against horn fly on cattle was evaluated. Two groups of 15 cattle were selected for the study and randomly assigned to one of two groups. The cattle in Group 1 were untreated and the cattle in Group 2 were treated with a long-acting composition of the invention containing 10% (w/v) of the compound of formula (S)-Ie in a carrier comprising 8% (w/v) ethanol in PEG 400 (QS). The composition was administered to the cattle in Group 2 at a dose of 0.25 mL/50 kg body weight. Each animal was naturally infested with horn flies, and horn fly counts were performed on Days-2, 3, 7, 10, 13, 16, 20, 23, 27, 30, 34, 37, 43, 45 and 48. Tables 2A and 2B below provide the horn fly counts and the % reduction of the treated group relative to the control.

TABLE 2A

| | Arithmetic Mean of Horn Fly Counts & % Reduction | | | | | | |
|---|---|---|---|---|---|---|---|
| Treatment Group | Day 3 | Day 7 | Day 10 | Day 13 | Day 16 | Day 20 | Day 23 | Day 27 |
| Group 1 (untreated) | 254.3 | 136.0 | 78.3 | 60.0 | 104.7 | 83.0 | 53.3 | 59.3 |
| Group 2 ((S)-Ie) | 26.7 | 35.0 | 16.0 | 22.0 | 44.7 | 36.0 | 30.7 | 22.7 |
| % Reduction | 89.5 | 74.3 | 79.6 | 63.3 | 57.3 | 56.6 | 42.5 | 61.8 |

TABLE 2B

| | Arithmetic Mean of Horn Fly Counts & % Reduction | | | | | |
|---|---|---|---|---|---|---|
| Treatment Group | Day 30 | Day 34 | Day 37 | Day 43 | Day 45 | Day 48 |
| Group 1 (untreated) | 71.0 | 47.7 | 73.3 | 43.0 | 66.7 | 44.0 |
| Group 2 ((S)-Ie) | 23.0 | 26.3 | 28.0 | 26.0 | 43.0 | 30.3 |
| % Reduction | 67.6 | 44.8 | 61.8 | 39.5 | 35.5 | 31.1 |

Having thus described in detail various embodiments of the present invention, it is to be understood that the invention defined by the above paragraphs is not to be limited to particular details set forth in the above description as many apparent variations thereof are possible without departing from the spirit or scope of the present invention.

What is claimed is:

1. A long-acting injectable composition for the treatment of an ectoparasitic infestation in an animal, said composition comprising:
   a) an effective amount of a parasiticidal isoxazoline active agent, which is a compound of formula (Ie):

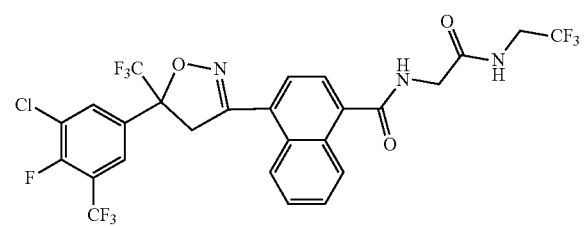

(Ie)

or a pharmaceutically acceptable salt thereof;

b) at least one pharmaceutically acceptable polymer which is a liquid PEG, and/or a neutral oil that is selected from triglycerides of fractionated plant fatty acids with chain lengths of $C_8$ to $C_{10}$;
   c) optionally, at least one co-solvent;
   d) optionally, an antioxidant; and
   e) optionally at least one pharmaceutically acceptable additive, excipient or mixtures thereof wherein no other pharmaceutically acceptable polymers are present, and wherein the composition treats the ectoparasitic infestation for about 3 to 6 months.

2. The long-acting injectable composition according to claim 1, wherein the isoxazoline active agent is enriched in an enantiomer.

3. The long-acting injectable composition according to claim 2, wherein the enantiomer is a compound of formula (S)-Ie:

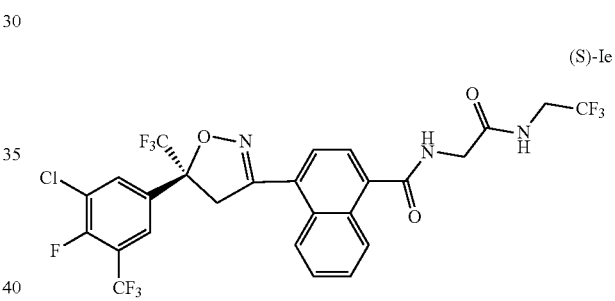

(S)-Ie or a pharmaceutically acceptable salt thereof.

4. The long-acting injectable composition according to claim 1, wherein the liquid PEG is PEG 200, PEG 300 or PEG 400, or a mixture thereof.

5. The long-acting injectable composition according to claim 1, wherein the composition comprises a co-solvent, and wherein the co-solvent is ethanol, isopropanol or benzyl alcohol, or a mixture thereof.

6. The long-acting injectable composition according to claim 1, wherein the composition further comprises a pharmaceutically acceptable excipient, and wherein the excipient is a surfactant.

7. The long-acting injectable composition according to claim 6, wherein the surfactant is selected from the group consisting of glyceryl monooleate, polyoxyethylene sorbitan fatty acid esters, sorbitan monooleate, polyvinyl alcohol, polysorbate 20, polysorbate 80, d-α-tocopherol polyethylene glycol 1000 succinate, sodium lauryl sulfate, co-polymers of ethylene oxide and propylene oxide, polyethylene glycol castor oil derivatives, propylene glycol monolaurate, glycerol caprylate/caprate, polyglycolized glycerides, PEG 300 caprylic/capric glycerides, PEG 400 caprylic/capric glycerides, PEG 300 oleic glycerides, PEG 300 linoleic glycerides, polyethylene glycol stearates, polyethylene glycol hydroxy stearates, and combinations thereof.

8. A long-acting injectable composition for the treatment of an ectoparasitic infestation in an animal, said composition comprising:
   a) about 0.5 to about 30% (w/v) of the isoxazoline compounds of formula (Ie)

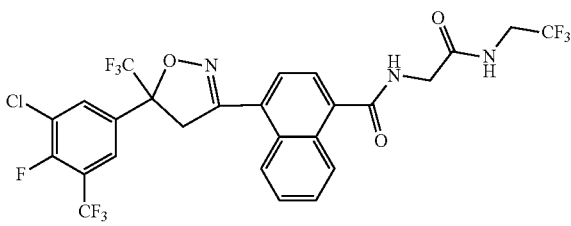 [SMILES: O=C(CNC(=O)c1ccc(C2=NOC(c3cc(Cl)c(F)c(C(F)(F)F)c3)(C(F)(F)F)C2)c2ccccc12)NCC(F)(F)F]

or a pharmaceutically acceptable salt thereof;
   b) a pharmaceutically acceptable polymer which is a liquid PEG, and/or a neutral oil that is selected from triglycerides of fractionated plant fatty acids with chain lengths of $C_8$ to $C_{10}$;
   c) optionally, about 5% to 40% (w/v) of co-solvent, wherein said co-solvent is selected from the group consisting of ethanol and isopropanol;
   d) optionally, about 0.01% to about 2% (w/v) of an antioxidant; and
   e) optionally about 0.01% to about 5% (w/v) of a pharmaceutically acceptable additive, excipient or mixtures thereof
   wherein the only pharmaceutically acceptable polymer present in said long-acting injectable composition is the liquid PEG, the liquid PEG and/or the neutral oil are present in the overall composition in a proportion representing the complement to 100% of the composition, and the composition treats the ectoparasitic infestation for about 3 to 6 months.

9. The long-acting composition according to any one of claims 1, 3, and 8, which further comprises an effective amount at least one additional active agent.

10. The long-acting composition according to claim 9, wherein the additional pharmaceutically active agent is a macrocyclic lactone, a neonicotinoid active agent, a 1-N-arylpyrazole active agent, a cyclic depsipeptide, a benzimidazole, an imidazothiazole, a tetrahydropyrimidine active agent, an organophosphate active agent, levamisole, a paraherquamide active agent, a marcfortine active agent, praziquantel, closantel, pyrantel, morantel, clorsulon, a spinosyn active agent, a spinosoid active agent, an amino acetonitrile active agent, an aryloazol-2-yl cyanoethyl active agent or an insect growth regulator.

11. The long-acting composition according to claim 10, wherein the macrocyclic lactone is abamectin, dimadectin, doramectin, emamectin, eprinomectin, ivermectin, latidectin, lepimectin, selamectin, ML-1,694,554, milbemectin, milbemycin D, moxidectin or nemadectin.

12. The composition according to claim 1 wherein the about 3 to 6 month treatment period is associated with a dose of the composition that is about 0.5 mg to about 2.5 mg of the isoxazoline active agent per kg of body weight of said animal.

13. The composition according to claim 2 wherein the about 3 to 6 month treatment period is associated with a dose of the composition that is about 0.5 mg to about 2.5 mg of the isoxazoline active agent per kg of body weight of said animal.

14. The composition according to claim 3 wherein the about 3 to 6 month treatment period is associated with a dose of the composition that is about 0.5 mg to about 2.5 mg of the isoxazoline active agent per kg of body weight of said animal.

15. The composition according to claim 8 wherein the about 3 to 6 month treatment period is associated with a dose of the composition that is about 0.5 mg to about 2.5 mg of the isoxazoline active agent per kg of body weight of said animal.

16. A method for treating ectoparasites in an animal in need thereof for a period of 3 to 6 months which comprises administering the long-acting injectable composition according to any one of claims 1, 3, and 8 to said animal.

17. The method according to claim 16 wherein the animal is a dog, a cat, an ovine or a bovine.

18. The method according to claim 16 wherein the ectoparasites are treated for about 5 to 6 months.

19. The method according to claim 16 wherein the ectoparasites are fleas and/or ticks.

* * * * *